(12) United States Patent
Inoue et al.

(10) Patent No.: US 10,835,551 B2
(45) Date of Patent: Nov. 17, 2020

(54) DOUBLE-STRANDED NUCLEIC ACID MOLECULE, DNA, VECTOR, CANCER CELL GROWTH INHIBITOR, CANCER CELL MIGRATION INHIBITOR, AND DRUG

(71) Applicant: Saitama Medical University, Saitama (JP)

(72) Inventors: Satoshi Inoue, Saitama (JP); Kazuhiro Ikeda, Saitama (JP); Kuniko Inoue, Saitama (JP)

(73) Assignee: SAITAMA MEDICAL UNIVERSITY, Saitama (JP)

( * ) Notice: Subject to any disclaimer, the term of this patent is extended or adjusted under 35 U.S.C. 154(b) by 0 days.

(21) Appl. No.: 16/732,725

(22) Filed: Jan. 2, 2020

(65) Prior Publication Data
US 2020/0121710 A1 Apr. 23, 2020

Related U.S. Application Data

(62) Division of application No. 15/318,576, filed as application No. PCT/JP2015/067054 on Jun. 12, 2015, now Pat. No. 10,561,679.

(30) Foreign Application Priority Data

Jun. 13, 2014 (JP) ................. 2014-122067

(51) Int. Cl.
| | |
|---|---|
| *A61K 31/713* | (2006.01) |
| *C12N 15/113* | (2010.01) |
| *A61P 35/04* | (2006.01) |
| *A61K 31/7105* | (2006.01) |
| *A61K 31/711* | (2006.01) |

(52) U.S. Cl.
CPC .......... *A61K 31/713* (2013.01); *A61K 31/711* (2013.01); *A61K 31/7105* (2013.01); *A61P 35/04* (2018.01); *C12N 15/113* (2013.01); *C12N 2310/14* (2013.01)

(58) Field of Classification Search
CPC ........ A61K 31/713; A61K 31/7105; A61K 31/711; A61P 35/04; C12N 15/113; C12N 2310/14
See application file for complete search history.

(56) References Cited

U.S. PATENT DOCUMENTS

2013/0184327 A1 7/2013 Inoue et al.

FOREIGN PATENT DOCUMENTS

WO 2011118778 A1 9/2011

OTHER PUBLICATIONS

Database GenBank [online], Accession No. XR_254050, http://www.ncbi.nlm.nih.gov/nucore/530438803?sat=21&satkey=4348943, Feb. 3, 2014 uploaded, Sep. 1, 2015 retrieved, Definition: Predicted: *Homo sapiens* uncharacterized LOC101928745 (LOC101928745), transcript variant X1, NcRNA.
Database GenBank [online], Accession No. XR_254052, http://www.ncbi.nlrn.nih.gov/nucore/530438805?sat=21&satkey=4348942, Feb. 3, 2014 uploaded, Sep. 1, 2015 retrieved, Definition: Predicted: *Homo sapiens* uncharacterized LOC101928745 (LOC101928745), transcript variant X3, NcRNA.
Horie, et al., "Nyugan no Byotai Shinko ni Kakawaru Antisense Chosa Hi-Code RNA no Dotei to Kino Kaiseki", Folia endocrinologica Japonica, vol. 90, Sep. 20, 2014, p. 646.
Musgrove, et al., "Biological determinants of endocrine resistance in breast cancer", Nature Review Cancer, vol. 9, Sep. 2009, pp. 631-643.
Ota, et al., "*Homo sapiens* TMPO antisense RNA 1 (TMPO-AS1), long oncoding", http://www.ncbi.nlnn.nih.qovinuccore/224548948?sat=18&satkey=18657333, Feb. 26, 2014.
International Search Report (PCT/ISA/210) dated Sep. 15, 2015, by the Japanese Patent Office as the International Searching Authority for International Application No. PCT/JP2015/067054.
Written Opinion (PCT/ISA/237) dated Sep. 15, 2015, by the Japanese Patent Office as the International Searching Authority for International Application No. PCT/JP2015/067054.

*Primary Examiner* — J. E. Angell
(74) *Attorney, Agent, or Firm* — Buchanan Ingersoll & Rooney PC

(57) ABSTRACT

A double-stranded nucleic acid molecule for suppressing expression of non-coding RNA, the double-stranded nucleic acid molecule including: (a) a sense strand containing a nucleotide sequence corresponding to a target sequence set forth in any one of SEQ ID NOs: 26 to 31; and (b) an antisense strand containing a nucleotide sequence which is complementary to the sense strand in the (a) to form a double strand with the sense strand, wherein the non-coding RNA contains a base sequence set forth in any one of SEQ ID NOs: 2 to 4, a part of the base sequence, or both of the base sequence and the part.

10 Claims, 25 Drawing Sheets
Specification includes a Sequence Listing.

siControl siTMPO-AS1-2 siCOL18A1-ASx-5

SEQUENCE LISTING

```
<160> NUMBER OF SEQ ID NOS: 51

<210> SEQ ID NO 1
<211> LENGTH: 3161
<212> TYPE: RNA
<213> ORGANISM: Homo sapiens

<400> SEQUENCE: 1
gggaggggcu gcaaacggcg gcgagcgcgc gcggcaaccg ccaaacgccc gccuuuguag      60
ccccggcccc gcguccuuac ccugccgacg gcugcucggc uccggcccgc ggcggcggcc     120
ccagagccga ggaccggggu gggcucgcgc ucuucgucac uggagaaguc cggggccccc     180
uugcuguugg ugccggcggg gagcggcggc cgguugcgag ccgugaggug cugcaggacc     240
gaggggucuu ccaggaacuc cggcaucucg gggaucugcg aagcccccuc cccacagccu     300
uugccgccgc cgcucacgcc ggcgcgcuug cuccuggccg gggaccgcgc ugccgccucc     360
gagccucacg gcuccugccc gggaagagcg cugcggagcg gaacaaaaac ucgcggacac     420
aaagccaagc cagacccgga cacaaaagac cccagagccg aacuacgaac caacugcggc     480
caagcuggaa gcucgcacca accccagccc acacacuaca ggcaggaggc gagcagccug     540
cuucgcccac gccccaagaa cgcgcgccgc cauuggcggg cgacgggagg aagcgcgcg     600 gugauuggcg agacggcucg cgcggguucc auuagccgcc gcgcugagcg agaggaggua     660
```

```
gaaacgcagu uuaaaaggcg cuggggcggg agccgaggcu cccggcccgc uucuguuuuc      720
guuuucucca cccuuccccu uagacgccga uaagggacag gucguacugc uuugugcgc      780 cguuccucu cccuccccca gcuugagaag cagcuuucgu cucggggluc gaucgccuac      840 gaacgcgccg aauccacgc cagugugagg acccuuggcu gggccuuucu uccucccggg      900
acacugaagc uccaagagua gccgcagccu ugccuucccc aaacgcuagc ccugaagggg      960
aagaaaagaa gcgaggcuug ucugcaggca ucuauauucc uugauuugau uuacuuuggg     1020
aggggagggg cggggaguua ccccucuccu cgcgaacgcu ucuuuuguuc cagaaaccca     1080
ggggaagcca gaccucuaca aucgggcacu uaaauuaccc uugaauuugu gacaaaagug     1140
uacuauacca uucacuucuu agugucauag uuggggcaug ucuaaauugu uuaauuugaa     1200
cagugcguuc agacgcaaga caaauucgcg cuugcauuuu uguugaaacc gucucuggcu     1260
uuggauccca ccacccgcaa gaauccuaaa ccuaacguuu gauaacaaaa cgaaggagaa     1320
cccuugggaa cccccucaau ggucaauuua aaauaacaga uggugcauaa uccuaaagga     1380
agacuaguga ccuauaauua ggccuagaac ccuaaucaaa cccguauuac cgauccaaau     1440
uaaaaccugg uagaaucuaa uacauugacu gcaauuaaaa uguuugccug gaaauuagua     1500
ucacugauga caaauauuug uauuucugau gaauauguau guuuaaagau gcuucuuuc     1560 uagaaaggaa aggagaccuu ggaugguaggg ugguguuaauc auuccccag aaucugagcu     1620 ccaaacuaug uuuuagaaac ugguuaaauu uuuuuaaau guuugccugc uuucuacauu     1680
gcuagguuag aauacauuua aaacaaacgc cuucacuaaa aauguuuccu augauuuaag     1740
cgacuuacuu uuauucaaau ugcgauauua uuucuuuuag ugauaauuau uuccuagag      1800 guaacuaauu ccuuuauaaa aaucucagua uucacauaca uuuaagcaau gguauuaagc     1860
ucauaaaugc aaauuaaaaa ucagguuuua auuagcaagu uguuagguag guuuuuauga     1920
ucccuuguaa aaguugcuug guuuuuuguc cucacagcuu cccuggacac auaggcaaau     1980
guuuuuaucu ucagaagggg aacugagcug agaggcaaag gaccaugacu uugcaaugac     2040
ugguaaccca guacguauaa ugcaagaacu gcauucuaga uacgccgaa auuaauguuu      2100 ccugggcaaa aacauuuuca uuaucuuuuu uuuaaucccu ggacauuagc uacagguggu     2160
uacuugcaga uuuacugcug uagagcucca aaauugagau uacacuuuuc agauucgcg      2220 uacccuaagg cuaagagguu gggcuauuga guuugguugg ucucuuuggu ccugauugcu     2280
acuuccaaac cauuucugcu cuuuucugcu ucaaaaauau uugaaguuca uaucuucugg     2340
cuaaaucacu uucuacucuc cuuccugcca ucauccacga gccuccuggu cacuuuccag     2400
aaauuauaga gcugcuugcc guagguuuuc cucaccaucc cucuugucua cauucuaucu     2460
gaauucagca ugcuuguagg ugacccaugc aacaccaaca cuuggccucu uagaccucug     2520
accucuucau cuccaacaau uuguccucu cuugcgucuu aaccacuucg guaucaguca      2580
gauucugaac cuugucauca guugaaaucu cagluucaag cuucccaauu gucaaucacu     2640
agccuuuuuu ucccagcuaa uuuaugguac ucucacuuac cuaauuaaga ccuccacgcu     2700
auuaacccca acacuuaaaa aaacucaacu cuucugcuuc ugccaucaug uaauaauuuu     2760
gcaacucacc ugacuuaaau ucccugauca guccuuuuca ucacucuuuu acaaacauuu     2820
ucaacucucu gaucucaaug ucuccuuuuu ugcuugaaag aaucucagcc uugcuuggac     2880
uaaaccaugc uccagcugaa cuuucucauu gcuacaucc aaacagcaaa agcugcggaa      2940
gaaaagucag ucauauaaca agcuaacugg uuuuaauuca ugaccucagu ccucucagga     3000
```

| | |
|---|---|
| gcacucaaca cuggcuggca augcuauucc agucucuggg uuaaccauuc auacguucac | 3060 |
| aucuccucaa auuucacauc cuuuuucccu accucucauu uuuagcuggu gaccuugccu | 3120 |
| caacuucaaa aaauaaaaac caccuaugag gaaugcuuca a | 3161 |

<210> SEQ ID NO 2
<211> LENGTH: 746
<212> TYPE: RNA
<213> ORGANISM: Homo sapiens

<400> SEQUENCE: 2

| | |
|---|---|
| uccaggaggc gccgccgccg cggccauggc caggggcacc ugcgcgggac aggcacgggg | 60 |
| ccagcauccu gagccccacc ugcaggcccu gggcgcuuuc cuccuggcag cugugccccc | 120 |
| acccgaccgg accgcucccu gcaaccagag agcccucaca ccagcaacac cccccagccu | 180 |
| gcucccuccu cgugugcgcg aaacucaugg cacuggcuug acggcuuucu cugaaacccu | 240 |
| cugauuccgc cuggcccauc cacacugucc cuucccggcc agggcucauc uccuaugccu | 300 |
| ggaccaaaca gcguagucuc cagucucccu gaucuccca cacgugggccc cacccauccu | 360 |
| cugaagcagc cccaggaggc agcagugacu ucacacuucu agugcccggc ccucccggcc | 420 |
| cuccucucug ggcuugcuug ccaggguccu cccaaccuga cugcugccuc ccaccuccuc | 480 |
| uccgccccug gagcucucca gccgcagccg cggggccugc uugggauucu ccucugcugg | 540 |
| caucauccu gccugccuca gccuuccag gcccaauccu gccgaucuc accucuuccc | 600 |
| gcccagccac cuggucgggu cccgaccagc aucgccuuc aaaccuggag uccuucccug | 660 |
| agugcuugcg gugcacugug aggaaggaaa ucaauguaaa ggauuaugac ccacauuuuu | 720 |
| uaaaaauaaa aagauuaagg agaaca | 746 |

<210> SEQ ID NO 3
<211> LENGTH: 1121
<212> TYPE: RNA
<213> ORGANISM: Homo sapiens

<400> SEQUENCE: 3

| | |
|---|---|
| uagcaagcag guguggaguc gagucggagg caggcgcugg cugcguggac ccccgggugg | 60 |
| gauuccaccc gcgacaaggc acccaggccc uuugggcggg gcuccccugg ggucccgcguc | 120 |
| cccgccgccu cccccgggcc ucugcugggc uggcuggagg caggaggccc cgguuagcag | 180 |
| guggugggga acugggucc ggggguuggag gcaggaaggu ccccacgggc cccgcgcacc | 240 |
| guuugccgcg cacgggaagc ggcgaggccg cgggggcagc ggcuucuggg cauuguucuc | 300 |
| ggaccgcgcg gcgcucgguu ggcaucaaag gggaccgcgc aacccgacac cacggcgggc | 360 |
| gcggggacag aggccugagg gcggcgggga cagaggcgca caaggccggg cccgcggcga | 420 |
| ggagccucaa cagggccagc auccugagcc ccaccugcag gcccugggcg cuuuccuccu | 480 |
| ggcagcugug cccccacccg accggaccgc ucccugcaac cagagagccc ucacaccagc | 540 |
| aacaccccc agccugcucc cuccucgugu gcgcgaaacu cauggcacug gcuugacggc | 600 |
| uuucucugaa acccucugau uccgccuggc ccauccacac ugucccuucc cggccagggc | 660 |
| ucaucuccua ugccuggacc aaacagcgua gucuccaguc cccugaucu ccccacacgu | 720 |
| ggccccaccc auccucugaa gcagccccag gaggcagcag ugacuucaca cuucuagugc | 780 |
| ccggccucc cggcccuccu cucuggcuu gcuugcagg guccuccccaa ccugacugcu | 840 |
| gccucccacc uccuccgc cccugagcu ccagccgc agccgcgggg ccugcuuggg | 900 |
| auucuccucu gcuggcauca ucccugccug ccucagccuu cccaggccca auccugcccg | 960 |

| | | | | |
|---|---|---|---|---|
| aucucaccuc | uucccgccca | gccaccuggu | cgggucccga | ccagcaucug ccuucaaacc | 1020 |
| uggaguccuu | cccugagugc | uugcggugca | cugugaggaa | ggaaaucaau guaaaggauu | 1080 |
| augacccaca | uuuuuaaaa | auaaaaagau | uaaggagaac | a | 1121 |

<210> SEQ ID NO 4
<211> LENGTH: 806
<212> TYPE: RNA
<213> ORGANISM: Homo sapiens

<400> SEQUENCE: 4

| | | | | |
|---|---|---|---|---|
| ggcggggacg | ggcgaggacg | gacggggaca | cgucccgccc | cgagggaacc gcccgaggcu | 60 |
| gcgacccagc | acagggcccg | ggggcugccc | cgcgaggaag | cccagguuua ugcggaaggg | 120 |
| ccagcauccu | gagccccacc | ugcaggcccu | gggcgcuuuc | cuccuggcag cugugccccc | 180 |
| acccgaccgg | accgucccu | gcaaccagag | agcccucaca | ccagcaacac cccccagccu | 240 |
| gcucccuccu | cgugugcgcg | aaacucaugg | cacuggcuug | acggcuuucu cugaaacccu | 300 |
| cugauuccgc | cuggcccauc | cacacugucc | cuucccggcc | agggcucauc uccuaugccu | 360 |
| ggaccaaaca | gcguagucuc | cagucucccu | gaucucccca | cacgugggccc cacccauccu | 420 |
| cugaagcagc | ccaggaggc | agcagugacu | ucacacuucu | agugcccggc ccuccggcc | 480 |
| cuccucucug | ggcuugcuug | ccagggguccu | cccaaccuga | cugcugccuc ccaccuccuc | 540 |
| uccgcccug | gagcucucca | gccgcagccg | cggggccugc | uugggauucu ccucugcugg | 600 |
| caucaucccu | gccugcccuca | gccuuccag | gcccaauccu | gcccgaucuc accucuuccc | 660 |
| gcccagccac | cuggucgggu | cccgaccagc | aucgccuuc | aaaccuggag ccuucccug | 720 |
| agugcuugcg | gugcacugug | aggaaggaaa | ucaauguaaa | ggauuaugac ccacauuuuu | 780 |
| uaaaaauaaa | aagauuaagg | agaaca | | | 806 |

<210> SEQ ID NO 5
<211> LENGTH: 21
<212> TYPE: DNA
<213> ORGANISM: Homo sapiens

<400> SEQUENCE: 5
gaagactagt gacctataat t            21

<210> SEQ ID NO 6
<211> LENGTH: 21
<212> TYPE: DNA
<213> ORGANISM: Homo sapiens

<400> SEQUENCE: 6
gagccgaact acgaaccaac t            21

<210> SEQ ID NO 7
<211> LENGTH: 21
<212> TYPE: DNA
<213> ORGANISM: Homo sapiens

<400> SEQUENCE: 7
ggacaggtcg tactgctttt g            21

<210> SEQ ID NO 8
<211> LENGTH: 21
<212> TYPE: DNA
<213> ORGANISM: Homo sapiens

```
<400> SEQUENCE: 8
gaatcctaaa cctaacgttt g                                              21

<210> SEQ ID NO 9
<211> LENGTH: 21
<212> TYPE: DNA
<213> ORGANISM: Homo sapiens

<400> SEQUENCE: 9
cctaacgttt gataacaaaa c                                              21

<210> SEQ ID NO 10
<211> LENGTH: 21
<212> TYPE: DNA
<213> ORGANISM: Homo sapiens

<400> SEQUENCE: 10
cccgtattac cgatccaaat t                                              21

<210> SEQ ID NO 11
<211> LENGTH: 21
<212> TYPE: DNA
<213> ORGANISM: Homo sapiens

<400> SEQUENCE: 11
cgcgaacgct tcttttgttc c                                              21

<210> SEQ ID NO 12
<211> LENGTH: 21
<212> TYPE: RNA
<213> ORGANISM: Artificial Sequence
<220> FEATURE:
<223> OTHER INFORMATION: siRNA

<400> SEQUENCE: 12
gaagacuagu gaccuauaau u                                              21

<210> SEQ ID NO 13
<211> LENGTH: 21
<212> TYPE: RNA
<213> ORGANISM: Artificial Sequence
<220> FEATURE:
<223> OTHER INFORMATION: siRNA

<400> SEQUENCE: 13
uuauagguca cuagucuucc u                                              21

<210> SEQ ID NO 14
<211> LENGTH: 21
<212> TYPE: RNA
<213> ORGANISM: Artificial Sequence
<220> FEATURE:
<223> OTHER INFORMATION: siRNA

<400> SEQUENCE: 14
gagccgaacu acgaaccaac u                                              21

<210> SEQ ID NO 15
<211> LENGTH: 21
<212> TYPE: RNA
<213> ORGANISM: Artificial Sequence
<220> FEATURE:
<223> OTHER INFORMATION: siRNA

<400> SEQUENCE: 15
```

-continued uugguucgua guucggcucu g					21

<210> SEQ ID NO 16
<211> LENGTH: 21
<212> TYPE: RNA
<213> ORGANISM: Artificial Sequence
<220> FEATURE:
<223> OTHER INFORMATION: siRNA

<400> SEQUENCE: 16
ggacaggucg uacugcuuuu g					21

<210> SEQ ID NO 17
<211> LENGTH: 21
<212> TYPE: RNA
<213> ORGANISM: Artificial Sequence
<220> FEATURE:
<223> OTHER INFORMATION: siRNA

<400> SEQUENCE: 17
aaagcaguac gaccuguccc u					21

<210> SEQ ID NO 18
<211> LENGTH: 21
<212> TYPE: RNA
<213> ORGANISM: Artificial Sequence
<220> FEATURE:
<223> OTHER INFORMATION: siRNA

<400> SEQUENCE: 18
gaauccuaaa ccuaacguuu g					21

<210> SEQ ID NO 19
<211> LENGTH: 21
<212> TYPE: RNA
<213> ORGANISM: Artificial Sequence
<220> FEATURE:
<223> OTHER INFORMATION: siRNA

<400> SEQUENCE: 19
aacguuaggu uuaggauucu u					21

<210> SEQ ID NO 20
<211> LENGTH: 21
<212> TYPE: RNA
<213> ORGANISM: Artificial Sequence
<220> FEATURE:
<223> OTHER INFORMATION: siRNA

<400> SEQUENCE: 20
ccuaacguuu gauaacaaaa c					21

<210> SEQ ID NO 21
<211> LENGTH: 21
<212> TYPE: RNA
<213> ORGANISM: Artificial Sequence
<220> FEATURE:
<223> OTHER INFORMATION: siRNA

<400> SEQUENCE: 21
uuuguuauca aacguuaggu u					21

<210> SEQ ID NO 22
<211> LENGTH: 21
<212> TYPE: RNA

```
<213> ORGANISM: Artificial Sequence
<220> FEATURE:
<223> OTHER INFORMATION: siRNA

<400> SEQUENCE: 22
cccguauuac cgauccaaau u                                              21

<210> SEQ ID NO 23
<211> LENGTH: 21
<212> TYPE: RNA
<213> ORGANISM: Artificial Sequence
<220> FEATURE:
<223> OTHER INFORMATION: siRNA

<400> SEQUENCE: 23
uuuggaucgg uaauacgggu u                                              21

<210> SEQ ID NO 24
<211> LENGTH: 21
<212> TYPE: RNA
<213> ORGANISM: Artificial Sequence
<220> FEATURE:
<223> OTHER INFORMATION: siRNA

<400> SEQUENCE: 24
cgcgaacgcu ucuuuuguuc c                                              21

<210> SEQ ID NO 25
<211> LENGTH: 21
<212> TYPE: RNA
<213> ORGANISM: Artificial Sequence
<220> FEATURE:
<223> OTHER INFORMATION: siRNA

<400> SEQUENCE: 25
aacaaaagaa gcguucgcga g                                              21

<210> SEQ ID NO 26
<211> LENGTH: 19
<212> TYPE: DNA
<213> ORGANISM: Homo sapiens

<400> SEQUENCE: 26
gcactgtgag gaaggaaat                                                 19

<210> SEQ ID NO 27
<211> LENGTH: 21
<212> TYPE: DNA
<213> ORGANISM: Homo sapiens

<400> SEQUENCE: 27
gcttgacggc tttctctgaa a                                              21

<210> SEQ ID NO 28
<211> LENGTH: 21
<212> TYPE: DNA
<213> ORGANISM: Homo sapiens

<400> SEQUENCE: 28
ggaccaaaca gcgtagtctc c                                              21

<210> SEQ ID NO 29
<211> LENGTH: 21
<212> TYPE: DNA
<213> ORGANISM: Homo sapiens
```

```
<400> SEQUENCE: 29
cttcaaacct ggagtccttc c                                              21

<210> SEQ ID NO 30
<211> LENGTH: 21
<212> TYPE: DNA
<213> ORGANISM: Homo sapiens

<400> SEQUENCE: 30
gcctgcttgg gattctcctc t                                              21

<210> SEQ ID NO 31
<211> LENGTH: 21
<212> TYPE: DNA
<213> ORGANISM: Homo sapiens

<400> SEQUENCE: 31
gccagggctc atctcctatg c                                              21

<210> SEQ ID NO 32
<211> LENGTH: 21
<212> TYPE: DNA
<213> ORGANISM: Artificial Sequence
<220> FEATURE:
<223> OTHER INFORMATION: Artificial Sequence, RNA-DNA Chimera

<400> SEQUENCE: 32
gcacugugag gaaggaaaut t                                              21

<210> SEQ ID NO 33
<211> LENGTH: 21
<212> TYPE: DNA
<213> ORGANISM: Artificial Sequence
<220> FEATURE:
<223> OTHER INFORMATION: Artificial Sequence, RNA-DNA Chimera

<400> SEQUENCE: 33
auuuccuucc ucacagugct t                                              21

<210> SEQ ID NO 34
<211> LENGTH: 21
<212> TYPE: RNA
<213> ORGANISM: Artificial Sequence
<220> FEATURE:
<223> OTHER INFORMATION: siRNA

<400> SEQUENCE: 34
gcuugacggc uuucucugaa a                                              21

<210> SEQ ID NO 35
<211> LENGTH: 21
<212> TYPE: RNA
<213> ORGANISM: Artificial Sequence
<220> FEATURE:
<223> OTHER INFORMATION: siRNA

<400> SEQUENCE: 35
ucagagaaag ccgucaagcc a                                              21

<210> SEQ ID NO 36
<211> LENGTH: 21
<212> TYPE: RNA
<213> ORGANISM: Artificial Sequence
<220> FEATURE:
```

```
<223> OTHER INFORMATION: siRNA

<400> SEQUENCE: 36
ggaccaaaca gcguagucuc c                                              21

<210> SEQ ID NO 37
<211> LENGTH: 21
<212> TYPE: RNA
<213> ORGANISM: Artificial Sequence
<220> FEATURE:
<223> OTHER INFORMATION: siRNA

<400> SEQUENCE: 37
agacuacgcu guuuggucca g                                              21

<210> SEQ ID NO 38
<211> LENGTH: 21
<212> TYPE: RNA
<213> ORGANISM: Artificial Sequence
<220> FEATURE:
<223> OTHER INFORMATION: siRNA

<400> SEQUENCE: 38
cuucaaaccu ggaguccuuc c                                              21

<210> SEQ ID NO 39
<211> LENGTH: 21
<212> TYPE: RNA
<213> ORGANISM: Artificial Sequence
<220> FEATURE:
<223> OTHER INFORMATION: siRNA

<400> SEQUENCE: 39
aaggacucca gguuugaagg c                                              21

<210> SEQ ID NO 40
<211> LENGTH: 21
<212> TYPE: RNA
<213> ORGANISM: Artificial Sequence
<220> FEATURE:
<223> OTHER INFORMATION: siRNA

<400> SEQUENCE: 40
gccugcuugg gauucccuc u                                               21

<210> SEQ ID NO 41
<211> LENGTH: 21
<212> TYPE: RNA
<213> ORGANISM: Artificial Sequence
<220> FEATURE:
<223> OTHER INFORMATION: siRNA

<400> SEQUENCE: 41
aggagaaucc caagcaggcc c                                              21

<210> SEQ ID NO 42
<211> LENGTH: 21
<212> TYPE: RNA
<213> ORGANISM: Artificial Sequence
<220> FEATURE:
<223> OTHER INFORMATION: siRNA

<400> SEQUENCE: 42
gccagggcuc aucccuaug c                                               21
```

```
<210> SEQ ID NO 43
<211> LENGTH: 21
<212> TYPE: RNA
<213> ORGANISM: Artificial Sequence
<220> FEATURE:
<223> OTHER INFORMATION: siRNA

<400> SEQUENCE: 43
auaggagaug agcccuggcc g                                              21

<210> SEQ ID NO 44
<211> LENGTH: 21
<212> TYPE: RNA
<213> ORGANISM: Artificial Sequence
<220> FEATURE:
<223> OTHER INFORMATION: siRNA

<400> SEQUENCE: 44
guaccgcacg ucauucguau c                                              21

<210> SEQ ID NO 45
<211> LENGTH: 21
<212> TYPE: RNA
<213> ORGANISM: Artificial Sequence
<220> FEATURE:
<223> OTHER INFORMATION: siRNA

<400> SEQUENCE: 45
uacgaaugac gugcgguacg u                                              21

<210> SEQ ID NO 46
<211> LENGTH: 23
<212> TYPE: DNA
<213> ORGANISM: Artificial Sequence
<220> FEATURE:
<223> OTHER INFORMATION: primer

<400> SEQUENCE: 46
ggtggtctcc tctgacttca aca                                            23

<210> SEQ ID NO 47
<211> LENGTH: 19
<212> TYPE: DNA
<213> ORGANISM: Artificial Sequence
<220> FEATURE:
<223> OTHER INFORMATION: primer

<400> SEQUENCE: 47
gtggtcgttg agggcaatg                                                 19

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
gccagggctc atctcctatg                                                20

<210> SEQ ID NO 49
<211> LENGTH: 23
<212> TYPE: DNA
<213> ORGANISM: Artificial Sequence
<220> FEATURE:
<223> OTHER INFORMATION: primer
```

```
<400> SEQUENCE: 49
ggagatcagg gagactggag act                                            23

<210> SEQ ID NO 50
<211> LENGTH: 21
<212> TYPE: DNA
<213> ORGANISM: Artificial Sequence
<220> FEATURE:
<223> OTHER INFORMATION: primer

<400> SEQUENCE: 50
tctccaccct tccccttaga c                                              21

<210> SEQ ID NO 51
<211> LENGTH: 17
<212> TYPE: DNA
<213> ORGANISM: Artificial Sequence
<220> FEATURE:
<223> OTHER INFORMATION: primer

<400> SEQUENCE: 51
aacggcgcac aaaagca                                                   17
```

DOUBLE-STRANDED NUCLEIC ACID MOLECULE, DNA, VECTOR, CANCER CELL GROWTH INHIBITOR, CANCER CELL MIGRATION INHIBITOR, AND DRUG

CROSS-REFERENCE TO RELATED APPLICATIONS

This application is a divisional of U.S. application Ser. No. 15/318,576, filed Dec. 13, 2016, now U.S. Pat. No. 10,561,679, which is a U.S. national stage application of PCT/JP2015/067054, filed Jun. 12, 2015, which claims priority to Japanese Patent Application No. 2014-122067, filed Jun. 13, 2014, the contents of all of which are hereby incorporated by reference.

TECHNICAL FIELD

The present invention relates to: a double-stranded nucleic acid molecule which can be suitably used for prevention or treatment of cancer; DNA and a vector each containing the double-stranded nucleic acid molecule; a cancer cell proliferation suppressant and a cancer cell movement suppressant each containing at least one of the double-stranded nucleic acid molecule, the DNA, and the vector; and a drug containing at least one of the cancer cell proliferation suppressant and the cancer cell movement suppressant.

BACKGROUND ART

Among cancers, breast cancer is a cancer that women suffer from most frequently. Along with westernization of diets and aging of population, the number of patients has continued to increase in recent years.

As therapeutic techniques for breast cancer, clinically, surgical treatments such as mammary gland resection, chemotherapy using anticancer drugs, and radiation therapy have been widely used.

The mammary epithelium proliferates by the action of estrogen which is a female hormone, and thus also in breast cancer of estrogen receptor positive, the proliferation is stimulated in an estrogen dependent manner. Therefore, in general, for tumors of estrogen receptor positive or progesterone receptor positive which are expected to be estrogen sensitive, hormone therapy is performed using antiestrogens or aromatase suppressants that cause inhibition of estrogen production. Moreover, hormone therapy is performed for advanced breast cancer as well.

Meanwhile, even in breast cancer to which hormone therapy is initially recognized to be effective, there is a problem with acquisition of resistance during the course of therapy (see, for example, NPL 1). Conceivable causes of this include: excessive expression or activation of an estrogen receptor that can occur after an estrogen depleted state; and enhancement of the action of molecules that are originally estrogen receptor targeting factors and cause cancerous proliferation, even after acquisition of resistance.

Therefore, therapy for targeting molecules downstream of an estrogen signal, especially factors causing cancerous proliferation, is expected as an effective therapeutic technique in place of the existing hormone therapy.

However, the molecular mechanism of resistance to hormone therapy has not yet been revealed in detail, and thus any sufficient therapeutic method for breast cancer after acquisition of resistance and therapy-resistant breast cancer has not yet been developed.

In addition, for tumor that is growth factor HER2 molecule positive in breast cancer of estrogen receptor negative, molecular targeted therapy is also performed including monoclonal antibody therapy against HER2. However, at present, there is no effective therapeutic method for breast cancer of estrogen receptor negative, progesterone receptor negative, and HER2 negative.

As described above, there is a limit in the existing therapeutic techniques, and strong demand has currently arisen for prompt development of a method for suppressing breast cancer including refractory breast cancer to which the existing breast cancer therapeutic techniques are not recognized to be effective.

Also, for other cancers than breast cancer, strong demand has currently arisen for prompt development of a method for suppressing cancer.

CITATION LIST

Non-Patent Literature

NPL 1: Musgrove E A, Sutherland R L. Biological determinants of endocrine resistance in breast cancer. Nat Rev Cancer. 9:631-643, 2009

SUMMARY OF INVENTION

Technical Problem

The present invention aims to solve the above existing problems and achieve the following object. Specifically, an object of the present invention is to provide: a double-stranded nucleic acid molecule which targets non-coding RNA containing a base sequence set forth in any one of SEQ ID NOs: 1 to 4, a part of the base sequence, or both of the base sequence and the part to suppress expression of the non-coding RNA to thereby be able to effectively suppress proliferation of cancer cells and which can be suitably used for prevention or treatment of cancer; DNA and a vector each containing the double-stranded nucleic acid molecule; a cancer cell proliferation suppressant and a cancer cell movement suppressant each containing at least one of the double-stranded nucleic acid molecule, the DNA, and the vector; and a drug containing at least one of the cancer cell proliferation suppressant and the cancer cell movement suppressant.

Solution to Problem

Means for solving the above problems are as follows.

<1> A double-stranded nucleic acid molecule for suppressing expression of non-coding RNA, the double-stranded nucleic acid molecule including:

(a) a sense strand containing a nucleotide sequence corresponding to a target sequence set forth in any one of SEQ ID NOs: 5 to 11 and 26 to 31; and (b) an antisense strand containing a nucleotide sequence which is complementary to the sense strand in the (a) to form a double strand with the sense strand, wherein the non-coding RNA contains a base sequence set forth in any one of SEQ ID NOs: 1 to 4, a part of the base sequence, or both of the base sequence and the part.

<2> DNA including a nucleotide sequence encoding the double-stranded nucleic acid molecule according to <1>.

<3> A vector including the DNA according to <2>.

<4> A cancer cell proliferation suppressant including
at least one of the double-stranded nucleic acid molecule according to <1>, the DNA according to <2>, and the vector according to <3>.
<5> A method for suppressing proliferation of cancer cells, the method including
allowing the cancer cell proliferation suppressant according to <4> to act on the cancer cells.
<6> A cancer cell movement suppressant including
at least one of the double-stranded nucleic acid molecule according to <1>, the DNA according to <2>, and the vector according to <3>.
<7> A method for suppressing movements of cancer cells, the method including
allowing the cancer cell movement suppressant according to <6> to act on the cancer cells.
<8> A drug for preventing or treating cancer, the drug including
at least one of the cancer cell proliferation suppressant according to <4> and the cancer cell movement suppressant according to <6>.
<9> A method for preventing or treating cancer, the method including
administering the drug according to <8> to an individual.

Advantageous Effects of Invention

The present invention can solve the above existing problems and provide: a double-stranded nucleic acid molecule which targets non-coding RNA containing a base sequence set forth in any one of SEQ ID NOs: 1 to 4, a part of the base sequence, or both of the base sequence and the part to suppress expressions of the non-coding RNA to thereby be able to effectively suppress proliferation of cancer cells and which can be suitably used for prevention or treatment of cancer; DNA and a vector each containing the double-stranded nucleic acid molecule; a cancer cell proliferation suppressant and a cancer cell movement suppressant each containing at least one of the double-stranded nucleic acid molecule, the DNA, and the vector; and a drug containing at least one of the cancer cell proliferation suppressant and the cancer cell movement suppressant.

Figure 1A:
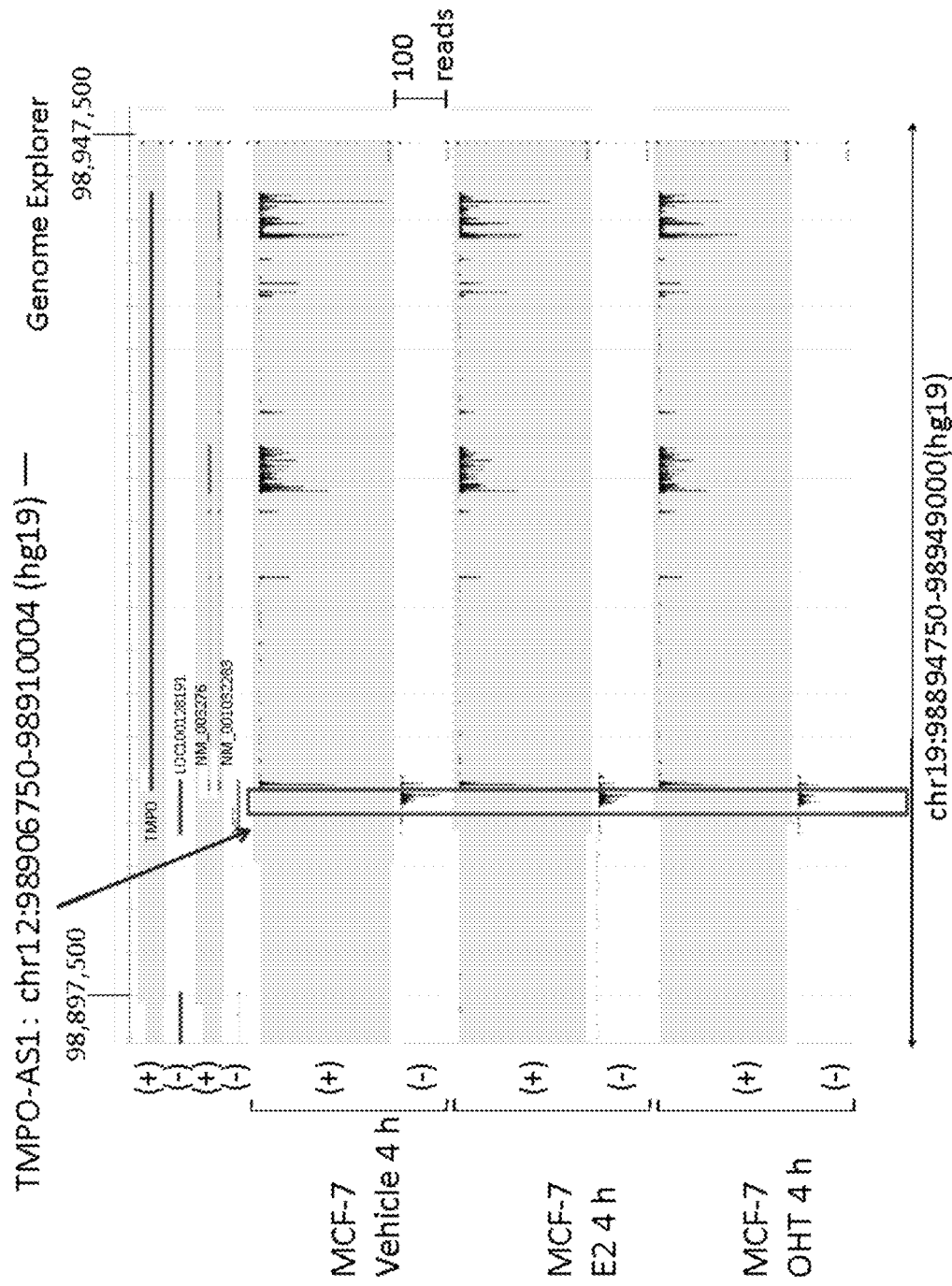
FIG. 1A illustrates analysis results of expression of TMPO-AS1 in Test Example 2-1-1.

DESCRIPTION OF EMBODIMENTS (Double-Stranded Nucleic Acid Molecule)
A double-stranded nucleic acid molecule of the present invention is a double-stranded nucleic acid molecule for suppressing expression of non-coding RNA, the double-stranded nucleic acid molecule including: (a) a sense strand containing a nucleotide sequence corresponding to a target sequence set forth in any one of SEQ ID NOs: 5 to 11 and 26 to 31; and (b) an antisense strand containing a nucleotide sequence which is complementary to the sense strand in the (a) to form a double strand with the sense strand.
Note that, in the present invention, the phrase "double-stranded nucleic acid molecule" refers to a double-stranded nucleic acid molecule in which a desired sense strand and an antisense strand are hybridized with each other.
<Non-Coding RNA>
The non-coding RNA contains a base sequence set forth in any one of SEQ ID NOs: 1 to 4, a part of the base sequence, or both of the base sequence and the part.
The expression of the non-coding RNA is induced in an estrogen dependent manner as indicated in the below-described Test Examples.
—TMPO-AS1—
The base sequence set forth in SEQ ID NO: 1 is a base sequence of TMPO-AS1. The TMPO-AS1 is considered to be an antisense transcript of TMPO (thymopoietin) gene.

Sequence information of the TMPO-AS1 can be easily obtained through public databases such as RefSeq database (NCBI Reference Sequence database).

The base sequence set forth in SEQ ID NO: 1 is registered in the RefSeq database as "*Homo sapiens* TMPO antisense RNA 1 (TMPO-AS1), long non-coding RNA" (NR_027157.1;gi 224548948), where the RNA length is 3,161 bp and the genomic position is chr12:98906751-98910004(hg19).

—COL18A1-ASx—

The base sequences set forth in SEQ ID NOs: 2 to 4 are base sequences of COL18A1-ASx. The COL18A1-ASx is located in the antisense direction immediately upstream of the transcription initiation site of COL18A1 in the vicinity of COL18A1-AS2 which is an antisense transcript of COL18A1 gene, and the COL18A1-ASx is present on the estrogen receptor α binding site.

Sequence information of the COL18A1-ASx can be easily obtained through public databases such as RefSeq database (NCBI Reference Sequence database).

As for the above COL18A1-ASx, the following three kinds of variants thereof are registered in the RefSeq database as "*Homo sapiens* uncharacterized LOC101928745".
(1) LOC101928745, transcript variant X1, ncRNA (XR_254050.1;gi 530438803)

The putative RNA length is 746 bp (see SEQ ID NO: 2) and the genomic position is chr21:46823724-46825332.
(2) LOC101928745, transcript variant X2, ncRNA (XR_254051.1;gi 530438804)

The putative RNA length is 1,121 bp (see SEQ ID NO: 3) and the genomic position is chr21:46823724-46826253.
(3) LOC101928745, transcript variant X3, misc_RNA (XR_254052.1;gi 530438805)

The putative RNA length is 806 bp (see SEQ ID NO: 4) and the genomic position is chr21:46823724-46824845.

Note that, as presented in the below-described Test Examples, in the COL18A1-ASx, expression of a region of from the 170th to the 746th of SEQ ID NO: 2, a region of from the 545th to the 1,121st of SEQ ID NO: 3, or a region of from the 230th to the 806th of SEQ ID NO: 4 was confirmed in RNA sequence.

Therefore, the above non-coding RNA may be non-coding RNA containing a part of the base sequences set forth in SEQ ID NOs: 2 to 4; i.e., the region of from the 170th to the 746th of SEQ ID NO: 2, the region of from the 545th to the 1,121st of SEQ ID NO: 3, or the region of from the 230th to the 806th of SEQ ID NO: 4.

In the present invention, the non-coding RNA containing a base sequence set forth in any one of SEQ ID NOs: 1 to 4, a part of the base sequence, or both of the base sequence and the part is a target of the double-stranded nucleic acid molecule, and its expression is suppressed by the double-stranded nucleic acid molecule. Therefore, in the present specification, the above non-coding RNA may be referred to as "target RNA" of the double-stranded nucleic acid molecule.

The non-coding RNA containing a base sequence set forth in any one of SEQ ID NOs: 1 to 4, a part of the base sequence, or both of the base sequence and the part may be non-coding RNA consisting of a base sequence set forth in any one of SEQ ID NOs: 1 to 4, a part of the base sequence, or both of the base sequence and the part.

<Sense Strand and Antisense Strand>

The present inventors conducted extensive studies and have found that remarkably excellent suppressive effects on the expression of the non-coding RNA are exhibited by the double-stranded nucleic acid molecule that contains an antisense strand having a nucleotide sequence complementary to a certain specific target sequence (any one of SEQ ID NOs.: 5 to 11 and 26 to 31) in the non-coding RNA sequences containing a base sequence set forth in any one of SEQ ID NOs: 1 to 4, a part of the base sequence, or both of the base sequence and the part. Thus, the double-stranded nucleic acid molecule of the present invention includes (a) a sense strand containing a nucleotide sequence corresponding to a target sequence set forth in any one of SEQ ID NOs: 5 to 11 and 26 to 31 and (b) an antisense strand containing a nucleotide sequence which is complementary to the sense strand in the (a) to form a double strand with the sense strand.

Here, the sense strand and the antisense strand may be an RNA strand or an RNA-DNA chimera strand. The sense strand and the antisense strand can be hybridized with each other to form the double-stranded nucleic acid molecule.

Note that, among the sequences set forth in SEQ ID NOs: 5 to 11 and 26 to 31, those set forth in SEQ ID NOs: 5 to 11 are parts of the TMPO-AS1 and those set forth in SEQ ID NOs: 26 to 31 are parts of the COL18A1-ASx.

In the above double-stranded nucleic acid molecules, the sense strand is preferably a sense strand containing a nucleotide sequence corresponding to a target sequence set forth in any one of SEQ ID NOs: 5, 6, 9, 10, 27, 28, 29, 30, and 31, more preferably a sense strand containing a nucleotide sequence corresponding to a target sequence set forth in any one of SEQ ID NOs: 6 and 28.

When the sense strand is the above preferable sense strand, the suppressive effects on the expression of the target RNA become stronger even when the double-stranded nucleic acid molecule is used in a small amount, which is advantageous.

Note that, the sense strand in the above double-stranded nucleic acid molecule may contain any other nucleotide sequence so long as the sense strand contains a nucleotide sequence corresponding to the target sequence set forth in the above predetermined SEQ ID NO. The sense strand preferably consists of a nucleotide sequence corresponding to the target sequence set forth in the above predetermined SEQ ID NO.

Also, the antisense strand in the above double-stranded nucleic acid molecule may contain any other nucleotide sequence so long as the antisense strand contains a complementary nucleotide sequence to such an extent that can be hybridized with the sense strand. The antisense strand preferably contains 70% or more of the nucleotide sequence complementary to the sense strand, more preferably 80% or more thereof, particularly preferably 90% or more thereof.

<Kind>

The kind of the double-stranded nucleic acid molecule is not particularly limited and may be appropriately selected depending on the intended purpose. Examples thereof include double-stranded RNAs (dsRNAs) and double-stranded RNA-DNA chimeras. Among them, double-stranded RNAs are preferable.

Here, the phrase "double-stranded RNA" refers to a double-stranded nucleic acid molecule whose sense and antisense strands are both an RNA sequence. The phrase "double-stranded RNA-DNA chimera" refers to a double-stranded nucleic acid molecule whose sense and antisense strands are both an RNA-DNA chimera sequence.

The double-stranded RNA is particularly preferably small interfering RNA (siRNA). Here, siRNA is small-molecule double-stranded RNA with a base length of 18 to 29, and has the function of cleaving the target RNA with a sequence complementary to the antisense strand (guide strand) of the siRNA and suppressing the expression of the target RNA.

The end structure of the siRNA is not particularly limited, so long as the siRNA has the above-described sense and antisense strands and can suppress the expression of the target RNA, and may be appropriately selected depending on the intended purpose. For example, the siRNA may have a blunt end or a cohesive end (overhang). In particular, each strand of the siRNA preferably has an end structure with 2 to 6 overhanging bases at its 3' end, more preferably has an end structure with 2 overhanging bases at its 3' end.

Specific examples of the siRNA include siRNA consisting of SEQ ID NO: 12 and SEQ ID NO: 13, siRNA consisting of SEQ ID NO: 14 and SEQ ID NO: 15, siRNA consisting of SEQ ID NO: 16 and SEQ ID NO: 17, siRNA consisting of SEQ ID NO: 18 and SEQ ID NO: 19, siRNA consisting of SEQ ID NO: 20 and SEQ ID NO: 21, siRNA consisting of SEQ ID NO: 22 and SEQ ID NO: 23, siRNA consisting of SEQ ID NO: 24 and SEQ ID NO: 25, siRNA consisting of SEQ ID NO: 32 and SEQ ID NO: 33, siRNA consisting of SEQ ID NO: 34 and SEQ ID NO: 35, siRNA consisting of SEQ ID NO: 36 and SEQ ID NO: 37, siRNA consisting of SEQ ID NO: 38 and SEQ ID NO: 39, siRNA consisting of SEQ ID NO: 40 and SEQ ID NO: 41, and siRNA consisting of SEQ ID NO: 42 and SEQ ID NO: 43.

Among them, siRNA consisting of SEQ ID NO: 12 and SEQ ID NO: 13, siRNA consisting of SEQ ID NO: 14 and SEQ ID NO: 15, siRNA consisting of SEQ ID NO: 20 and SEQ ID NO: 21, siRNA consisting of SEQ ID NO: 22 and SEQ ID NO: 23, siRNA consisting of SEQ ID NO: 34 and SEQ ID NO: 35, siRNA consisting of SEQ ID NO: 36 and SEQ ID NO: 37, siRNA consisting of SEQ ID NO: 38 and SEQ ID NO: 39, siRNA consisting of SEQ ID NO: 40 and SEQ ID NO: 41, and siRNA consisting of SEQ ID NO: 42 and SEQ ID NO: 43 are preferable, and siRNA consisting of SEQ ID NO: 14 and SEQ ID NO: 15 and siRNA consisting of SEQ ID NO: 36 and SEQ ID NO: 37 are more preferable.

Also, the double-stranded RNA may be short hairpin RNA (shRNA). Here, the shRNA is single-stranded RNA which contains a dsRNA region of about 18 bases to about 29 bases and a loop region of about 3 bases to about 9 bases. After expression in vivo, base pairs are formed to become hairpin-shaped double-stranded RNA (shRNA). Thereafter, the shRNA is cleaved by Dicer (RNase III enzyme) to be siRNA, and the thus-formed siRNA can suppress the expression of the target RNA.

Similar to the siRNA, the end structure of the shRNA is not particularly limited and may be appropriately selected depending on the intended purpose. For example, the shRNA may have a blunt end or a cohesive end (overhang).

Also, the double-stranded RNA-DNA chimera is particularly preferably chimeric siRNA. Here, the chimeric siRNA refers to small-molecule double-stranded RNA-DNA chimera with a base length of 18 to 29 in which a part of the RNA sequence of the siRNA has been converted to DNA. In particular, the chimeric siRNA is preferably small-molecule double-stranded RNA-DNA chimera with a base length of 21 to 23 in which 8 bases at the 3' end of the sense strand of the siRNA and 6 bases at the 5' end of the antisense strand have been converted to DNA. Similar to the siRNA, the chimeric siRNA has a function of suppressing the expression of the target RNA. Note that, the chimeric siRNA encompasses an aspect where a part of the sequence converted to DNA has been converted again to RNA.

Similar to the siRNA, the end structure of the siRNA is not particularly limited and may be appropriately selected depending on the intended purpose. For example, the siRNA may have a blunt end or a cohesive end (overhang).

The chimeric siRNA (double-stranded RNA-DNA chimera) is advantageous because of, for example, high stability in blood, low immune response induction, and low production cost.

<Modification>

Also, the double-stranded nucleic acid molecule may be appropriately modified depending on the intended purpose. The double-stranded nucleic acid molecule may be subjected to 2'O-methylation, phosphorothioate modification (S-modification), Locked Nucleic Acid (LNA) modification, etc., in order for the double-stranded nucleic acid molecule to have, for example, resistance to a nucleolytic enzyme (nuclease) and improved stability in culture or in vivo. Further, for example, in order for the double-stranded nucleic acid molecule to be increased in transfection efficiency into cells, the 5' or 3' end of the sense strand of the double-stranded nucleic acid molecule may be modified with, for example, nanoparticles, cholesterol, or a peptide allowing it to pass through a cell membrane. Note that, such modification of the double-stranded nucleic acid molecule may be appropriately performed by a conventionally known method without any restriction.

<Production Method>

The production method for the double-stranded nucleic acid molecule is not particularly limited and may be a conventionally known production method.

For example, the siRNA can be produced as follows. Specifically, 18- to 29-base single-stranded RNA fragments, each serving as a desired sense strand and an antisense strand complementary thereto, are chemically synthesized using, for example, an existing DNA/RNA auto-synthesizer; and then the thus-synthesized fragments are annealed. Also, an annealed double-stranded siRNA is commercially available. Furthermore, one can request the synthesis of the siRNA to siRNA-synthesizing companies. Moreover, when a desired siRNA expression vector like the below-described vector of the present invention is constructed and introduced into cells, the siRNA can be produced utilizing intracellular reactions.

Also, the chimeric siRNA can be produced by, for example, separately and chemically synthesizing a sense strand and an antisense strand which are chimeric nucleic acid molecules, and then annealing them.

(DNA and Vector)

DNA of the present invention contains a nucleotide sequence which encodes the double-stranded nucleic acid molecule of the present invention. Also, a vector of the present invention contains the above DNA.

<DNA>

The DNA is not particularly limited, so long as it contains a nucleotide sequence encoding the above-described double-stranded nucleic acid molecule of the present invention, and may be appropriately selected depending on the intended purpose. Preferably, a promoter sequence, which is for controlling the transcription of the double-stranded nucleic acid molecule, is linked upstream (5' side) of the nucleotide sequence encoding the double-stranded nucleic acid molecule. The promoter sequence is not particularly limited and may be appropriately selected depending on the intended purpose. Examples thereof include pol II promoters (e.g., a CMV promoter) and pol III promoters (e.g., an H1 promoter and a U6 promoter).

In addition, a terminator sequence, which is for terminating the transcription of the double-stranded nucleic acid molecule, is preferably linked downstream (3' side) of the nucleotide sequence encoding the double-stranded nucleic acid molecule. Similarly, the terminator sequence is not particularly limited and may be appropriately selected depending on the intended purpose.

One preferable aspect of the above DNA is a transcriptional unit containing a promoter sequence, a nucleotide sequence encoding the double-stranded nucleic acid molecule, and a terminator sequence. Note that, the transcriptional unit can be constructed by a conventionally known method.

<Vector>

The vector is not particularly limited and may be appropriately selected depending on the intended purpose so long as it contains the above DNA. Examples of thereof include a plasmid vector and a virus vector. Also, the vector is preferably an expression vector capable of expressing the double-stranded nucleic acid molecule.

The manner in which the double-stranded nucleic acid molecule is expressed is not particularly limited and may be appropriately selected depending on the intended purpose. Examples of the method for expressing siRNA as a double-stranded nucleic acid molecule include a method in which two short single-stranded RNAs are expressed in a tandem manner (tandem type) and a method in which one single-stranded RNA is expressed as shRNA (hairpin type).

The tandem-type siRNA expression vector has DNA which contains a DNA sequence encoding the siRNA's sense strand and that encoding the siRNA's antisense strand, each of the DNA sequences having a promoter sequence linked upstream (5' side) thereof and a terminator sequence linked downstream (3' side) thereof.

The hairpin-type siRNA expression vector has DNA which contains a DNA sequence encoding the siRNA's sense strand and that encoding the siRNA's antisense strand, wherein the sense strand's DNA sequence and the antisense strand's DNA sequence are disposed in an opposite direction to each other and linked via a loop sequence to each other. Here, each of the DNA sequences has a promoter sequence linked upstream (5' side) thereof and a terminator sequence linked downstream (3' side) thereof.

The above vectors can be constructed by a conventionally known method. For example, a vector is cut in advance with a restriction enzyme, and then the DNA is ligated to the cut sites thereof.

When the DNA or vector is introduced (transfected) into cells, the promoters are activated, whereby the double-stranded nucleic acid molecule can be produced. For example, in the case of the tandem-type vector, the DNA is transcribed in cells to form sense and antisense strands, which are then hybridized with each other to produce siRNA. In the case of the hairpin-type vector, the DNA is transcribed in cells to form hairpin-type RNA (shRNA), which then undergoes processing by a dicer to produce siRNA.

(Cancer Cell Proliferation Suppressant)

A cancer cell proliferation suppressant of the present invention is a cancer cell proliferation suppressant (hereinafter may be referred to as "tumor growth suppressant") which suppresses the proliferation of cancer cells. The cancer cell proliferation suppressant contains at least one of the double-stranded nucleic acid molecule, the DNA, and the vector of the present invention; and, if necessary, further contains other ingredients.

<Double-Stranded Nucleic Acid Molecule, DNA, and Vector>

Details of the double-stranded nucleic acid molecule are as described in the section of the above double-stranded nucleic acid molecule of the present invention. The double-stranded nucleic acid molecule can effectively suppress the expression of at least one of the above non-coding RNA and thus is suitably used as an active ingredient of the cancer cell proliferation suppressant which is for suppressing the proliferation of cancer cells. Similarly, details of the DNA and the vector are as described in the sections of the above DNA and the above vector of the present invention.

The amount of at least one of the double-stranded nucleic acid molecule, the DNA, and the vector contained in the cancer cell proliferation suppressant is not particularly limited and may be appropriately determined depending on the intended purpose. Also, the cancer cell proliferation suppressant may be at least one of the double-stranded nucleic acid molecule itself, the DNA itself, and the vector itself.

<Other Ingredients>

The other ingredients are not particularly limited and may be appropriately selected depending on the intended purpose. Examples thereof include; diluents (e.g., physiological saline and culture) which dilute at least one of the double-stranded nucleic acid molecule, the DNA, and the vector to a desired concentration; and transfection reagents which are for introducing (transfecting) at least one of the double-stranded nucleic acid molecule, the DNA, and the vector into cells of interest.

The amount of the other ingredients contained in the cancer cell proliferation suppressant is not particularly limited and may be appropriately determined depending on the intended purpose.

<Cancer Cells>

The cancer cells to which the cancer cell proliferation suppressant is applied are not particularly limited and may be appropriately determined depending on the intended purpose. Examples thereof include breast cancer cells, endometrial cancer cells, cervical cancer cells, prostate cancer cells, liver cancer cells, bladder cancer cells, osteosarcoma cells, and rhabdomyosarcoma cells. Among them, breast cancer cells are preferable and hormone therapy-resistant breast cancer cells are more preferable.

The above cancer cells may be cells cultured in vitro or cells present in the body of patients suffering from cancer.

These cells are available from ATCC (American Type Culture Collection) or JCRB cell bank.

<Actions>

The above cancer cell proliferation suppressant can be allowed to act on cancer cells by introducing (transfecting) it into the above cells. The method for introducing it into the cells is not particularly limited and may be appropriately selected from conventionally known methods depending on the intended purpose. Examples thereof include a method using transfection reagents, a method based on electroporation, a method using magnetic particles, and a method utilizing viral infection.

The amount of the cancer cell proliferation suppressant which is allowed to act on cancer cells is not particularly limited and may be appropriately determined in consideration of, for example, the kind of cells and the intended degree of the effects. For example, the amount is preferably about 0.1 μg (as reduced to the amount of an active ingredient (the above double-stranded nucleic acid molecule)), more preferably about 5 μg, particularly preferably about 15 μg, with respect to $1 \times 10^6$ cells.

<Method for Suppressing Cancer Cell Proliferation>

The cancer cell proliferation suppressant contains at least one of the double-stranded nucleic acid molecule, the DNA, and the vector and thus, when allowed to act on cancer cells, the cancer cell proliferation suppressant can effectively suppress the proliferation of cancer cells via suppression of the expression of at least one of the above non-coding RNA. Therefore, the present invention also relates to a method for suppressing proliferation of cancer cells (hereinafter may be referred to as "method for suppressing tumor growth") the method including allowing at least one of the double-stranded nucleic acid molecule, the DNA, and the vector to act on cancer cells. The cancer cells are not particularly limited and may be appropriately determined depending on the intended purpose. Examples thereof include breast cancer cells, endometrial cancer cells, cervical cancer cells, prostate cancer cells, liver cancer cells, bladder cancer cells, osteosarcoma cells, and rhabdomyosarcoma cells. Among them, breast cancer cells are preferable and hormone therapy-resistant breast cancer cells are more preferable.

(Cancer Cell Movement Suppressant)

A cancer cell movement suppressant of the present invention is a cancer cell movement suppressant for suppressing movements of cancer cells (hereinafter may be referred to as "cancer cell migration suppressant") and contains at least one of the above double-stranded nucleic acid molecule, the above DNA, and the above vector of the present invention; and if necessary, further contains other ingredients.

<Double-Stranded Nucleic Acid Molecule, DNA, and Vector>

Details of the double-stranded nucleic acid molecule are as described in the section of the above double-stranded nucleic acid molecule of the present invention. The double-stranded nucleic acid molecule can effectively suppress the expression of at least one of the target non-coding RNA and is suitable as an active ingredient of the cancer cell movement suppressant for suppressing movements of cancer cells. Also, details of the DNA and the vector are as described in the sections of the above DNA and the above vector of the present invention.

The amount of at least one of the double-stranded nucleic acid molecule, the DNA, and the vector contained in the cancer cell movement suppressant is not particularly limited and may be appropriately determined depending on the intended purpose. Also, the cancer cell movement suppressant may be at least one of the double-stranded nucleic acid molecule itself, the DNA itself, or the vector itself.

<Other Ingredients>

The other ingredients are not particularly limited and may be appropriately selected depending on the intended purpose. Examples thereof include; diluents (e.g., physiological saline and culture) which dilute at least one of the double-stranded nucleic acid molecule, the DNA, and the vector to a desired concentration; and transfection reagents which are for introducing (transfecting) at least one of the double-stranded nucleic acid molecule, the DNA, and the vector into cells of interest.

The amount of the other ingredients contained in the cancer cell movement suppressant is not particularly limited and may be appropriately determined depending on the intended purpose.

<Cancer Cells>

The cancer cells to which the cancer cell proliferation suppressant is applied are not particularly limited and may be appropriately determined depending on the intended purpose. Examples thereof include breast cancer cells, endometrial cancer cells, cervical cancer cells, prostate cancer cells, liver cancer cells, bladder cancer cells, osteosarcoma cells, and rhabdomyosarcoma cells. Among them, breast cancer cells are preferable and hormone therapy-resistant breast cancer cells are more preferable.

The above cancer cells may be cells cultured in vitro or cells present in the body of patients suffering from cancer.

These cells are available from ATCC (American Type Culture Collection) or JCRB cell bank.

<Action>

The above cancer cell proliferation suppressant can be allowed to act on cancer cells by introducing (transfecting) it into the above cells. The method for introducing it into the cells is not particularly limited and may be appropriately selected from conventionally known methods depending on the intended purpose. Examples thereof include a method using transfection reagents, a method based on electroporation, a method using magnetic particles, and a method utilizing viral infection.

The amount of the cancer cell movement suppressant which is allowed to act on cancer cells is not particularly limited and may be appropriately determined in consideration of, for example, the kind of cells and the intended degree of the effects. For example, the amount is preferably about 0.1 µg (as reduced to the amount of an active ingredient (the above double-stranded nucleic acid molecule)), more preferably about 5 µg, particularly preferably about 15 µg, with respect to $1 \times 10^6$ cells.

<Method for Suppressing Cancer Cell Movement>

The cancer cell movement suppressant contains at least one of the double-stranded nucleic acid molecule, the DNA, and the vector and thus, when allowed to act on cancer cells, the cancer cell movement suppressant can effectively suppress the movement of cancer cells via suppression of the expression of at least one of the above non-coding RNA. Therefore, the present invention also relates to a method for suppressing movements of cancer cells, the method including allowing at least one of the double-stranded nucleic acid molecule, the DNA, and the vector to act on cancer cells. The cancer cells are not particularly limited and may be appropriately determined depending on the intended purpose. Examples thereof include breast cancer cells, endometrial cancer cells, cervical cancer cells, prostate cancer cells, liver cancer cells, bladder cancer cells, osteosarcoma cells, and rhabdomyosarcoma cells. Among them, breast cancer cells are preferable and hormone therapy-resistant breast cancer cells are more preferable.

(Drug)

A drug of the present invention is a drug for preventing or treating cancer and contains at least one of the above-described cancer cell proliferation suppressant and the above-described cancer cell movement suppressant of the present invention; and, if necessary, further contains other ingredients.

<At Least One of the Cancer Cell Proliferation Suppressant and the Cancer Cell Movement Suppressant>

Details of the cancer cell proliferation suppressant and the cancer cell movement suppressant are as described in the sections of the above cancer cell proliferation suppressant and the above cancer cell movement suppressant of the present invention.

The cancer cell proliferation suppressant contains at least one of the above-described double-stranded nucleic acid molecule, the above-described DNA, and the above-described vector of the present invention and thus can effectively suppress the proliferation of cancer cells via suppression of the expression of at least one of the above target non-coding RNA.

The cancer cell movement suppressant contains at least one of the above-described double-stranded nucleic acid molecule, the above-described DNA, and the above-described vector of the present invention and thus can effectively suppress the movement of cancer cells via suppression of the expression of at least one of the above target non-coding RNA.

That is, the cancer cell proliferation suppressant and the cancer cell movement suppressant are suitable as a drug for preventing or treating cancer. The cancer is not particularly limited and may be appropriately determined depending on the intended purpose. Examples thereof include breast cancer, endometrial cancer, cervical cancer, prostate cancer, liver cancer, bladder cancer, osteosarcoma, and rhabdomyosarcoma. Among them, breast cancer is preferable and hormone therapy-resistant breast cancer is more preferable.

The amount of at least one of the cancer cell proliferation suppressant and the cancer cell movement suppressant contained in the drug is not particularly limited and may be appropriately determined depending on the intended purpose. The drug may be at least one of the cancer cell proliferation suppressant itself and the cancer cell movement suppressant itself.

Here, the double-stranded nucleic acid molecule serving as an active ingredient of the drug may be the double-stranded nucleic acid molecule itself which has undergone no modification. In order to suitably attain intended preventive or therapeutic effects, the double-stranded nucleic acid molecule is preferably treated before use so as to have a form suitable for administration to a living subject.

For example, the double-stranded nucleic acid molecule is preferably modified from the viewpoint of improving stability of the double-stranded nucleic acid molecule in vivo. The modification applicable to the double-stranded nucleic acid molecule is not particularly limited. Examples thereof include 2'O-methylation, phosphorothioate modification (S-modification) and Locked Nucleic Acid (LNA) modification. Further, for example, in order for the double-stranded nucleic acid molecule to be increased in transfection efficiency into cells, the 5' or 3' end of the sense strand of the double-stranded nucleic acid molecule may be modified with, for example, nanoparticles, cholesterol, or a peptide allowing it to pass through a cell membrane. Such modification of the double-stranded nucleic acid molecule may be appropriately performed by a conventionally known method without any restriction.

Moreover, in view that the double-stranded nucleic acid molecule can be increased in transfection efficiency into cells, the double-stranded nucleic acid molecule preferably forms a complex together with liposome, polymer matrix, etc. The method for forming the complex is not particularly limited and may be appropriately selected from conventionally known methods.

<Other Ingredients>

The other ingredients are not particularly limited and may be appropriately selected depending on the intended purpose. Examples thereof include pharmaceutically acceptable carriers. The carriers are not particularly limited and may be appropriately selected depending on, for example, the dosage form thereof. Also, the amount of the other ingredients contained in the drug is not particularly limited and may be appropriately determined depending on the intended purpose.

<Dosage Form>

The dosage form of the drug is not particularly limited and may be appropriately selected depending on, for example, the below-described desired administration method. Examples thereof include oral solid preparations (e.g., tablets, coated tablets, granules, powder, and capsules), oral liquid preparations (e.g., internal liquid preparations, syrups, and elixirs), injections (e.g., solutions, suspensions and solid preparations to be reconstituted upon use), ointments, patches, gel, cream, external powder, spraying agents, and inhalation powder.

The oral solid preparations can be produced through a routine method including adding to the active ingredient an excipient and other optionally used additives such as an integrating agent, a disintegrating agent, a lubricating agent, a coloring agent, and a flavoring agent.

Examples of the excipient include lactose, sucrose, sodium chloride, glucose, starch, calcium carbonate, kaolin, microcrystalline cellulose, and silicic acid. Examples of the integrating agent include water, ethanol, propanol, simple syrup, glucose liquid, starch liquid, gelatin liquid, carboxymethyl cellulose, hydroxypropyl cellulose, hydroxypropyl starch, methyl cellulose, ethyl cellulose, shellac, calcium phosphate, and polyvinylpyrrolidone. Examples of the disintegrating agent include dry starch, sodium alginate, agar powder, sodium hydrogen carbonate, calcium carbonate, sodium lauryl sulfate, monoglyceride stearate, and lactose. Examples of the lubricating agent include purified talc, stearic acid salts, borax and polyethylene glycol. Examples of the coloring agent include titanium oxide and iron oxide. Examples of the flavoring agent include sucrose, bitter orange peel, citric acid, and tartaric acid.

The oral liquid preparations can be produced through a routine method including adding to the active ingredient additives such as a flavoring agent, a buffer, and a stabilizer.

Examples of the flavoring agent include sucrose, bitter orange peel, citric acid, and tartaric acid. Examples of the buffer include sodium citrate. Examples of the stabilizing agent include tragacanth, gum arabic, and gelatin.

The injections can be produced for use in subcutaneous, intramuscular and intravenous administrations through a routine method including adding to the anti-tumor agent additives such as a pH adjuster, a buffer, a stabilizer, a tonicity agent and a topical anesthetic.

Examples of the pH adjuster and buffer include sodium citrate, sodium acetate, and sodium phosphate. Examples of the stabilizer include sodium pyrosulfite, EDTA, thioglycolic acid, and thiolactic acid. Examples of the tonicity agent include sodium chloride and glucose. Examples of the topical anesthetic include procaine hydrochloride and lidocaine hydrochloride.

The ointment can be produced through a routine method including adding to and mixing with the active ingredient a known base, stabilizing agent, moistening agent, preservative, etc.

Examples of the base include liquid paraffin, white petrolatum, bleached beeswax, octyldodecyl alcohol, and paraffin. Examples of the preservative include methyl parahydroxybenzoate, ethyl parahydroxybenzoate, and propyl parahydroxybenzoate.

The patch can be produced through a routine method including applying onto a known support the ointment in the form of cream, gel, paste, etc. Examples of the support include woven or non-woven fabric made of cotton, staple fiber, and chemical fiber; and films and foam sheets of soft vinyl chloride, polyethylene, and polyurethane.

<Administration>

The drug is suitable for the prevention or treatment of cancer. Thus, the drug can be suitably used by administering it to a patient suffering from cancer.

The animal to which the drug is administered is not particularly limited and may be appropriately selected depending on the intended purpose. Examples thereof include human, mouse, rat, bovine, pig, monkey, dog, and cat, with human being particularly preferred.

The administration method for the drug is not particularly limited and may be selected from topical and systemic administrations in consideration of, for example, the dosage form of the drug, the kind of disease, and the conditions of a patient. When the topical administration is selected, the active ingredient (the above double-stranded nucleic acid molecule) of the drug may be injected (administered) directly into a desired site (e.g., a tumor site), for example. The injection can be performed appropriately using conventionally known techniques (e.g., an injection). When the systemic administration (e.g., oral and intraperitoneal administrations, and administration to blood) is selected, preferably, a conventionally known drug delivery technique is appropriately used so that the active ingredient (the above double-stranded nucleic acid molecule) of the drug can be stably and efficiently delivered to a desired site (e.g., a tumor site).

The dosage amount of the drug is not particularly limited and may be appropriately determined depending on, for example, the age and body weight of a patient to which it is to be administered and the intended degree of the effects. For example, the dosage amount is preferably 1 mg to 100 mg as a daily dose for an adult, which are values reduced to the amount of the active ingredient (the above double-stranded nucleic acid molecule).

The number of doses of the drug is not particularly limited and may be appropriately determined depending on, for example, the age and body weight of a patient to which it is to be administered and the intended degree of the effects.

The timing at which the drug is administered is not particularly limited and may be determined depending on the intended purpose. For example, it may be administered for preventive or therapeutic purposes against the disease. In particular, the drug inhibits at least one of the proliferation and the movement of cancer cells to effectively prevent tumor growth caused by at least one of the proliferation and the movement of these cancer cells. Thus, presumably, the drug is desirably administered at an as early stage of the disease as possible.

<Prevention or Treatment Method>

The drug contains at least one of the cancer cell proliferation suppressant and the cancer cell movement suppressant and thus, when administered to a patient suffering from cancer, the drug can effectively suppress at least one of the proliferation and the movement of cancer cells via suppression of the expression of at least one of the above target non-coding RNA, to thereby prevent or treat cancer. Therefore, the present invention also relates to a prevention or treatment method for cancer including administering the drug to an individual. The cancer is not particularly limited and may be appropriately determined depending on the intended purpose. Examples thereof include breast cancer, endometrial cancer, cervical cancer, prostate cancer, liver cancer, bladder cancer, osteosarcoma, and rhabdomyosarcoma. Among them, breast cancer is preferable and hormone therapy-resistant breast cancer is more preferable.

EXAMPLES

The present invention will next be described by way of Test Examples and the like. However, the present invention should not be construed as being limited to these Test Examples and the like.

Preparation Example 1: Cells and Culturing Method

In each of the below-described Test Examples, the following cells were used. These cells were obtained from ATCC or JCRB cell bank.

<Cells>
MCF-7 cells (human breast cancer cells)
MDA-MB-231 cells (human breast cancer cells)
T47D cells (human breast cancer cells)
Ishikawa cells (human endometrial cancer cells)
HHUA cells (human endometrial cancer cells)
Hec1A cells (human endometrial cancer cells)
HeLa cells (human cervical cancer cells)
LNCaP cells (human prostate cancer cells)
VCaP cells (human prostate cancer cells)
22Rv1 cells (human prostate cancer cells)
DU145 cells (human prostate cancer cells)
PC3 cells (human prostate cancer cells)
HepG2 cells (human liver cancer cells)
EJ cells (human bladder cancer cells)
T24 cells (human bladder cancer cells)
RT4 cells (human bladder cancer cells)
MG63 cells (human osteosarcoma cells)
SaoS cells (human osteosarcoma cells)
HOS cells (human osteosarcoma cells)
SJCRH30 cells (human rhabdomyosarcoma cells)
RD cells human rhabdomyosarcoma cells)

<Cell Culture>

The above cells were cultured at 37° C. in an incubator containing 5% carbon dioxide gas in air.

A cell culture medium used for MCF-7 cells, T47D cells, Ishikawa cells, HeLa cells, VCaP cells, 22Rv1 cells, HepG2 cells, EJ cells, MG63 cells, SaoS cells, HOS cells, or RD cells was a DMEM medium (product of NACALAI TESQUE CO., LTD.) containing 10% fetal bovine serum (FBS, product of Sigma Co.), 100 μg/mL streptomycin, and 100 U/mL penicillin (product of Invitrogen Co.). A cell culture medium used for MDA-MB-231 cells, LNCaP cells, DU145 cells, PC3 cells, or SJCRH30 cells was a RPMI1640 medium (product of NACALAI TESQUE CO., LTD.) containing 10% fetal bovine serum (FBS, product of Sigma Co.), 100 μg/mL streptomycin, and 100 U/mL penicillin (product of Invitrogen Co.). A cell culture medium used for HHUA cells was a HamF12 medium (product of NACALAI TESQUE CO., LTD.) containing 10% fetal bovine serum (FBS, product of Sigma Co.), 100 μg/mL streptomycin, and 100 U/mL penicillin (product of Invitrogen Co.). A cell culture medium used for Hec1A cells, T24 cells, or RT4 cells was a McCoy's 5A medium (product of LifeTechnologies Co.) containing 10% fetal bovine serum (FBS, product of Sigma Co.), 100 μg/mL streptomycin, and 100 U/mL penicillin (product of Invitrogen Co.).

Preparation Example 2: Clinical Sample of Breast Cancer Tumor Tissue

Clinical samples of breast cancer tumor tissue (BC1 to BC10) were provided by the Breast Oncology Service at the Saitama Medical University International Medical Center. The above samples were taken after obtaining informed consent while keeping in mind, for example, protections of privacy, human rights, and individual benefits. This study has been admitted by the Institutional Review Board of the Saitama Medical University International Medical Center (Request Number: 675).

Test Example 1: Identification of Non-Coding RNA (TMPO-AS1 and COL18A1-ASx)

<RNA Sequence Analysis>

MCF-7 cells were cultured in the following hormone deficient cell culture medium for 1 day and then were stimulated for 4 hours by the addition of any one of the following drugs at the following concentration. Thereafter, ISOGEN (product of NIPPON GENE CO., LTD.) was used to recover total RNA from the above cells.
—Hormone Deficient Cell Culture Medium—
Phenol red-free DMEM medium (product of Sigma Co.) containing 10% fetal bovine serum (dccFBS) having undergone hormone removal by the charcoal/dextran treatment (product of Sigma Co.), 100 μg/mL streptomycin, and 100 U/mL penicillin (product of Invitrogen Co.)
—Drugs—
(1) 17β-Estradiol (hereinafter may be referred to as "E2"): 100 nM
(2) 4-Hydroxytamoxifen (hereinafter may be referred to as "OHT"): 1 μM
(3) Ethanol (hereinafter may be referred to as "solvent control"): final concentration 0.1%

The obtained RNA was subjected to RNA sequence analysis by preparing a library using GAIIx (product of Illumina Co., Ltd.) which is a next generation sequencer.

The obtained sequence information was mapped on a RefSeq database (NCBI Reference Sequence database) to select about 2,000 transcripts of non-coding RNA data (RefSeq Gene NR Series) in which the tag count is 50 or more in any of the samples and which are located in the vicinity (within 5 kb) of the database of the previously-reported estrogen receptor α (ERα) binding site (hereinafter may be referred to as "ERBS", Carroll J S et al., Nature Genetics. 38, 1289-97, 2006).

Out of the above non-coding RNA, about 300 transcripts excluding non-coding RNA variant genes of short RNA and coding genes were selected.

Out of about 300 transcripts, TMPO-AS1 was selected which is one long non-coding RNA exhibiting an expression increased by E2 twice or more the solvent control and is considered as an antisense transcript of the TMPO (thymopoietin) gene.

Also, as one of the group of about 300 transcripts, there is COL18A1-AS2 which is an antisense transcript of the COL18A1 gene. In the vicinity of it, a novel non-coding RNA was newly discovered which is located in the antisense direction immediately upstream of the transcription initiation site of COL18A1, is present on ERBS, and exhibits an expression increased by E2. This was named COL18A1-ASx.

For visualization analysis of the sequence, IGV (Integrative Genomics Viewer) browser (Broad Institute) or Genome Explorer (National Institute of Genetics) was utilized.

The above TMPO-AS1 is registered in the above RefSeq database as "*Homo sapiens* TMPO antisense RNA 1 (TMPO-AS1), long non-coding RNA" (NR_027157.1;gi 224548948), where the RNA length is 3,161 bp (see SEQ ID NO: 1) and the genomic position is chr12:98906751-98910004(hg19).

As for the above COL18A1-ASx, three kinds of variants thereof are registered in the above RefSeq database as "*Homo sapiens* uncharacterized LOC101928745".

The above three kinds of variants are as follows.
(1) LOC101928745, transcript variant X1, ncRNA (XR_254050.1;gi 530438803)
The putative RNA length is 746 bp (see SEQ ID NO: 2) and the genomic position is chr21:46823724-46825332.
Note that, in the above RNA sequence, expression of a region of from the 170th to the 746th of SEQ ID NO: 2 was confirmed.

(2) LOC101928745, transcript variant X2, ncRNA (XR_254051.1;gi 530438804)
The putative RNA length is 1,121 bp (see SEQ ID NO: 3) and the genomic position is chr21:46823724-46826253.
Note that, in the above RNA sequence, expression of a region of from the 545th to the 1,121st of SEQ ID NO: 3 was confirmed.
(3) LOC101928745, transcript variant X3, misc_RNA (XR_254052.1;gi 530438805)
The putative RNA length is 806 bp (see SEQ ID NO: 4) and the genomic position is chr21:46823724-46824845.
Note that, in the above RNA sequence, expression of a region of from the 230th to the 806th of SEQ ID NO: 4 was confirmed.

Test Example 2-1: Expression of TMPO-AS1 in Various Cancer Cells and Breast Cancer Clinical Samples Test Example 2-1-1

MCF-7 cells were cultured in the following hormone deficient cell culture medium for 1 day and then were stimulated for 4 hours by the addition of any one of the following drugs at the following concentration. Thereafter, ISOGEN (product of NIPPON GENE CO., LTD.) was used to recover total RNA from the above cells.
—Hormone Deficient Cell Culture Medium—
Phenol red-free DMEM medium (product of Sigma Co.) containing 10% fetal bovine serum (dccFBS) having undergone hormone removal with a treatment using charcoal/dextran (product of Sigma Co.), 100 μg/mL streptomycin, and 100 U/mL penicillin (product of Invitrogen Co.)
—Drugs—
(1) 17β-Estradiol (hereinafter may be referred to as "E2"): 100 nM
(2) 4-Hydroxytamoxifen (hereinafter may be referred to as "OHT"): 1 μM
(3) Ethanol (hereinafter may be referred to as "solvent control"): final concentration 0.1%

The obtained RNA was analyzed using GAIIx (product of Illumina Co., Ltd.) which is a next generation sequencer. For visualization analysis of the sequence, Genome Explorer was utilized.

FIG. 1A presents analysis results of the expression of TMPO-AS1 in MCF-7 cells. In FIG. 1A, sequentially from the top row, the regions of "Refseq gene (+strand)", "Refseq gene (−strand)", "Refseq mRNA (+strand)", and "Refseq mRNA (−strand)" in the human genome are schematically presented. The lower rows present results of "solvent-treated MCF-7 (+strand)" (MCF-7 Vehicle 4h (+)), "solvent-treated MCF-7 cells (−strand)" (MCF-7 Vehicle 4h (−)), "E2-treated MCF-7 cells (+strand)" (MCF-7 E2 4h (+)), "E2-treated MCF-7 cells (−strand)" (MCF-7 E2 4h (−)), "OHT-treated MCF-7 cells (+strand)" (MCF-7 OHT 4h (+)), and "OHT-treated MCF-7 cells (−strand)" (MCF-7 OHT 4h (−)).

From the results of FIG. 1A, the expression of TMPO-AS1 was suppressed by OHT in MCF-7 cells.

Test Example 2-1-2

Total RNA was recovered from MDA-MB-231 cells, MCF-7 cells, or T47D cells using ISOGEN (product of NIPPON GENE CO., LTD.).

The obtained RNA was analyzed using GAIIx (product of Illumina Co., Ltd.) which is a next generation sequencer. For visualization analysis of the sequence, IGV (Integrative Genomics Viewer) browser was utilized.

Figure 1B:
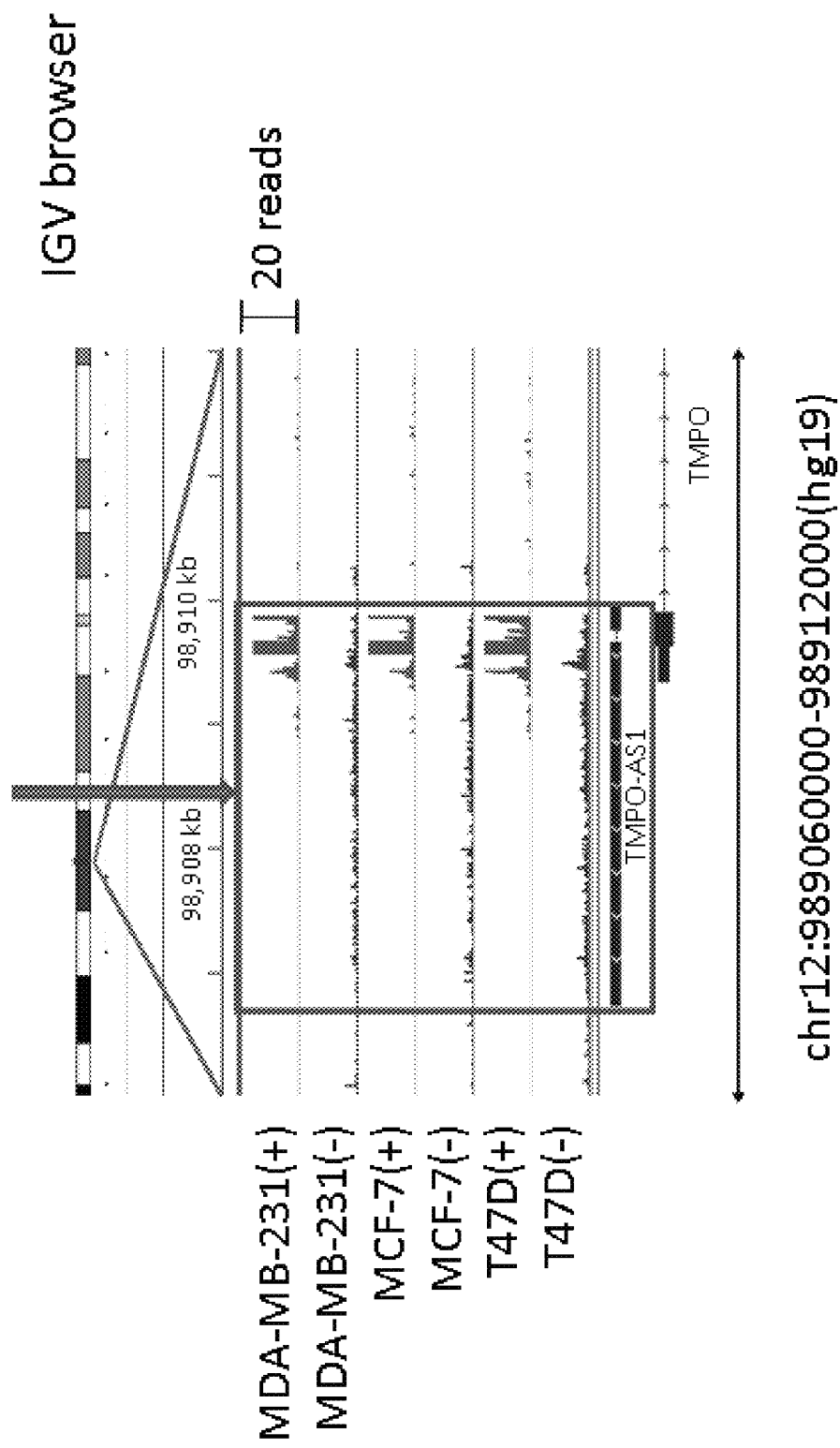
FIG. 1B illustrates analysis results of expression of TMPO-AS1 in Test Example 2-1-2.

FIG. 1B presents analysis results of the expression of TMPO-AS1 in MDA-MB-231 cells, MCF-7 cells, or T47D cells. In FIG. 1B, sequentially from the top row, the results of "MDA-MB-231 (+strand)" (MDA-MB-231(+)), "MDA-MB-231 (−strand)" (MDA-MB-231 (−)), "MCF-7 (+strand)" (MCF-7(+)), "MCF-7 (−strand)" (MCF-7 (−)), "T47D (+strand)" (T47D(+)), and "T47D (−strand)" (T47D (−)) are presented.

Form the results of FIG. 1B, the expression of TMPO-AS1 was confirmed in not only MCF-7 cells but also MDA-MB-231 cells and T47D cells.

Test Example 2-1-3

Total RNA was recovered from Ishikawa cells, HHUA cells, Hec1A cells, LNCaP cells, VCaP cells, 22Rv1 cells, DU145 cells, or PC3 cells using ISOGEN (product of NIPPON GENE CO., LTD.).

Note that, Ishikawa cells were treated with E2 (for 24 hours) and then total RNA was recovered using ISOGEN (product of NIPPON GENE CO., LTD.). 22Rv1 cells were treated with dihydrotestosterone (DHT) (for 24 hours) and then total RNA was recovered using ISOGEN (product of NIPPON GENE CO., LTD.).

The obtained RNA was analyzed using GAIIx (product of Illumina Co., Ltd.) which is a next generation sequencer. For visualization analysis of the sequence, IGV (Integrative Genomics Viewer) browser was utilized.

Figure 1C:
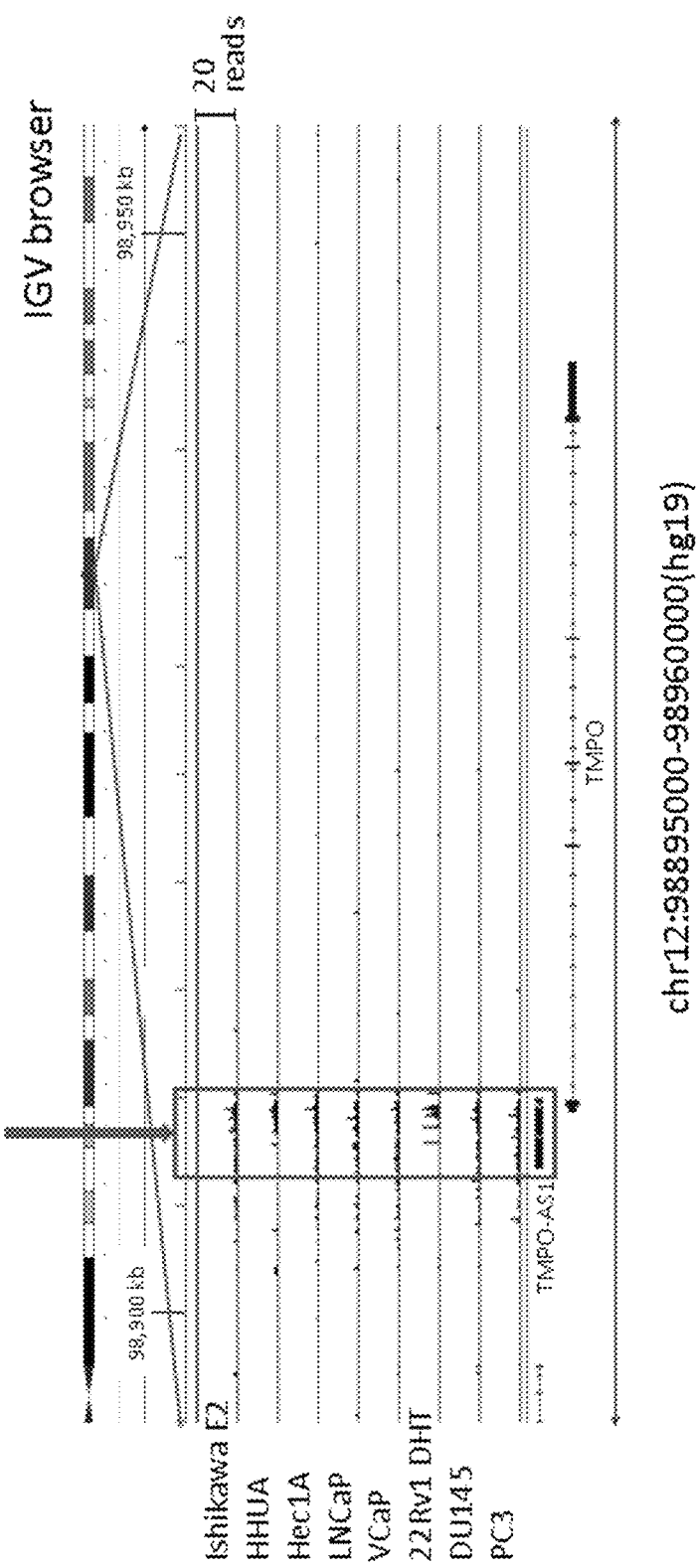
FIG. 1C illustrates analysis results of expression of TMPO-AS1 in Test Example 2-1-3.

FIG. 1C presents analysis results of the expression of TMPO-AS1 in Ishikawa cells, HHUA cells, Hec1A cells, LNCaP cells, VCaP cells, 22Rv1 cells, DU145 cells, or PC3 cells. In FIG. 1C, sequentially from the top row, the results of Ishikawa cells (Ishikawa E2), HHUA cells (HHUA), Hec1A cells (Hec1A), LNCaP cells (LNCaP), VCaP cells (VCaP), 22Rv1 cells (22Rv1 DHT), DU145 cells (DU145), and PC3 cells (PC3) are presented.

From the results of FIG. 1C, the expression of TMPO-AS1 was confirmed also in Ishikawa cells, HHUA cells, and Hec1A cells, which are endometrial cancer cells, and LNCaP, VCaP, 22Rv1, DU145, and PC3, which are prostate cancer cells.

Test Example 2-1-4

Total RNA was recovered from HeLa cells, HepG2 cells, EJ cells, T24 cells, RT4 cells, MG63 cells, SaoS cells, HOS cells, SJCRH30 cells, or RD cells using ISOGEN (product of NIPPON GENE CO., LTD.).

The obtained RNA was analyzed using GAIIx (product of Illumina Co., Ltd.) which is a next generation sequencer. For visualization analysis of the sequence, IGV (Integrative Genomics Viewer) browser was utilized.

Figure 1D:
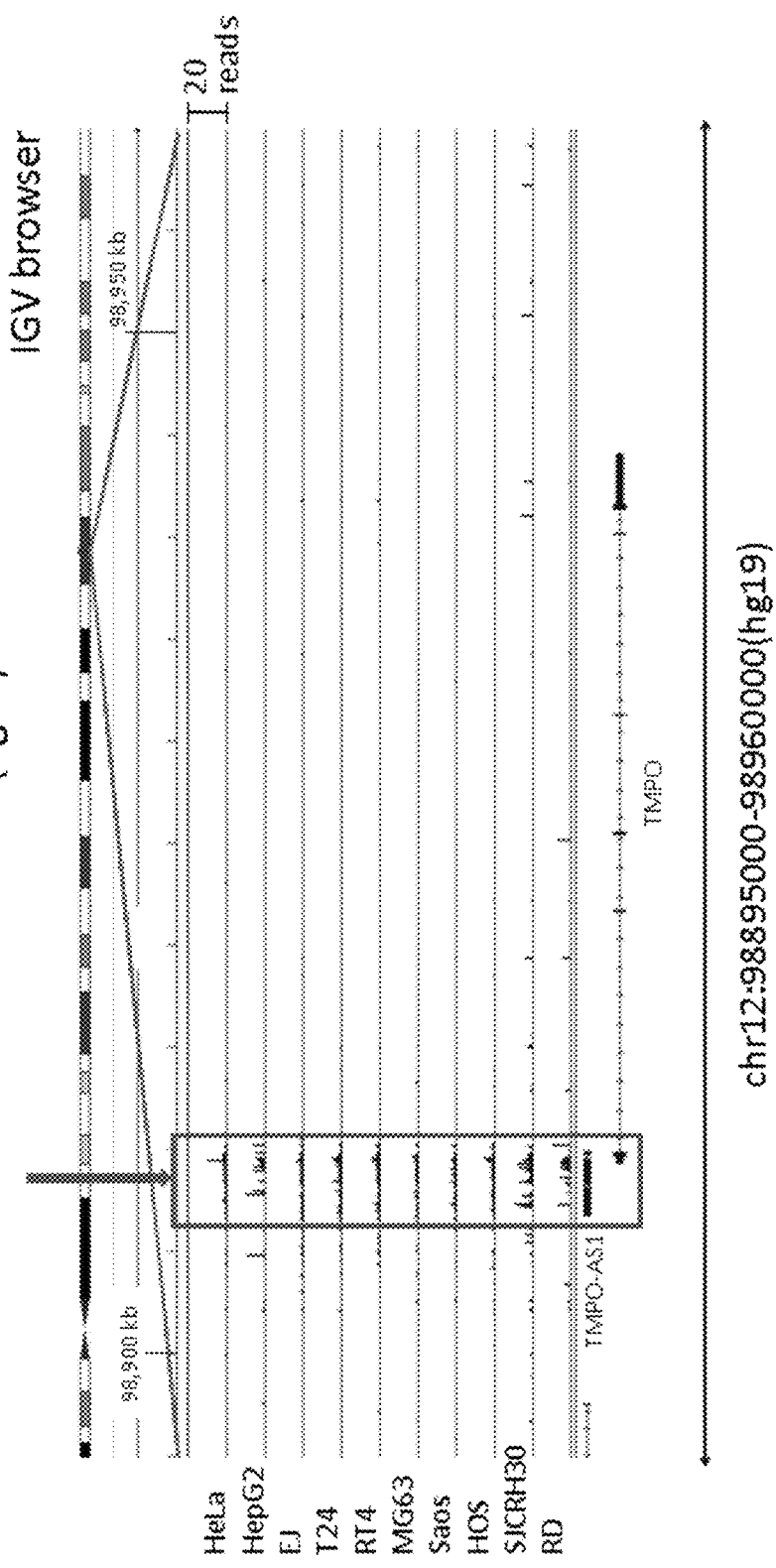
FIG. 1D illustrates analysis results of expression of TMPO-AS1 in Test Example 2-1-4.

FIG. 1D presents analysis results of the expression of TMPO-AS1 in HeLa cells, HepG2 cells, EJ cells, T24 cells, RT4 cells, MG63 cells, SaoS cells, HOS cells, SJCRH30 cells, or RD cells. In FIG. 1D, sequentially from the top row, the results of HeLa cells (HeLa), HepG2 cells (HepG2), EJ cells (EJ), T24 cells (T24), RT4 cells (RT4), MG63 cells (MG63), SaoS cells (SaoS), HOS cells (HOS), SJCRH30 cells (SJCRH30), and RD cells (RD) are presented.

From the results of FIG. 1D, the expression of TMPO-AS1 was confirmed also in HeLa cells, which are cervical cancer cells, HepG2 cells, which are liver cancer cells, EJ cells, T24 cells, and RT4 cells, which are bladder cancer cells, MG63 cells, SaoS cells, and HOS cells, which are osteosarcoma cells, and SJCRH30 cells and RD cells, which are rhabdomyosarcoma cells.

Test Example 2-1-5

Total RNA was recovered from the clinical samples of breast cancer tumor tissue (BC1 to BC10) using ISOGEN (product of NIPPON GENE CO., LTD.).

The obtained RNA was analyzed using GAIIx (product of Illumina Co., Ltd.) which is a next generation sequencer. For visualization analysis of the sequence, IGV (Integrative Genomics Viewer) browser was utilized.

Figure 1E:
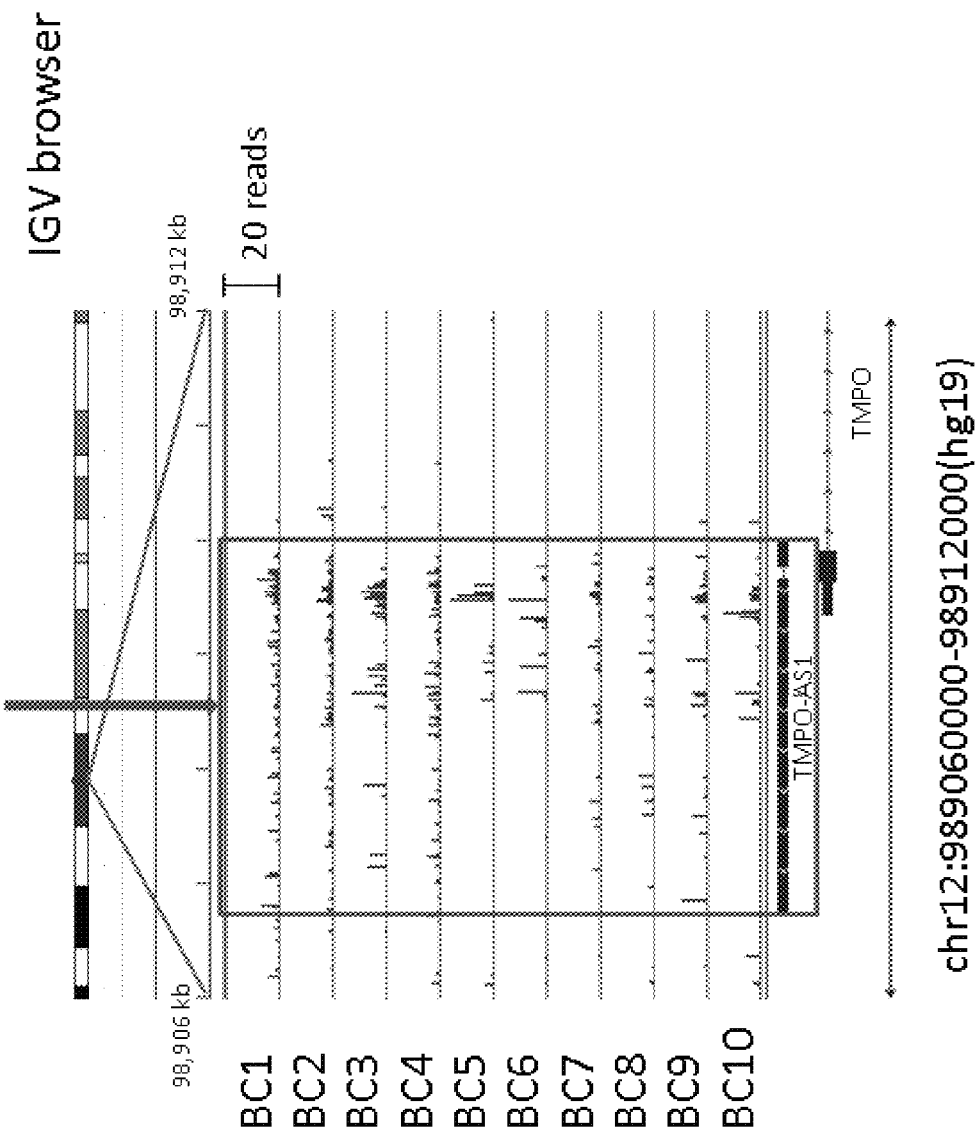
FIG. 1E illustrates analysis results of expression of TMPO-AS1 in Test Example 2-1-5.

FIG. 1E presents analysis results of the expression of TMPO-AS1 in the clinical samples of breast cancer tumor tissue (BC1 to BC10). In FIG. 1E, sequentially from the top row, the results of BC1 to BC10 are presented.

From the results of FIG. 1E, the expression of TMPO-AS1 was confirmed also in the clinical samples of breast cancer tumor tissue.

Test Example 2-2: Expression of COL18A1-ASx in Various Cancer Cells and Breast Cancer Clinical Samples Test Example 2-2-1

MCF-7 cells were cultured in the following hormone deficient cell culture medium for 1 day and then were stimulated for 4 hours by the addition of any one of the following drugs at the following concentration. Thereafter, ISOGEN (product of NIPPON GENE CO., LTD.) was used to recover total RNA from the above cells.

—Hormone Deficient Cell Culture Medium—

Phenol red-free DMEM medium (product of Sigma Co.) containing 10% fetal bovine serum (dccFBS) having undergone hormone removal with a treatment using charcoal/dextran (product of Sigma Co.), 100 µg/mL streptomycin, and 100 U/mL penicillin (product of Invitrogen Co.)

—Drugs—

(1) 17β-Estradiol (hereinafter may be referred to as "E2") 100 nM (2) 4-Hydroxytamoxifen (hereinafter may be referred to as "OHT"): 1 µM (3) Ethanol (hereinafter may be referred to as "solvent control"): final concentration 0.1%

The obtained RNA was analyzed using GAIIx (product of Illumina Co., Ltd.) which is a next generation sequencer. For visualization analysis of the sequence, Genome Explorer was utilized.

Figure 2A:
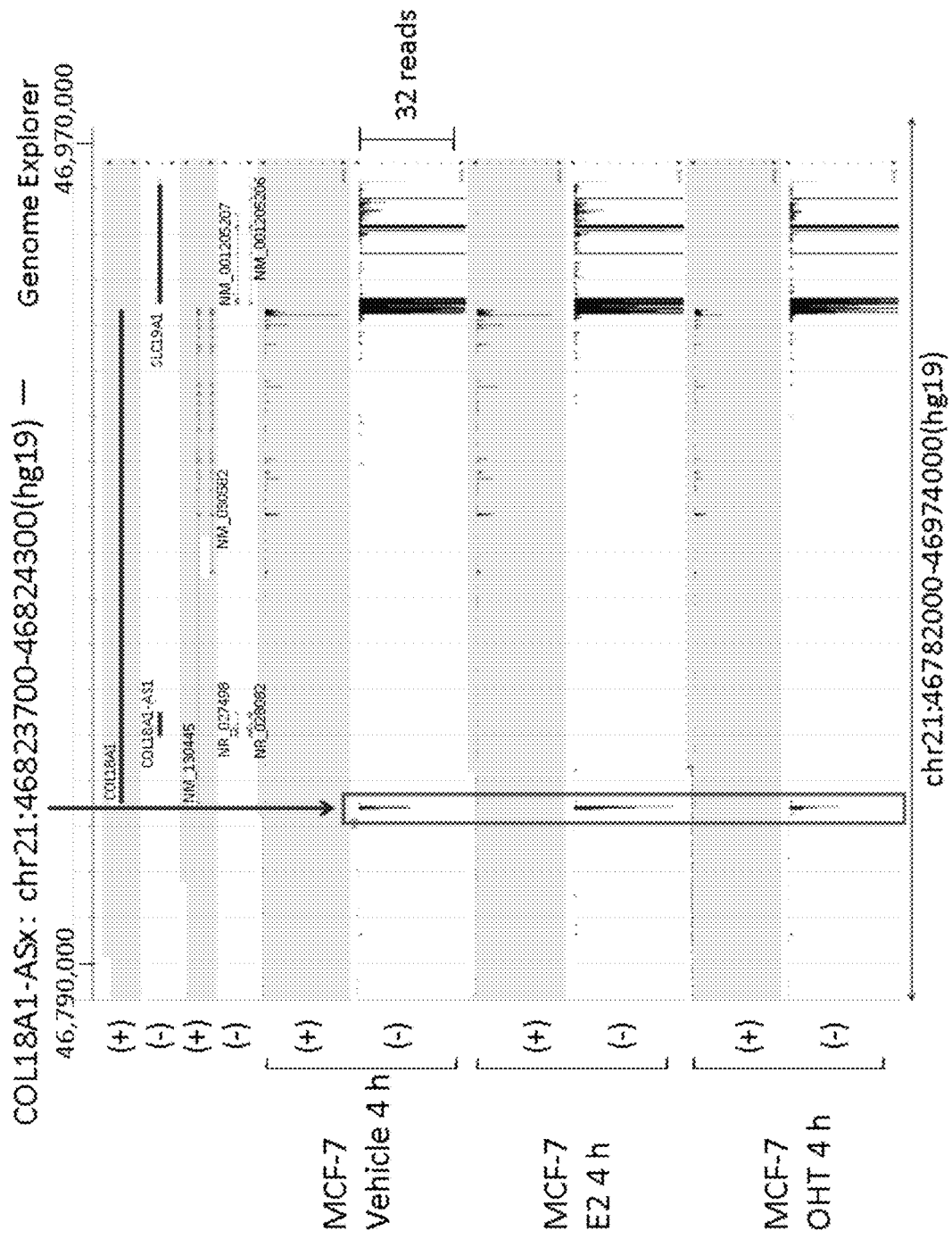
FIG. 2A illustrates analysis results of expression of COL18A1-ASx in Test Example 2-2-1.

FIG. 2A presents analysis results of the expression of COL18A1-ASx in MCF-7 cells. In FIG. 2A, sequentially from the top row, the regions of "Refseq gene (+strand)", "Refseq gene (−strand)", "Refseq mRNA (+strand)", and "Refseq mRNA (−strand)" in the human genome are schematically presented. The lower rows present results of "solvent-treated MCF-7 (+strand)" (MCF-7 Vehicle 4h (+)), "solvent-treated MCF-7 cells (−strand)" (MCF-7 Vehicle 4h (−)), "E2-treated MCF-7 cells (+strand)" (MCF-7 E2 4h (+)), "E2-treated MCF-7 cells (−strand)" (MCF-7 E2 4h (−)), "OHT-treated MCF-7 cells (+strand)" (MCF-7 OHT 4h(+)), and "OHT-treated MCF-7 cells (−strand)" (MCF-7 OHT 4h (−)).

From the results of FIG. 2A, the expression of COL18A1-ASx was induced by estrogen in MCF-7 cells.

Test Example 2-2-2

Total RNA was recovered from MDA-MB-231 cells, MCF-7 cells, or T47D cells using ISOGEN (product of NIPPON GENE CO., LTD.).

The obtained RNA was analyzed using GAIIx (product of Illumina Co., Ltd.) which is a next generation sequencer. For visualization analysis of the sequence, IGV (Integrative Genomics Viewer) browser was utilized.

Figure 2B:
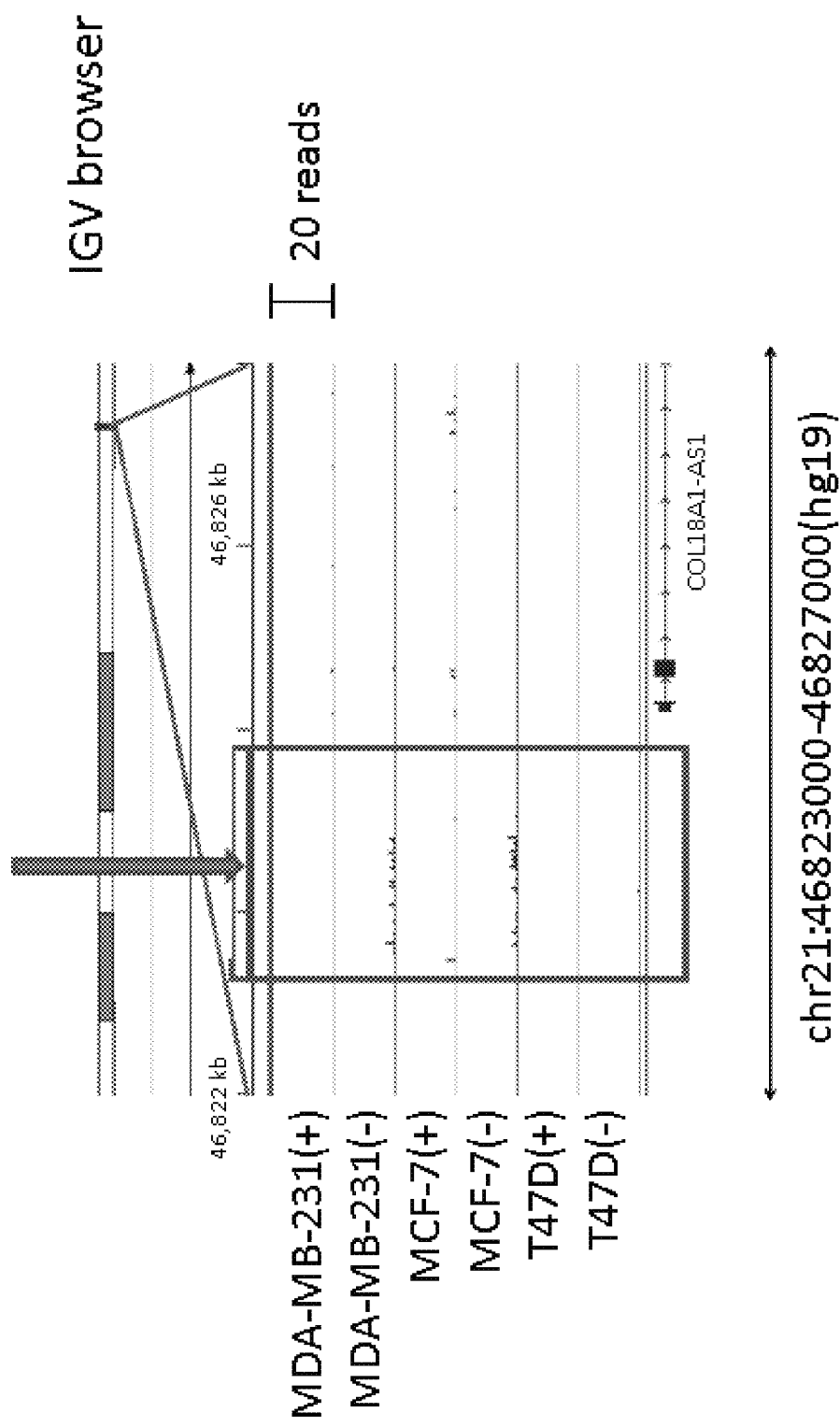
FIG. 2B illustrates analysis results of expression of COL18A1-ASx in Test Example 2-2-2.

FIG. 2B presents analysis results of the expression of COL18A1-ASx in MDA-MB-231 cells, MCF-7 cells, or T47D cells. In FIG. 2B, sequentially from the top row, the results of "MDA-MB-231 (+strand)" (MDA-MB-231(+)), "MDA-MB-231 (−strand)" (MDA-MB-231 (−)), "MCF-7 (+strand)" (MCF-7(+)), "MCF-7 (−strand)" (MCF-7 (−)), "T47D (+strand)" (T47D(+)), and "T47D (−strand)" (T47D (−)) are presented.

From the results of FIG. 2B, the expression of COL18A1-ASx was confirmed also in MDA-MB-231 cells.

Test Example 2-2-3

Total RNA was recovered from Ishikawa cells, HHUA cells, Hec1A cells, LNCaP cells, VCaP cells, 22Rv1 cells, DU145 cells, or PC3 cells using ISOGEN (product of NIPPON GENE CO., LTD.).

Note that, Ishikawa cells were subjected to E2 treatment (for 24 hours) and then total RNA was recovered using ISOGEN (product of NIPPON GENE CO., LTD.). 22Rv1 cells were subjected to DHT treatment (for 24 hours) and then total RNA was recovered using ISOGEN (product of NIPPON GENE CO., LTD.).

The obtained RNA was analyzed using GAIIx (product of Illumina Co., Ltd.) which is a next generation sequencer. For visualization analysis of the sequence, IGV (Integrative Genomics Viewer) browser was utilized.

Figure 2C:
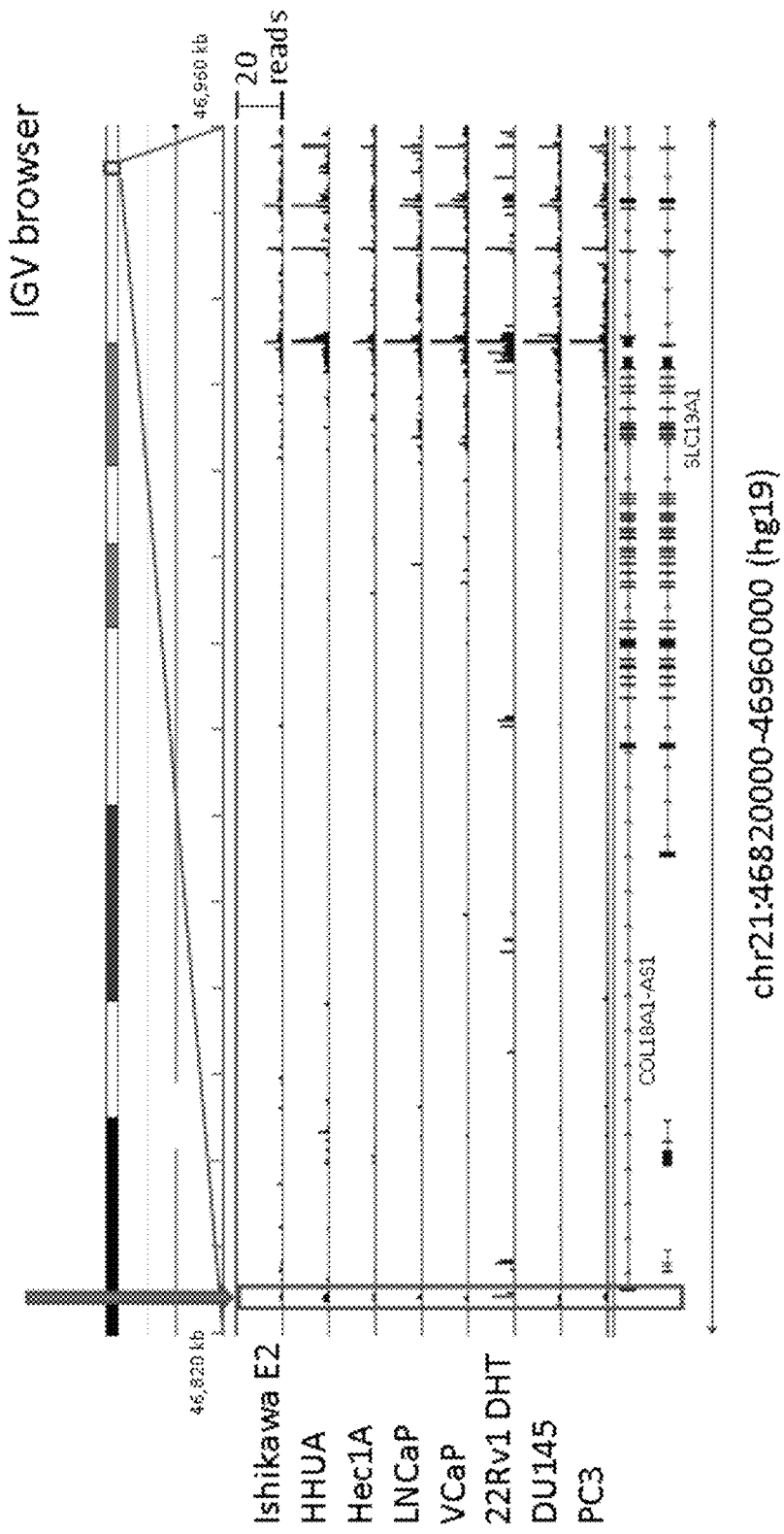
FIG. 2C illustrates analysis results of expression of COL18A1-ASx in Test Example 2-2-3.

FIG. 2C presents analysis results of the expression of COL18A1-ASx in Ishikawa cells, HHUA cells, Hec1A cells, LNCaP cells, VCaP cells, 22Rv1 cells, DU145 cells, or PC3 cells. In FIG. 2C, sequentially from the top row, the results of Ishikawa cells (Ishikawa E2), HHUA cells (HHUA), Hec1A cells (Hec1A), LNCaP cells (LNCaP), VCaP cells (VCaP), 22Rv1 cells (22Rv1 DHT), DU145 cells (DU145), and PC3 cells (PC3) are presented.

From the results of FIG. 2C, the expression of COL18A1-ASx was confirmed also in Ishikawa cells, HHUA cells, and Hec1A cells, which are endometrial cancer cells, and LNCaP, VCaP, 22Rv1, DU145, and PC3, which are prostate cancer cells.

Test Example 2-2-4

Total RNA was recovered from HeLa cells, HepG2 cells, EJ cells, T24 cells, RT4 cells, MG63 cells, SaoS cells, HOS cells, SJCRH30 cells, or RD cells using ISOGEN (product of NIPPON GENE CO., LTD.).

The obtained RNA was analyzed using GAIIx (product of Illumina Co., Ltd.) which is a next generation sequencer. For visualization analysis of the sequence, IGV (Integrative Genomics Viewer) browser was utilized.

Figure 2D:
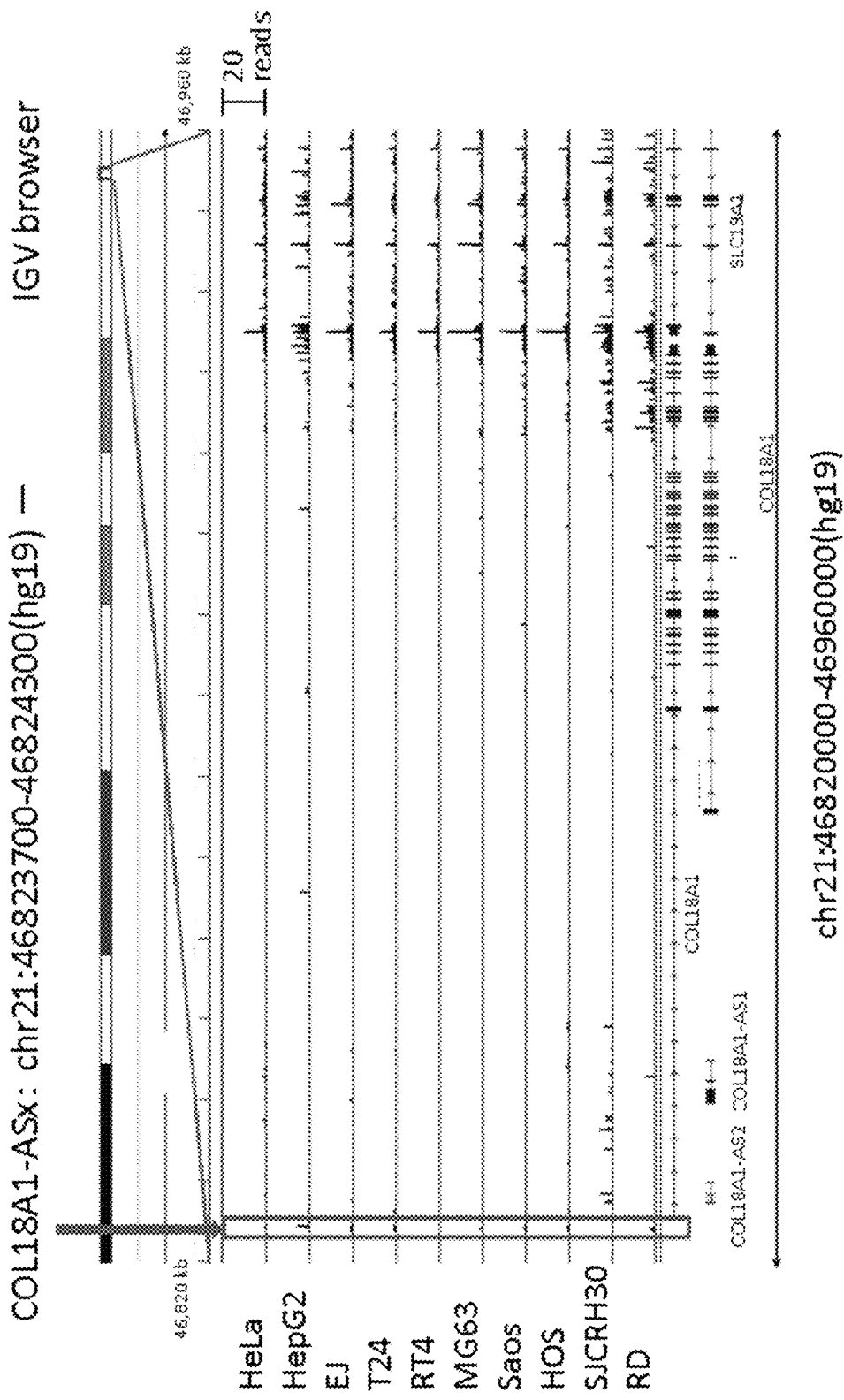
FIG. 2D illustrates analysis results of expression of COL18A1-ASx in Test Example 2-2-4.

FIG. 2D presents analysis results of the expression of COL18A1-ASx in HeLa cells, HepG2 cells, EJ cells, T24 cells, RT4 cells, MG63 cells, SaoS cells, HOS cells, SJCRH30 cells, or RD cells. In FIG. 2D, sequentially from the top row, the results of HeLa cells (HeLa), HepG2 cells (HepG2), EJ cells (EJ), T24 cells (T24), RT4 cells (RT4), MG63 cells (MG63), SaoS cells (SaoS), HOS cells (HOS), SJCRH30 cells (SJCRH30), and RD cells (RD) are presented.

From the results of FIG. 2D, the expression of COL18A1-ASx was confirmed also in HepG2 cells, which are liver cancer cells, EJ cells and T24 cells, which are bladder cancer cells, MG63 cells, SaoS cells, and HOS cells, which are osteosarcoma cells, and RD cells, which are rhabdomyosarcoma cells.

Test Example 2-2-5

Total RNA was recovered from the clinical samples of breast cancer tumor tissue (BC1 to BC10) using ISOGEN (product of NIPPON GENE CO., LTD.).

The obtained RNA was analyzed using GAIIx (product of Illumina Co., Ltd.) which is a next generation sequencer. For visualization analysis of the sequence, IGV (Integrative Genomics Viewer) browser was utilized.

Figure 2E:
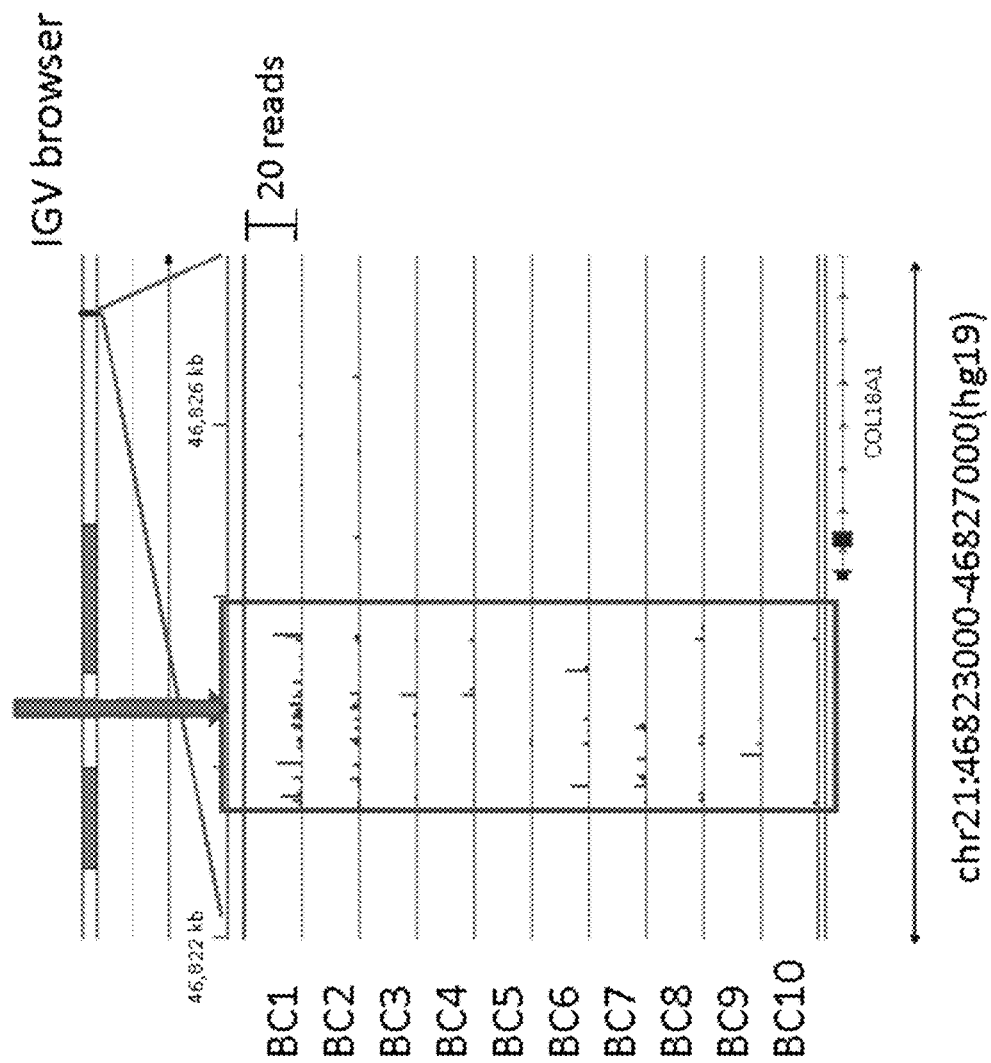
FIG. 2E illustrates analysis results of expression of COL18A1-ASx in Test Example 2-2-5.

FIG. 2E presents analysis results of the expression of COL18A1-ASx in the clinical samples of breast cancer tumor tissue (BC1 to BC10). In FIG. 2E, sequentially from the top row, the results of BC1 to BC10 are presented.

From the results of FIG. 2E, the expression of COL18A1-ASx was confirmed also in the clinical samples of breast cancer tumor tissue.

Production Example 1: Production of Double-Stranded Nucleic Acid Molecule

A double-stranded nucleic acid molecule of the present invention for suppressing expression of non-coding RNA containing a base sequence set forth in any one of SEQ ID NOs: 1 to 4, a part of the base sequence, or both of the base sequence and the part was prepared in the following manner.

Double-stranded nucleic acid molecules, siRNA (siTMPO-AS1-1, 2, 3, 5, 7, 8, 10) of the present invention against non-coding RNA containing a base sequence set forth in SEQ ID NO: 1 and double-stranded nucleic acid molecules (siCOL18A1-ASx-1, 2, 5, 6, 7, 9) of the present invention against non-coding RNA containing a base sequence set forth in any one of SEQ ID NOs: 1 to 4, a part of the base sequence, or both of the base sequence and the part were synthesized as RNA or RNA-DNA chimeric double strands so that target sequences of the double-stranded nucleic acid molecules (described below) and sequences containing portions complementary thereto were overhung by 2 bases at the 3' end (product of Sigma-Aldrich Co.). These can prevent off-target effects derived from the sense strand.

Also, as a negative control, siRNA (siControl (product of RNAi Co.)) having no off-target effect to all of the already known genes was provided.

The sequences of the target sequences of the double-stranded nucleic acid molecules and prepared siRNA or chimeric siRNA are presented below.

```
<siTMPO-AS1-1 (siRNA)>
-Target sequence-
                               (SEQ ID NO: 5)
5'-gaagactagtgacctataatt-3'

-Sequence of siRNA-
--Sense strand--
                               (SEQ ID NO: 12)
5'-gaagacuagugaccuauaauu-3'

--Antisense strand--
                               (SEQ ID NO: 13)
5'-uuauaggucacuagucuuccu-3'
```

Note that, the target sequence set forth in SEQ ID NO: 5 corresponds to the 1,379th to the 1,399th in the base sequence set forth in SEQ ID NO: 1.

```
<siTMPO-AS1-2 (siRNA)>
-Target sequence-
                                  (SEQ ID NO: 6)
5'-gagccgaactacgaaccaact-3'

-Sequence of siRNA-
--Sense strand--
                                  (SEQ ID NO: 14)
5'-gagccgaacuacgaaccaacu-3'

--Antisense strand--
                                  (SEQ ID NO: 15)
5'-uugguucguaguucggcucug-3'
```

Note that, the target sequence set forth in SEQ ID NO: 6 corresponds to the 455th to the 475th in the base sequence set forth in SEQ ID NO: 1.

```
<siTMPO-AS1-3 (siRNA)>
-Target sequence-
                                  (SEQ ID NO: 7)
5'-ggacaggtcgtactgatttg-3'

-Sequence of siRNA-
--Sense strand--
                                  (SEQ ID NO: 16)
5'-ggacaggucguacugcuuuug-3'

--Antisense strand--
                                  (SEQ ID NO: 17)
5'-aaagcaguacgaccugucccu-3'
```

Note that, the target sequence set forth in SEQ ID NO: 7 corresponds to the 755th to the 775th in the base sequence set forth in SEQ ID NO: 1.

```
<siTMPO-AS1-5 (siRNA)>
-Target sequence-
                                  (SEQ ID NO: 8)
5'-gaatcctaaacctaacgtttg-3'

-Sequence of siRNA-
--Sense strand--
                                  (SEQ ID NO: 18)
5'-gaauccuaaaccuaacguuug-3'

--Antisense strand--
                                  (SEQ ID NO: 19)
5'-aacguuagguuuaggauucuu-3'
```

Note that, the target sequence set forth in SEQ ID NO: 8 corresponds to the 1,281st to the 1,301st in the base sequence set forth in SEQ ID NO: 1.

```
<siTMPO-AS1-7 (siRNA)>
-Target sequence-
                                  (SEQ ID NO: 9)
5'-cctaacgtttgataacaaaac-3'

-Sequence of siRNA-
--Sense strand--
                                  (SEQ ID NO: 20)
5'-ccuaacguuugauaacaaaac-3'

--Antisense strand--
                                  (SEQ ID NO: 21)
5'-uuuguuaucaaacguuagguu-3'
```

Note that, the target sequence set forth in SEQ ID NO: 9 corresponds to the 1,291st to the 1,311st in the base sequence set forth in SEQ ID NO: 1.

```
<siTMPO-AS1-8 (siRNA)>
-Target sequence-
                                  (SEQ ID NO: 10)
5'-cccgtattaccgatccaaatt-3'

-Sequence of siRNA-
--Sense strand--
                                  (SEQ ID NO: 22)
5'-cccguauuaccgauccaaauu-3'

--Antisense strand--
                                  (SEQ ID NO: 23)
5'-uuuggaucgguaauacggguu-3'
```

Note that, the target sequence set forth in SEQ ID NO: 10 corresponds to the 1,421st to the 1,441st in the base sequence set forth in SEQ ID NO: 1.

```
<siTMPO-AS1-10 (siRNA)>
-Target sequence-
                                  (SEQ ID NO: 11)
5'-cgcgaacgcttcttttgttcc-3'

-Sequence of siRNA-
--Sense strand--
                                  (SEQ ID NO: 24)
5'-cgcgaacgcuucuuuuguucc-3'

--Antisense strand--
                                  (SEQ ID NO: 25)
5'-aacaaaagaagcguucgcgag-3'
```

Note that, the target sequence set forth in SEQ ID NO: 11 corresponds to the 1,051st to the 1,071st in the base sequence set forth in SEQ ID NO: 1.

```
<siCOL18A1-ASx-1 (chimeric siRNA)>
-Target sequence-
                                  (SEQ ID NO: 26)
5'-gcactgtgaggaaggaaat-3'

-Sequence of chimeric siRNA-
--Sense strand--
                                  (SEQ ID NO: 32)
5'-gcacugugaggaaggaaautt-3'

--Antisense strand--
                                  (SEQ ID NO: 33)
5'-auuuccuuccucacagugctt-3'
```

Note that, the target sequence set forth in SEQ ID NO: 26 corresponds to the 673rd to the 691st in the base sequence set forth in SEQ ID NO: 2, to the 1,048th to the 1,066th in the base sequence set forth in SEQ ID NO: 3, and to the 733rd to the 751st in the base sequence set forth in SEQ ID NO: 4.

```
<siCOL18A1-ASx-2 (siRNA)>
-Target sequence-
                                  (SEQ ID NO: 27)
5'-gcttgacggctttctctgaaa-3'

-Sequence of siRNA-
--Sense strand--
                                  (SEQ ID NO: 34)
5'-gcuugacggcuuucucugaaa-3'

--Antisense strand--
                                  (SEQ ID NO: 35)
5'-ucagagaaagccgucaagcca-3'
```

Note that, the target sequence set forth in SEQ ID NO: 27 corresponds to the 216th to the 236th in the base sequence set forth in SEQ ID NO: 2, to the 591st to the 611th in the base sequence set forth in SEQ ID NO: 3, and to the 276th to the 296th in the base sequence set forth in SEQ ID NO: 4.

```
<siCOL18A1-ASx-5 (siRNA)>
-Target sequence-
                                 (SEQ ID NO: 28)
5'-ggaccaaacagcgtagtctcc-3'

-Sequence of siRNA-
--Sense strand--
                                 (SEQ ID NO: 36)
5'-ggaccaaacagcguagucucc-3'

--Antisense strand--
                                 (SEQ ID NO: 37)
5'-agacuacgcuguuugguccag-3'
```

Note that, the target sequence set forth in SEQ ID NO: 28 corresponds to the 301st to the 321st in the base sequence set forth in SEQ ID NO: 2, to the 676th to the 696th in the base sequence set forth in SEQ ID NO: 3, and to the 361st to the 381st in the base sequence set forth in SEQ ID NO: 4.

```
<siCOL18A1-ASx-6 (siRNA)>
-Target sequence-
                                 (SEQ ID NO: 29)
5'-cttcaaacctggagtccttcc-3'

-Sequence of siRNA-
--Sense strand--
                                 (SEQ ID NO: 38)
5'-cuucaaaccuggaguccuucc-3'

--Antisense strand--
                                 (SEQ ID NO: 39)
5'-aaggacuccagguuugaaggc-3'
```

Note that, the target sequence set forth in SEQ ID NO: 29 corresponds to the 637th to the 657th in the base sequence set forth in SEQ ID NO: 2, to the 1,012th to the 1,032nd in the base sequence set forth in SEQ ID NO: 3, and to the 697th to the 717th in the base sequence set forth in SEQ ID NO: 4.

```
<siCOL18A1-ASx-7 (siRNA)>
-Target sequence-
                                 (SEQ ID NO: 30)
5'-gcctgcttgggattctcctct-3'

-Sequence of siRNA-
--Sense strand--
                                 (SEQ ID NO: 40)
5'-gccugcuugggauucuccucu-3'

--Antisense strand--
                                 (SEQ ID NO: 41)
5'-aggagaaucccaagcaggccc-3'
```

Note that, the target sequence set forth in SEQ ID NO: 30 corresponds to the 515th to the 535th in the base sequence set forth in SEQ ID NO: 2, to the 890th to the 910th in the base sequence set forth in SEQ ID NO: 3, and to the 575th to the 595th in the base sequence set forth in SEQ ID NO: 4.

```
<siCOL18A1-ASx-9 (siRNA)>
-Target sequence-
                                 (SEQ ID NO: 31)
5'-gccagggctcatctcctatgc-3'

-Sequence of siRNA-
--Sense strand--
                                 (SEQ ID NO: 42)
5'-gccagggcucaucuccuaugc-3'

--Antisense strand--
                                 (SEQ ID NO: 43)
5'-auaggagaugagcccuggccg-3'
```

Note that, the target sequence set forth in SEQ ID NO: 31 corresponds to the 278th to the 298th in the base sequence set forth in SEQ ID NO: 2, to the 653th to the 673rd in the base sequence set forth in SEQ ID NO: 3, and to the 338th to the 358th in the base sequence set forth in SEQ ID NO: 4.

The sequence of siControl used as a negative control is presented below.

```
<siControl>
-Sense strand-
                                 (SEQ ID NO: 44)
5'-guaccgcacgucauucguauc-3'

-Antisense strand-
                                 (SEQ ID NO: 45)
5'-uacgaaugacgugcgguacgu-3'
```

Test Example 3-1: Study for Suppressive Effects of Double-Stranded Nucleic Acid Molecules on the Expression of Target Non-Coding RNA Breast cancer cells were transfected with siTMPO-AS1-1, 2, 3, 5, 7, 8, or 10 obtained in Production Example 1, followed by culture for 48 hours. Then, total RNA was recovered and subjected to quantitative real-time PCR, to thereby study suppressive effects (knockdown effects) of each double-stranded nucleic acid molecule on the expression of TMPO-AS1 (SEQ ID NO: 1) in the breast cancer cells.

Note that, as a control, siControl was used.

Details of an experiment method are described below.

[Cells]

As the above breast cancer, MCF-7 cells, which are human breast cancer cell line, were used.

[Cell Culture]

MCF-7 cells were cultured at 37° C. in an incubator containing 5% carbon dioxide gas in air using, as a cell culture medium, DMEM (product of NACALAI TESQUE CO., LTD.) containing 10% fetal bovine serum (FBS, product of Sigma Co.), 100 µg/mL streptomycin, and 100 U/mL penicillin (product of Invitrogen Co.).

[Transfection]

MCF-7 cells were seeded in a 6-well plate so as to have a concentration of $1 \times 10^5$ cells/well. On the following day, the cells were transfected with the double-stranded nucleic acid molecule using OPTI-MEM (product of Invitrogen Co.) and RNAi MAX (product of Invitrogen Co.) which is a transfection reagent. An amount of the double-stranded nucleic acid molecule introduced was adjusted to 1 nM in the medium.

[Measurement of Non-Coding RNA Expression Level]

After culture for 48 hours from the transfection, ISOGEN (product of NIPPON GENE CO., LTD.) was used to recover total RNA from the cells. Using 1 µg of the total RNA, cDNA was synthesized by SuperScript (registered trademark) III Reverse Transcriptase (product of Life Technologies Co.).

The cDNA was 10-fold diluted and 2 μL thereof was used to perform quantitative real-time PCR. The quantitative real-time PCR was performed using StepOnePlus (registered trademark) Real-Time PCR Systems (product of Life Technologies) and KAPA SYBR Fast PCR kit (product of NIPPON Genetics Co., Ltd.) to thereby measure the expression levels of TMPO-AS1 (SEQ ID NO: 1) and internal control GAPDH gene.

The expression level of the TMPO-AS1 (SEQ ID NO: 1) was calculated relative to the GAPDH gene using the ΔΔCt method from the Cycle number.

Note that, primers used in the quantitative real-time PCR are as follows.

```
-GAPDH gene-
GAPDH_FW:
                                    (SEQ ID NO: 46)
5'-ggtggtctcctctgacttcaaca-3'

GAPDH_RV:
                                    (SEQ ID NO: 47)
5'-gtggtcgttgagggcaatg-3'

-TMPO-AS1-
TMPO-AS1_FW:
                                    (SEQ ID NO: 50)
5'-tctccaccttcccttagac-3'

TMPO-AS1_RV:
                                    (SEQ ID NO: 51)
5'-aacggcgcacaaaagca-3'
```

Figure 3A:
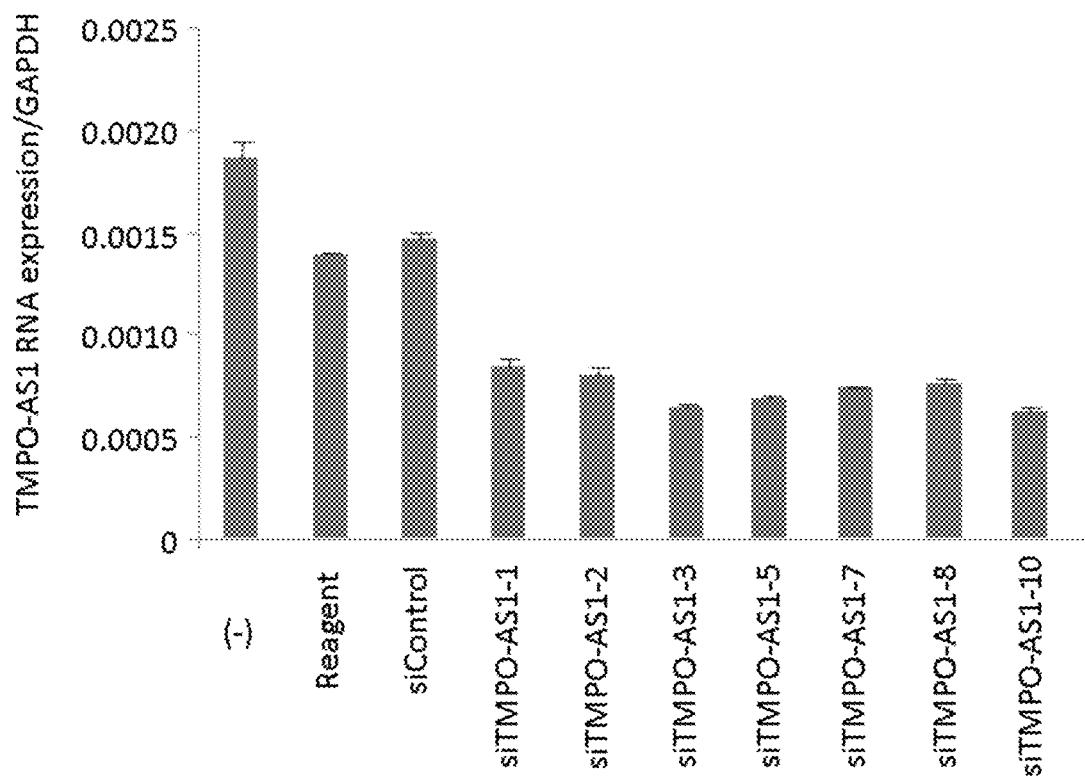
FIG. 3A is a graph indicating results of expression levels of TMPO-AS1 (SEQ ID NO: 1) in Test Example 3-1.

Results are presented in FIG. 3A. In FIG. 3A, "(−)" indicates the result without the treatment, "Reagent" indicates the result when the double-stranded nucleic acid molecule was not transfected (only the reagent), "siControl" indicates the result when "siControl" was transfected, and "siTMPO-AS1-1, 2, 3, 5, 7, 8, 10" indicate the results when "siTMPO-AS1-1, 2, 3, 5, 7, 8, 10" were transfected respectively.

From the results of FIG. 3A, it has become evident that "siTMPO-AS1-1, 2, 3, 5, 7, 8, 10" of the present invention suppress the expression of TMPO-AS1 at the RNA level as compared with siControl.

Test Example 3-2: Study for Suppressive Effects of Double-Stranded Nucleic Acid Molecules on Cell Proliferation In Vitro Breast cancer cells were transfected with siTMPO-AS1-1, 2, 3, 5, 7, 8, or 10 obtained in Production Example 1, and subsequent cell proliferation was measured to study suppressive effects (knockdown effects) of each double-stranded nucleic acid molecule on the proliferation of the breast cancer cells.

Note that, as a control, siControl was used.

Details of an experiment method are described below.

[Cells]

As the above breast cancer, MCF-7 cells, which are human breast cancer cell line, were used.

[Cell Culture]

MCF-7 cells were cultured at 37° C. in an incubator containing 5% carbon dioxide gas in air using, as a cell culture medium, DMEM (product of NACALAI TESQUE CO., LTD.) containing 10% fetal bovine serum (FBS, product of Sigma Co.), 100 μg/mL streptomycin, and 100 U/mL penicillin (product of Invitrogen Co.).

[Transfection]

MCF-7 cells were seeded in a 96-well plate so as to have a concentration of $3 \times 10^3$ cells/well. On the following day, the cells were transfected with the double-stranded nucleic acid molecule using OPTI-MEM (product of Invitrogen Co.) and RNAi MAX (product of Invitrogen Co.) which is a transfection reagent. An amount of the double-stranded nucleic acid molecule introduced was adjusted to 1 nM in the medium.

[Cell Proliferation Test]

The cell proliferation test was performed in the following manner. Specifically, on Day 1 and Day 5 from the transfection, Cell Count Reagent SF (product of NACALAI TESQUE CO., LTD.) was used for reaction for 2 hours, and cell proliferation capability was measured by a microplate reader at an absorbance of 450 nm. The above test is counting the number of living cells by calorimetry of enzymatic activity when tetrazolium salt WST-8 [2-(2-methoxy-4-nitrophenyl)-3-(4-nitrophenyl)-5-(2,4-disulfophenyl)-2H-tetrazolium] is reduced to a highly water-soluble formazan dye.

Figure 3B:
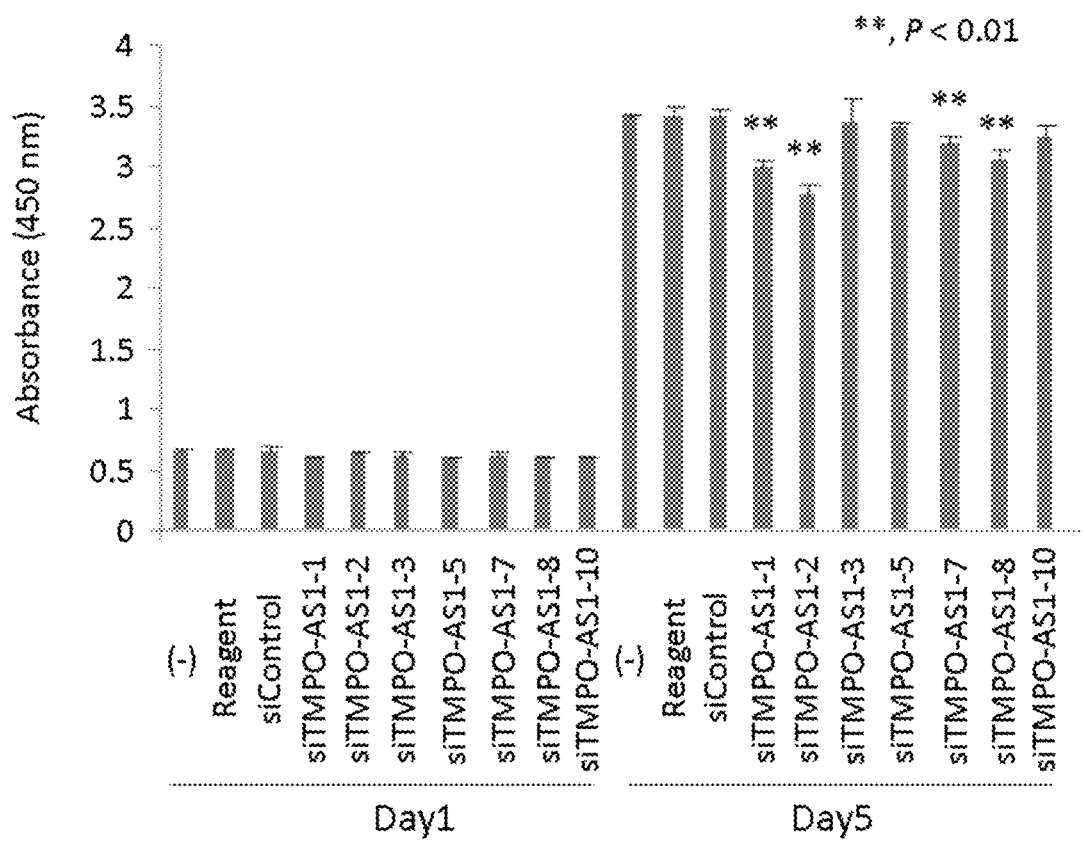
FIG. 3B is a graph indicating results of a cell proliferation test in Test Example 3-2.

Results are presented in FIG. 3B. In FIG. 3B, "(−)" indicates the result without the treatment, "Reagent" indicates the result when the double-stranded nucleic acid molecule was not transfected (only the reagent), "siControl" indicates the result when "siControl" was transfected, and "siTMPO-AS1-1, 2, 3, 5, 7, 8, 10" indicate the results when "siTMPO-AS1-1, 2, 3, 5, 7, 8, 10" were transfected respectively. Also, "Day 1" and "Day 5" indicate the results on Day 1 and Day 5 from the transfection. "**" means "P<0.01".

From the results of FIG. 3B, it has become evident that siTMPO-AS1-2 has the highest cell proliferation suppressive activity and next, in the order of siTMPO-AS1-1, 8, 7, the cell proliferation was suppressed significantly (P<0.01).

Test Example 3-3: Study for Suppressive Effects of Double-Stranded Nucleic Acid Molecules on the Expression of Target Non-Coding RNA In the same manner as in Test Example 3-1 except that siTMPO-AS1-1, 2, 3, 5, 7, 8, or 10 was changed to siTMPO-AS1-1 or 2 and that MCF-7 cells used as the breast cancer cells were changed to the following OHTR cells, suppressive effects (knockdown effects) of each double-stranded nucleic acid molecule on the expression of TMPO-AS1 (SEQ ID NO: 1) in the OHTR cells were studied.

[Cells]

The OHTR cells are tamoxifen-resistant cells, which are a breast cancer therapy-resistant model created from the MCF-7 cells in the following manner.

<Creation of OHTR Cells>

The MCF-7 cells were cultured for 3 months or longer in a DMEM medium containing 4-hydroxytamoxifen (1 μM) which is antiestrogen, to thereby create cells (OHTR cells) acquiring resistance to 4-hydroxytamoxifen.

[Cell Culture]

OHTR cells were cultured at 37° C. in an incubator containing 5% carbon dioxide gas in air using, as a cell culture medium, DMEM (product of NACALAI TESQUE CO., LTD.) containing 10% fetal bovine serum (FBS, product of Sigma Co.), 100 μg/mL streptomycin, and 100 U/mL penicillin (product of Invitrogen Co.).

Figure 3C:
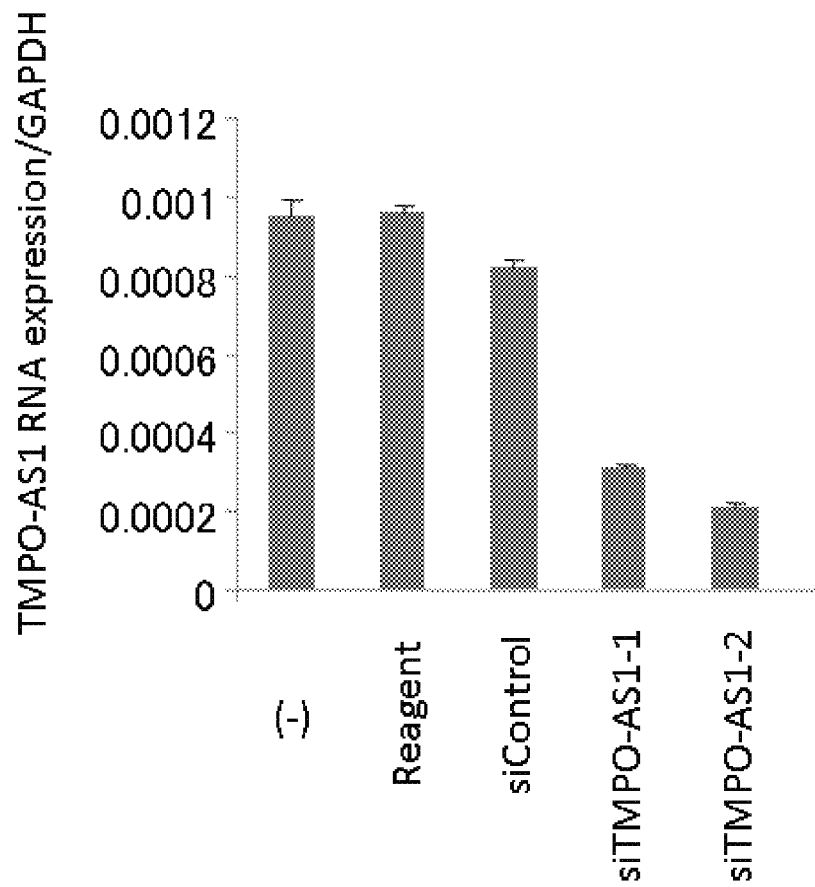
FIG. 3C is a graph indicating results of expression levels of TMPO-AS1 (SEQ ID NO: 1) in Test Example 3-3.

Results of measured non-coding RNA expression levels are presented in FIG. 3C. In FIG. 3C, "(−)" indicates the result without the treatment, "Reagent" indicates the result when the double-stranded nucleic acid molecule was not transfected (only the reagent), "siControl" indicates the result when "siControl" was transfected, and "siTMPO- AS1-1, 2" indicate the results when "siTMPO-AS1-1, 2" were transfected respectively.

From the results of FIG. 3C, it is indicated that "siTMPO-AS1-1, 2" of the present invention suppress the expression of TMPO-AS1 in the OHTR cells.

Test Example 3-4: Study for Suppressive Effects of Double-Stranded Nucleic Acid Molecules on Cell Proliferation In Vitro In the same manner as in Test Example 3-2 except that siTMPO-AS1-1, 2, 3, 5, 7, 8, or 10 was changed to siTMPO-AS1-1 or 2 and that MCF-7 cells used as the breast cancer cells were changed to the OHTR cells prepared in the same manner as in Test Example 3-2, suppressive effects (knockdown effects) of each double-stranded nucleic acid molecule on the proliferation of the OHTR cells were studied.

Figure 3D:
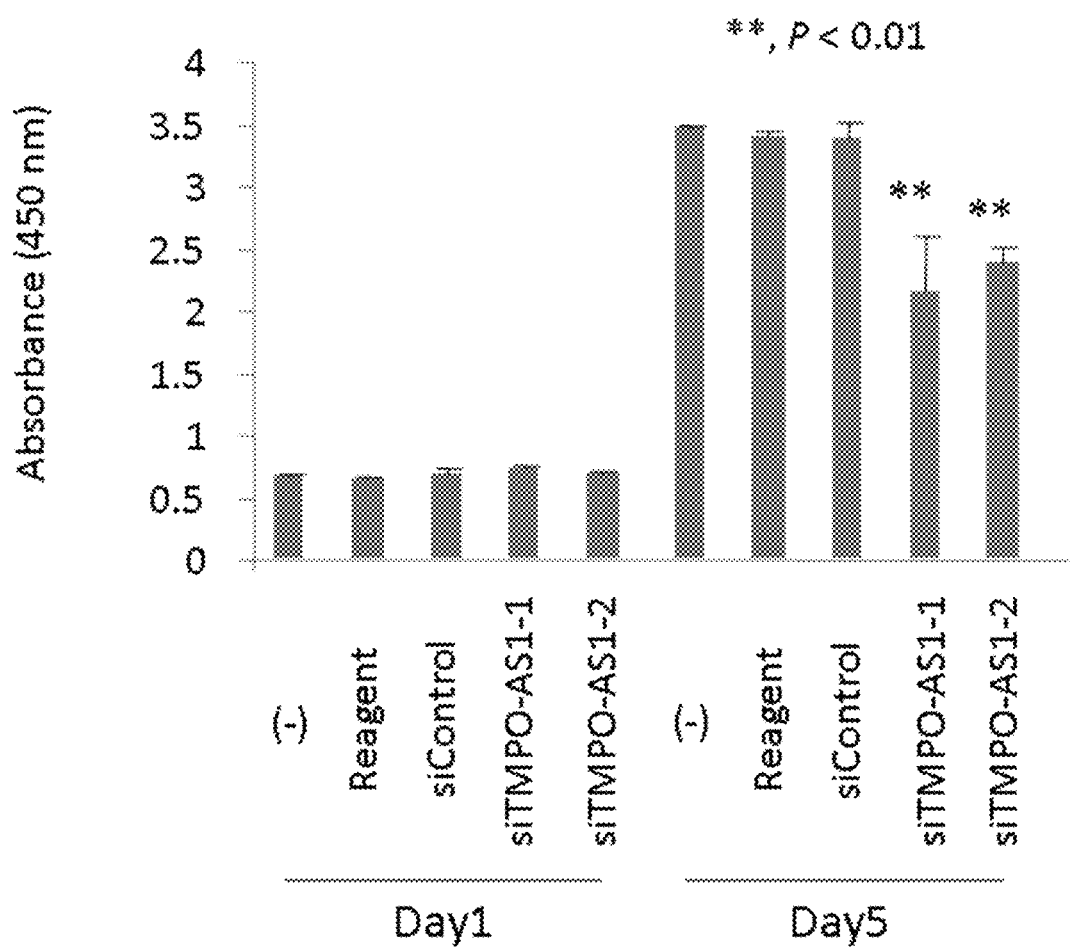
FIG. 3D is a graph indicating results of a cell proliferation test in Test Example 3-4.

Results of the cell proliferation test are presented in FIG. 3D. In FIG. 3D, "(−)" indicates the result without the treatment, "Reagent" indicates the result when the double-stranded nucleic acid molecule was not transfected (only the reagent), "siControl" indicates the result when "siControl" was transfected, and "siTMPO-AS1-1, 2" indicate the results when "siTMPO-AS1-1, 2" were transfected respectively. Also, "Day 1" and "Day 5" indicate the results on Day 1 and Day 5 from the transfection. "**" means "P<0.01".

From the results of FIG. 3D, it has become evident that siTMPO-AS1-1 and siTMPO-AS1-2 suppress the cell proliferation significantly (P<0.01) as compared with siControl.

Test Example 3-5: Study for Suppressive Effects of Double-Stranded Nucleic Acid Molecules on the Expression of Target Non-Coding RNA In the same manner as in Test Example 3-3 except that the MCF-7 cells used as the breast cancer cells were changed to Ishikawa cells which are endometrial cancer cells, suppressive effects (knockdown effects) of each double-stranded nucleic acid molecule on the expression of TMPO-AS1 (SEQ ID NO: 1) in the Ishikawa cells were studied.

[Cell Culture]

Ishikawa cells were cultured at 37° C. in an incubator containing 5% carbon dioxide gas in air using, as a cell culture medium, DMEM (product of NACALAI TESQUE CO., LTD.) containing 10% fetal bovine serum (FBS, product of Sigma Co.), 100 µg/mL streptomycin, and 100 U/mL penicillin (product of Invitrogen Co.).

Figure 3E:
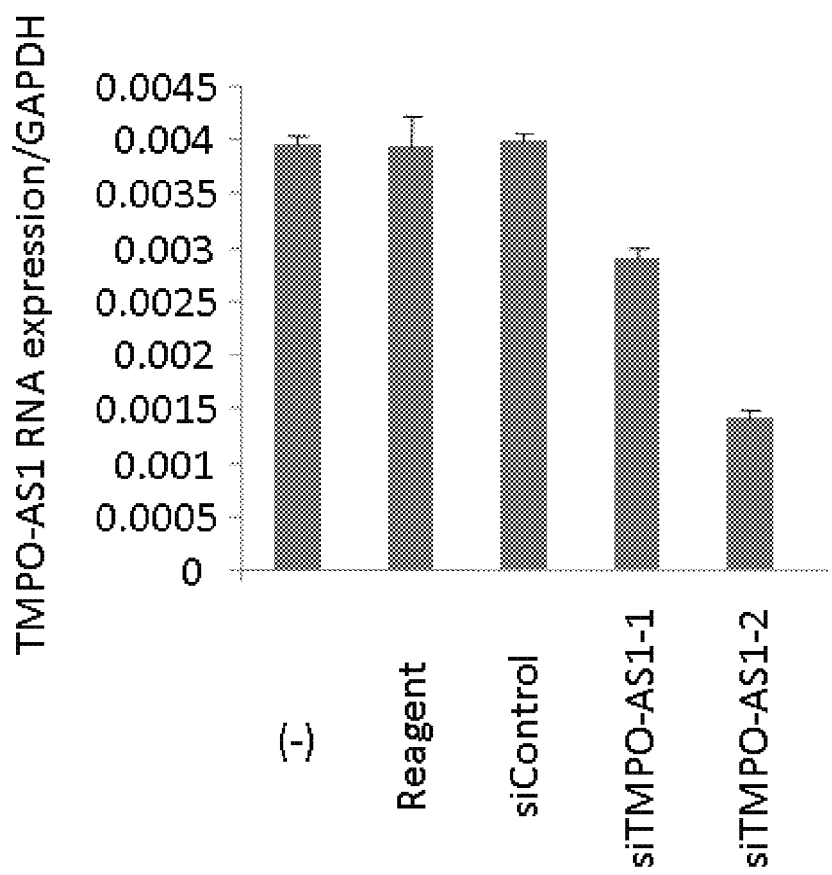
FIG. 3E is a graph indicating results of expression levels of TMPO-AS1 (SEQ ID NO: 1) in Test Example 3-5.

Results of measured non-coding RNA expression levels are presented in FIG. 3E. In FIG. 3E, "(−)" indicates the result without the treatment, "Reagent" indicates the result when the double-stranded nucleic acid molecule was not transfected (only the reagent), "siControl" indicates the result when "siControl" was transfected, and "siTMPO-AS1-1, 2" indicate the results when "siTMPO-AS1-1, 2" were transfected respectively.

From the results of FIG. 3E, it is indicated that "siTMPO-AS1-1, 2" of the present invention suppress the expression of TMPO-AS1 in the Ishikawa cells, and the effect is particularly high in siTMPO-AS1-2.

Test Example 3-6: Study for Suppressive Effects of Double-Stranded Nucleic Acid Molecules on Cell Proliferation In Vitro In the same manner as in Test Example 3-4 except that the MCF-7 cells used as the breast cancer cells were changed to Ishikawa cells which are endometrial cancer cells, suppressive effects (knockdown effects) of each double-stranded nucleic acid molecule on the proliferation of the Ishikawa cells were studied.

Note that, the Ishikawa cells were cultured in the same manner as in Test Example 3-5.

Figure 3F:
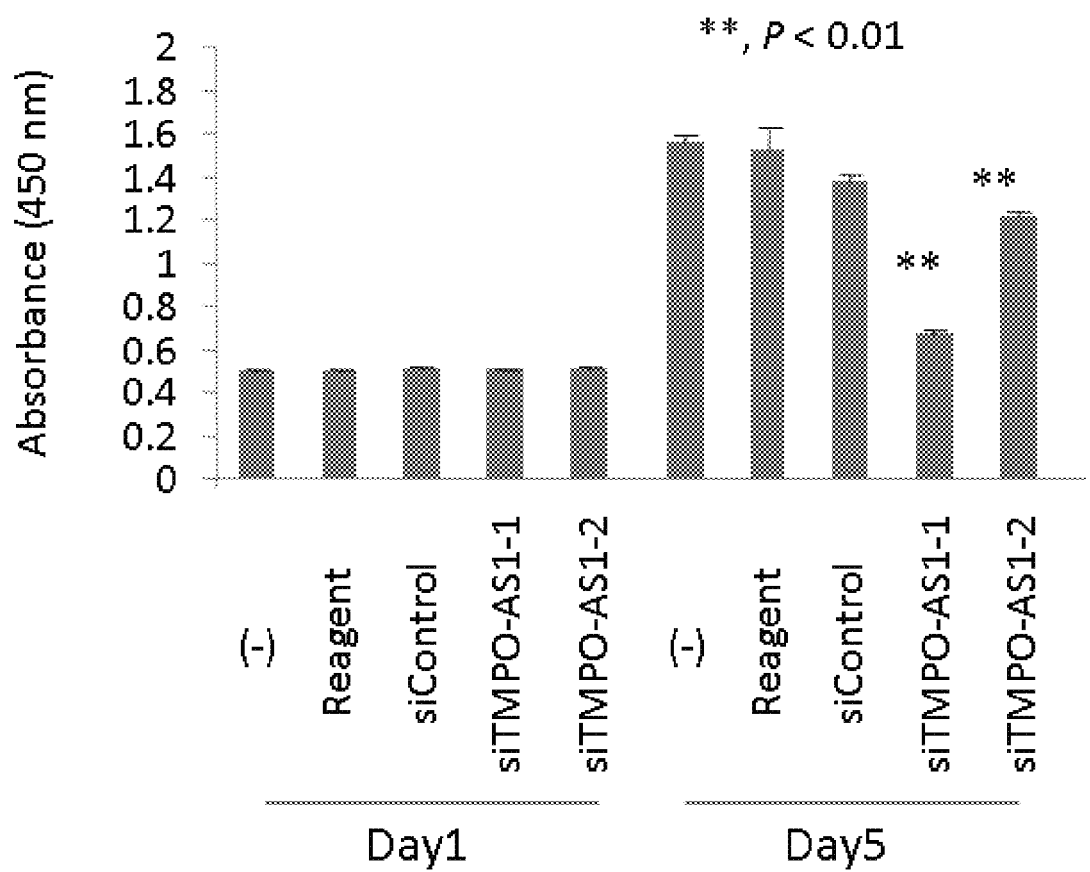
FIG. 3F is a graph indicating results of a cell proliferation test in Test Example 3-6.

Results of the cell proliferation test are presented in FIG. 3F. In FIG. 3F, "(−)" indicates the result without the treatment, "Reagent" indicates the result when the double-stranded nucleic acid molecule was not transfected (only the reagent), "siControl" indicates the result when "siControl" was transfected, and "siTMPO-AS1-1, 2" indicate the results when "siTMPO-AS1-1, 2" were transfected respectively. Also, "Day 1" and "Day 5" indicate the results on Day 1 and Day 5 from the transfection. "**" means "P<0.01".

From the results of FIG. 3F, it has become evident that siTMPO-AS1-1 and siTMPO-AS1-2 suppress the cell proliferation significantly (P<0.01) as compared with siControl.

Test Example 4-1: Study for Suppressive Effects of Double-Stranded Nucleic Acid Molecules on the Expression of Target Non-Coding RNA In the same manner as in Test Example 3-1 except that TMPO-AS1 (SEQ ID NO: 1) used as the target non-coding RNA was changed to COL18A1-ASx (SEQ ID NOs: 2 to 4), that siTMPO-AS1-1, 2, 3, 5, 7, 8, or 10 was changed to siCOL18A1-ASx-1, 2, 5, 6, 7, or 9, and that the expression level of COL18A1-ASx (SEQ ID NOs: 2 to 4) was measured in quantitative real-time PCR instead of the expression level of TMPO-AS1 (SEQ ID NO: 1), suppressive effects (knockdown effects) of each double-stranded nucleic acid molecule on the expression of COL18A1-ASx (SEQ ID NOs: 2 to 4) in the MCF-7 cells were studied.

Note that, primers of COL18A1-ASx (SEQ ID NOs: 2 to 4) used in the quantitative real-time PCR are as follows.

```
-COL18A1-ASx (SEQ ID NOs: 2 to 4)-
COL18A1-ASx_FW:
                                (SEQ ID NO: 48)
5'-gccagggctcatctcctatg-3'

COL18A1-ASx_RV:
                                (SEQ ID NO: 49)
5'-ggagatcagggagactggagact-3'
```

Figure 4A:
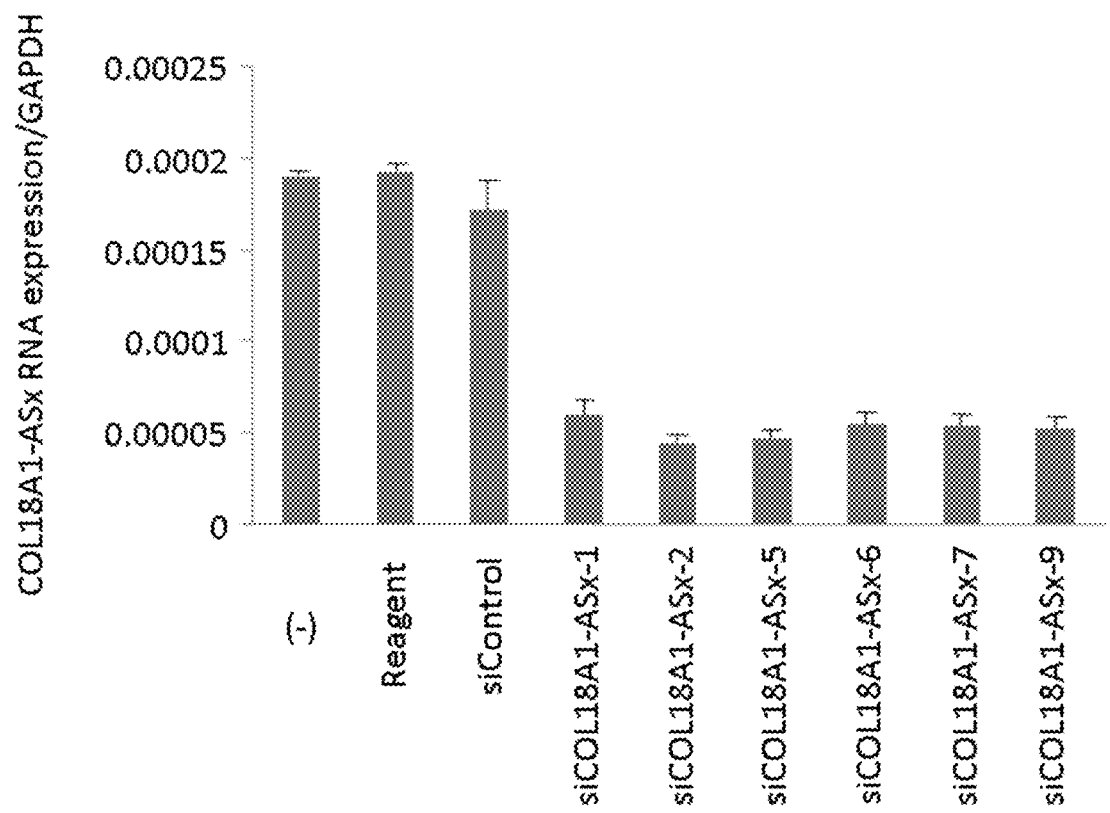
FIG. 4A is a graph indicating results of expression levels of COL18A1-ASx (SEQ ID NOs: 2 to 4) in Test Example 4-1.

Results are presented in FIG. 4A. In FIG. 4A, "(−)" indicates the result without the treatment, "Reagent" indicates the result when the double-stranded nucleic acid molecule was not transfected (only the reagent), "siControl" indicates the result when "siControl" was transfected, and "siCOL18A1-ASx-1, 2, 5, 6, 7, 9" indicate the results when "siCOL18A1-ASx-1, 2, 5, 6, 7, 9" were transfected respectively.

From the results of FIG. 4A, it has become evident that "siCOL18A1-ASx-1, 2, 5, 6, 7, 9" of the present invention suppress the expression of COL18A1-ASx (SEQ ID NOs: 2 to 4) at the RNA level as compared with siControl.

Test Example 4-2: Study for Suppressive Effects of Double-Stranded Nucleic Acid Molecules on Cell Proliferation In Vitro In the same manner as in Test Example 3-2 except that siTMPO-AS1-1, 2, 3, 5, 7, 8, or 10 was changed to siCOL18A1-ASx-1, 2, 5, 6, 7, or 9, suppressive effects (knockdown effects) of each double-stranded nucleic acid molecule on the proliferation of the MCF-7 cells were studied.

Figure 4B:
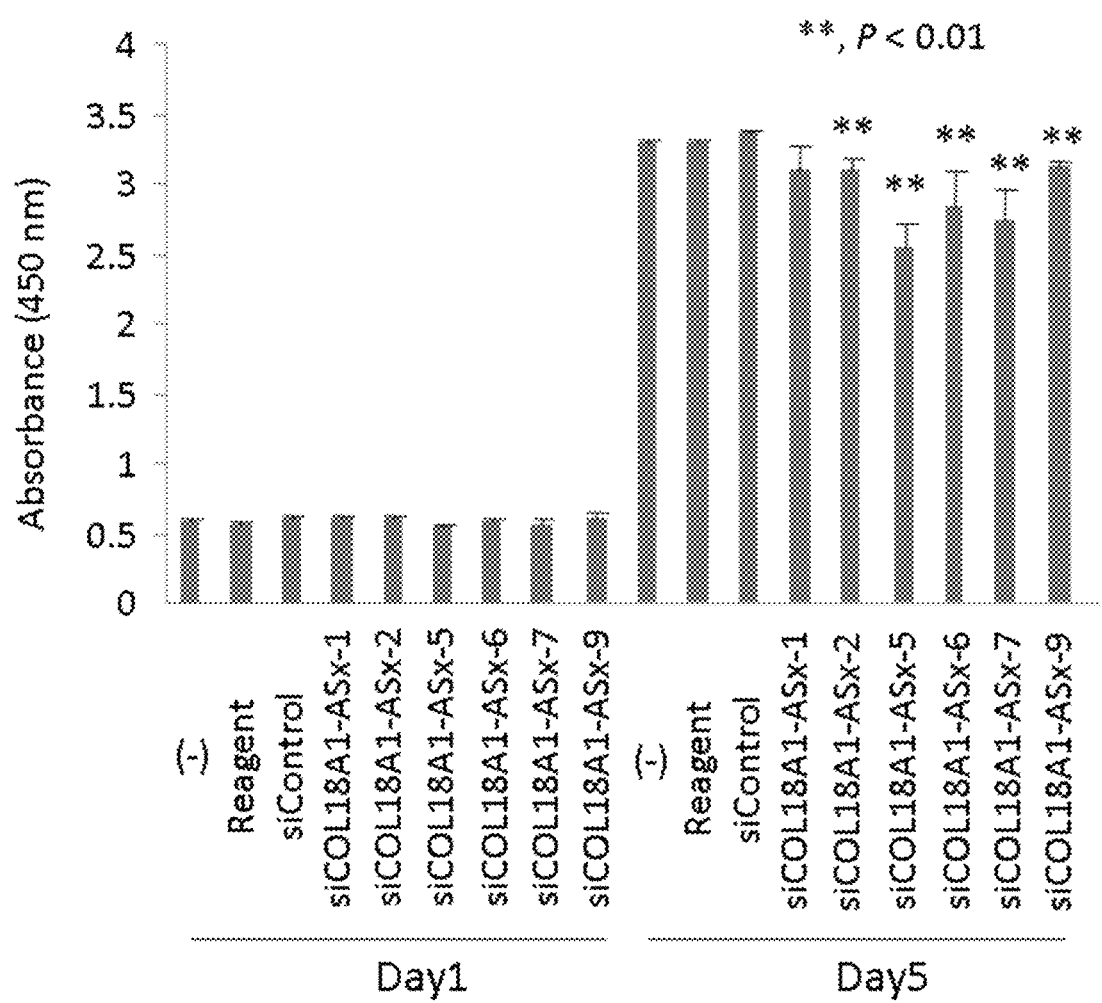
FIG. 4B is a graph indicating results of a cell proliferation test in Test Example 4-2.

Results are presented in FIG. 4B. In FIG. 4B, "(−)" indicates the result without the treatment, "Reagent" indicates the result when the double-stranded nucleic acid molecule was not transfected (only the reagent), "siControl" indicates the result when "siControl" was transfected, and "siCOL18A1-ASx-1, 2, 5, 6, 7, 9" indicate the results when "siCOL18A1-ASx-1, 2, 5, 6, 7, 9" were transfected respectively. Also, "Day 1" and "Day 5" indicate the results on Day 1 and Day 5 from the transfection. "**" means "P<0.01".

From the results of FIG. 4B, siCOL18A1-ASx-2, 5, 6, 7, 9 suppressed the cell proliferation significantly (P<0.01) as compared with siControl. Among them, it has become evident that siCOL18A1-ASx-5 has the highest cell proliferation suppressive activity.

Test Example 4-3: Study for Suppressive Effects of Double-Stranded Nucleic Acid Molecules on the Expression of Target Non-Coding RNA In the same manner as in Test Example 4-1 except that the MCF-7 cells used as the breast cancer cells were changed to OHTR cells prepared in the same manner as in Test Example 3-2, suppressive effects (knockdown effects) of each double-stranded nucleic acid molecule on the expression of COL18A1-ASx (SEQ ID NOs: 2 to 4) in the OHTR cells were studied.

Figure 4C:
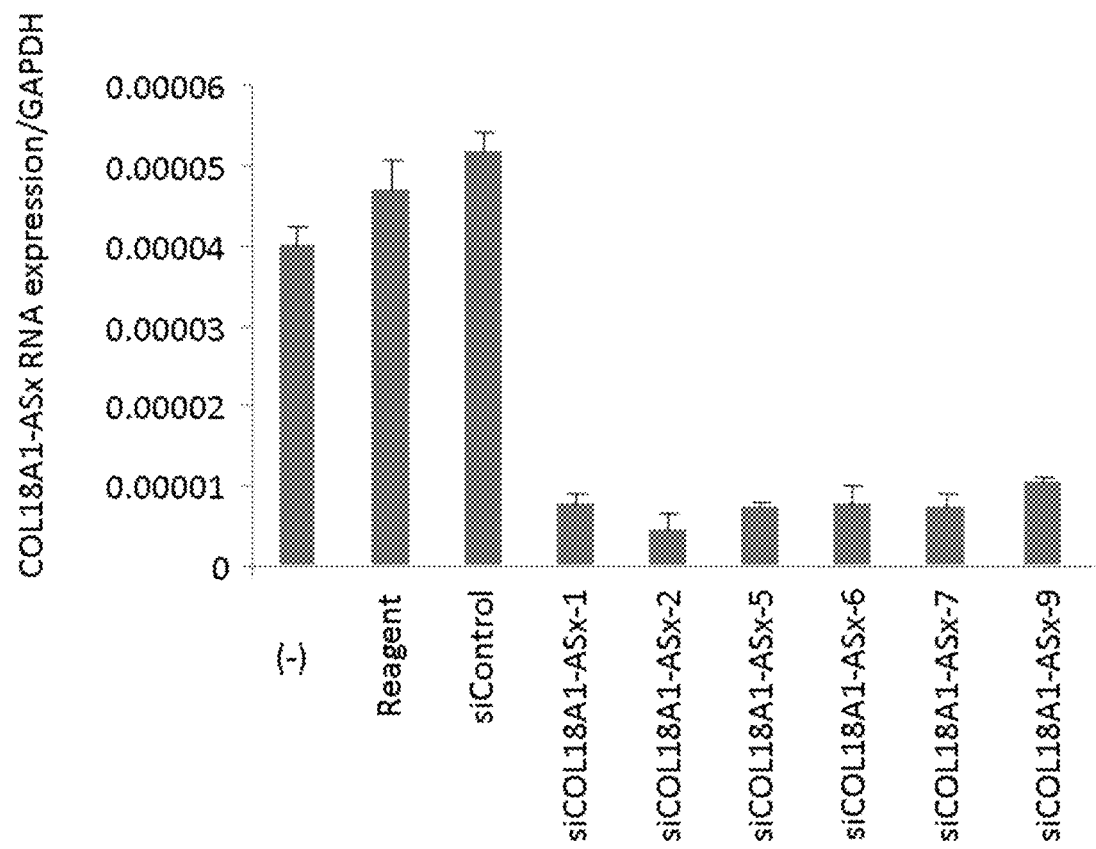
FIG. 4C is a graph indicating results of expression levels of COL18A1-ASx (SEQ ID NOs: 2 to 4) in Test Example 4-3.

Results of measured non-coding RNA expression levels are presented in FIG. 4C. In FIG. 4C, "(−)" indicates the result without the treatment, "Reagent" indicates the result when the double-stranded nucleic acid molecule was not transfected (only the reagent), "siControl" indicates the result when "siControl" was transfected, and "siCOL18A1-ASx-1, 2, 5, 6, 7, 9" indicate the results when "siCOL18A1-ASx-1, 2, 5, 6, 7, 9" were transfected respectively.

From the results of FIG. 4C, it is indicated that "siCOL18A1-ASx-1, 2, 5, 6, 7, 9" of the present invention suppressed the expression of COL18A1-ASx (SEQ ID NOs: 2 to 4) in the OHTR cells.

Test Example 4-4: Study for Suppressive Effects of Double-Stranded Nucleic Acid Molecules on Cell Proliferation In Vitro In the same manner as in Test Example 4-2 except that the MCF-7 cells used as the breast cancer cells were changed to OHTR cells prepared in the same manner as in Test Example 3-2, suppressive effects (knockdown effects) of each double-stranded nucleic acid molecule on the proliferation of the OHTR cells were studied.

Figure 4D:
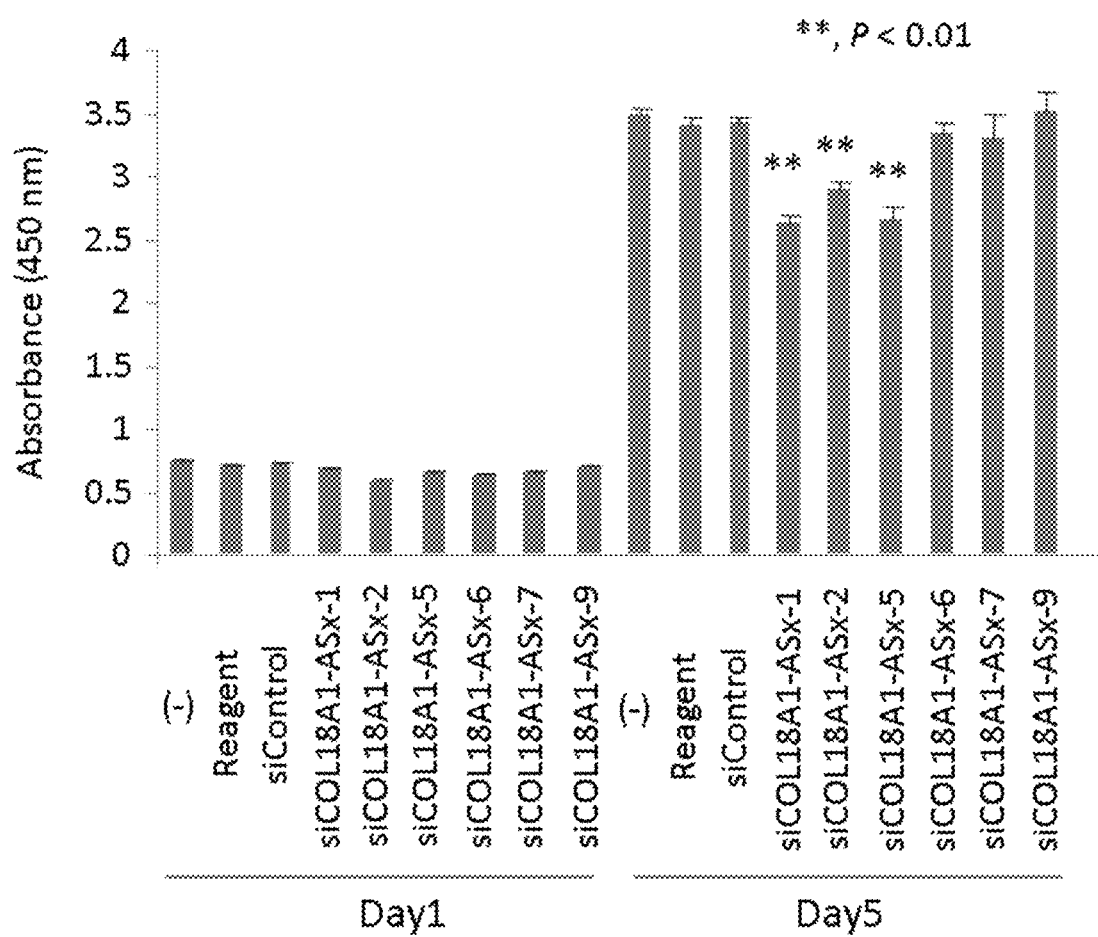
FIG. 4D is a graph indicating results of a cell proliferation test in Test Example 4-4.

Results of the cell proliferation test are presented in FIG. 4D. In FIG. 4D, "(−)" indicates the result without the treatment, "Reagent" indicates the result when the double-stranded nucleic acid molecule was not transfected (only the reagent), "siControl" indicates the result when "siControl" was transfected, and "siCOL18A1-ASx-1, 2, 5, 6, 7, 9" indicate the results when "siCOL18A1-ASx-1, 2, 5, 6, 7, 9" were transfected respectively. Also, "Day 1" and "Day 5" indicate the results on Day 1 and Day 5 from the transfection. "**" means "P<0.01".

From the results of FIG. 4D, it has become evident that siCOL18A1-ASx-1, 2, 5 suppress the cell proliferation significantly (P<0.01) as compared with siControl.

Test Example 4-5: Study for Suppressive Effects of Double-Stranded Nucleic Acid Molecules on the Expression of Target Non-Coding RNA In the same manner as in Test Example 4-1 except that MCF-7 cells used as the breast cancer cells were changed to Ishikawa cells which are endometrial cancer cells, suppressive effects (knockdown effects) of each double-stranded nucleic acid molecule on the expression of COL18A1-ASx (SEQ ID NOs: 2 to 4) in the Ishikawa cells were studied.

Note that, the Ishikawa cells were cultured in the same manner as in Test Example 3-5.

Figure 4E:
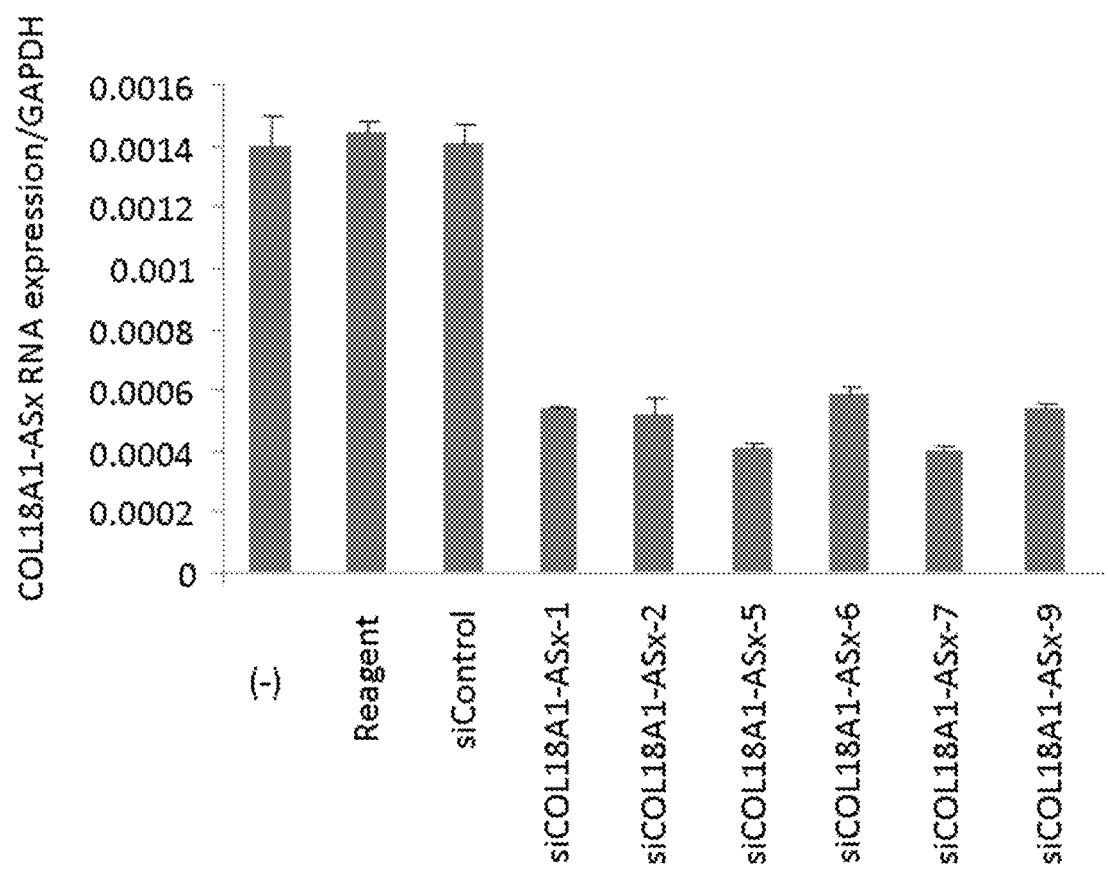
FIG. 4E is a graph indicating results of expression levels of COL18A1-ASx (SEQ ID NOs: 2 to 4) in Test Example 4-5.

Results of measured non-coding RNA expression levels are presented in FIG. 4E. In FIG. 4E, "(−)" indicates the result without the treatment, "Reagent" indicates the result when the double-stranded nucleic acid molecule was not transfected (only the reagent), "siControl" indicates the result when "siControl" was transfected, and "siCOL18A1-ASx-1, 2, 5, 6, 7, 9" indicate the results when "siCOL18A1-ASx-1, 2, 5, 6, 7, 9" were transfected respectively.

From the results of FIG. 4E, it is indicated that "siCOL18A1-ASx-1, 2, 5, 6, 7, 9" of the present invention suppressed the expression of COL18A1-ASx (SEQ ID NOs: 2 to 4) in the Ishikawa cells.

Test Example 4-6: Study for Suppressive Effects of Double-Stranded Nucleic Acid Molecules on Cell Proliferation In Vitro In the same manner as in Test Example 4-2 except that MCF-7 cells used as the breast cancer cells were changed to Ishikawa cells which are endometrial cancer cells, suppressive effects (knockdown effects) of each double-stranded nucleic acid molecule on the proliferation of the Ishikawa cells were studied.

Note that, the Ishikawa cells were cultured in the same manner as in Test Example 3-5.

Figure 4F:
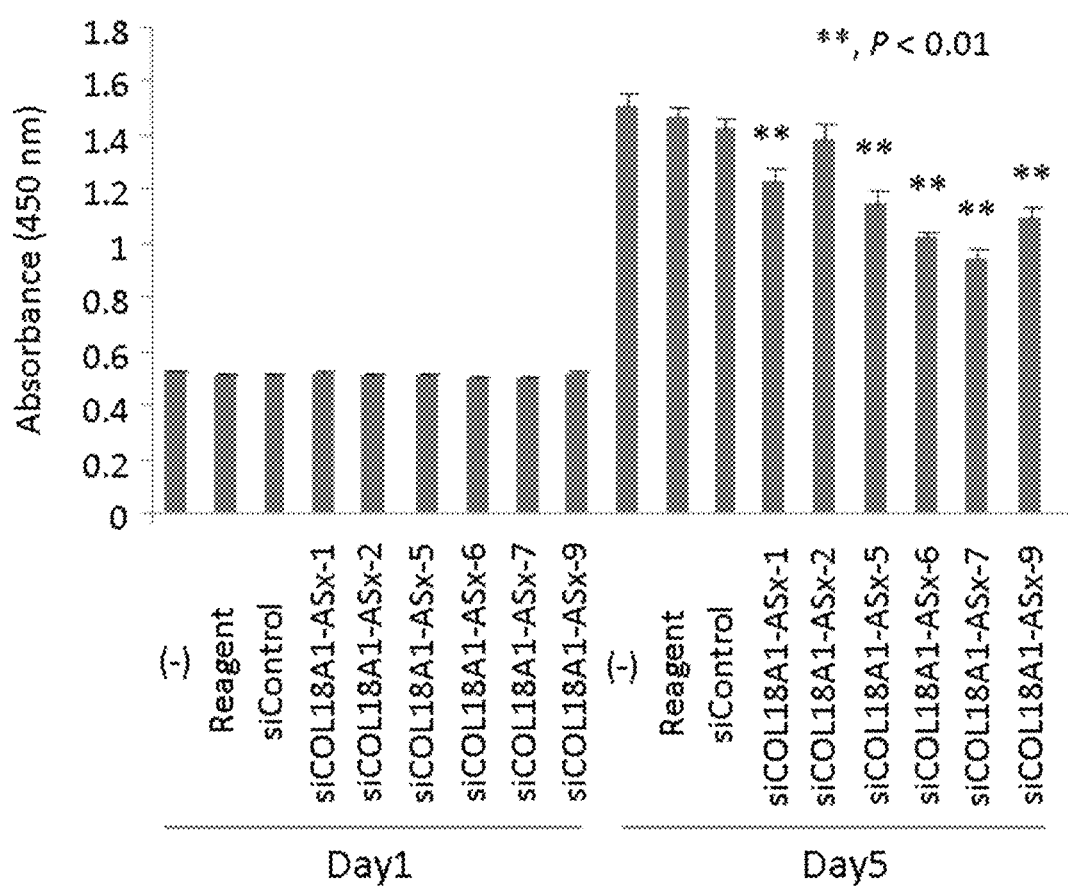
FIG. 4F is a graph indicating results of a cell proliferation test in Test Example 4-6.

Results of the cell proliferation test are presented in FIG. 4F. In FIG. 4F, "(−)" indicates the result without the treatment, "Reagent" indicates the result when the double-stranded nucleic acid molecule was not transfected (only the reagent), "siControl" indicates the result when "siControl" was transfected, and "siCOL18A1-ASx-1, 2, 5, 6, 7, 9" indicate the results when "siCOL18A1-ASx-1, 2, 5, 6, 7, 9" were transfected respectively. Also, "Day 1" and "Day 5" indicate the results on Day 1 and Day 5 from the transfection. "**" means "P<0.01".

From the results of FIG. 4F, it has become evident that siCOL18A1-ASx-1, 5, 6, 7, 9 suppress the cell proliferation significantly (P<0.01) as compared with siControl.

Test Example 5: Study for Suppressive Effects of Double-Stranded Nucleic Acid Molecules on Tumor Growth In Vitro Regarding siTMPO-AS1-2 and siCOL18A1-ASx-5 in the double-stranded nucleic acid molecules prepared in Production Example 1, their suppressive effects on the growth of tumor were studied in mice into which tumor cells had been subcutaneously transplanted.

The siTMPO-AS1-2 and siCOL18A1-ASx-5 are those having both high expression suppressive effects at the RNA level and high cell proliferation suppressive effects in the MCF-7 cells.

Note that, as a control, siControl was used.

Details of an experiment method are described below.
[Cells]
As the above tumor cells, MCF-7 cells, which are human breast cancer cell line, were used.
[Mice]
As the above mice, 8-week-old female nude mice purchased from CLEA Japan, Inc. (BALB/cAJcl-nu/nu) were used.

[Subcutaneous Transplantation of Tumor Cells]

The MCF-7 cells were adjusted in 75 μL of DMEM (Dulbecco's Modified Eagle Medium) so as to be $4\times10^6$ cells per one nude mouse, and further mixed with 75 μL of Matrigel (product of BD bioscience Co.). The resultant mixture was subcutaneously injected into the mouse.

[Administration (Injection) of Double-Stranded Nucleic Acid Molecules)]

From the time when the tumor volume exceeded 100 mm$^3$ after the transplantation of the tumor cells into the mouse, each of the double-stranded nucleic acid molecules was injected twice a week.

The injection of the double-stranded nucleic acid molecule into the tumor was performed using RNAi MAX (product of Invitrogen Co.). Specifically, 5 μg of the double-stranded nucleic acid molecule was suspended in 50 μL of Opti-MEM (product of GIBCO Co.) and 15 μL of RNAi MAX was suspended in 50 μL of Opti-MEM. The resultant suspensions were mixed together and then locally injected into the tumor of the mouse.

[Measurement of Tumor Growth and Evaluation]

The size of the tumor of the mouse was measured twice a week.

The tumor volume was calculated from the formula: [{major radius (r1) (mm)×minor radius (r2) (mm)×minor radius (r3) (mm)}/2] by measuring the tumor for the major radius (r1) and the minor radii (r2, r3) at two places.

Figure 5A:
FIG. 5A illustrates states of representative tumors photographed in Test Example 5.
Figure 5B:
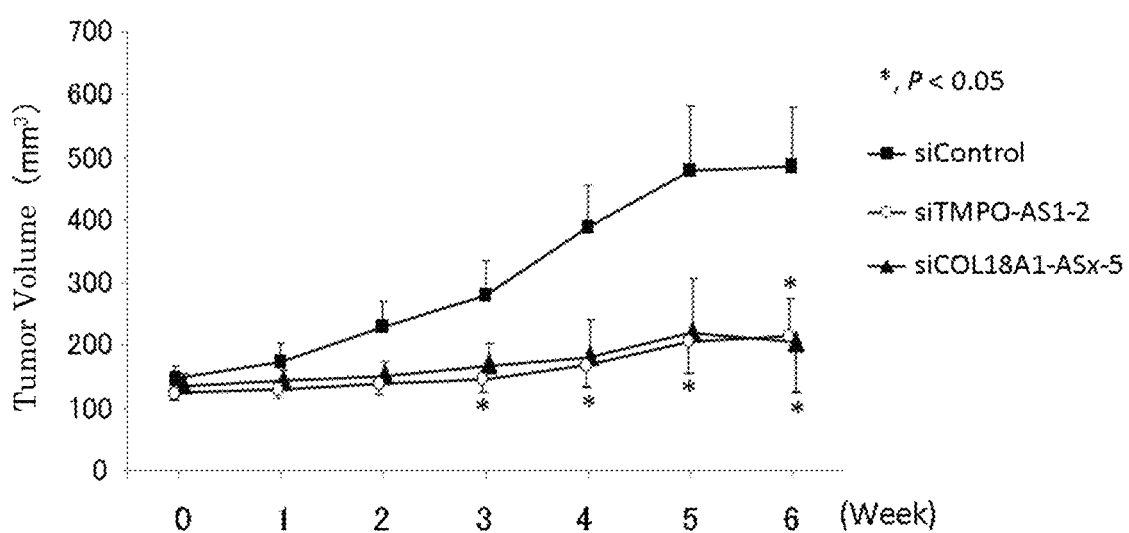
FIG. 5B is a graph indicating changes in tumor volumes in Test Example 5.

Results are presented in FIGS. 5A and 5B.

FIG. 5A illustrates states of representative tumors photographed 6 weeks after the start of the administration of the double-stranded nucleic acid molecule (the top row: siControl was administered, the middle row: siTMPO-AS1-2 was administered, the bottom row: siCOL18A1-ASx-5 was administered).

FIG. 5B is a graph indicating changes in the tumor volumes. In FIG. 5B, "black square" indicates the result of the mice (n=8) to which "siControl" had been administered, "white circle" indicates the results of the mice (n=9) to which "siTMPO-AS1-2" had been administered, and "black triangle" indicates the result of the mice (n=8) to which "siCOL18A1-ASx-5" had been administered. Also, in this figure, "*" means p<0.05.

From the results of FIGS. 5A and 5B, it has become evident that administration of siTMPO-AS1-2 or siCOL18A1-ASx-5 significantly suppresses the growth of the tumor derived from MCF-7 cells in the mice.

Test Example 6-1: Study for Suppressive Effects of Double-Stranded Nucleic Acid Molecules on Cell Movements In Vitro Breast cancer cells were transfected with siTMPO-AS1-1 or 2 obtained in Production Example 1, and then movements of the cells were measured to study suppressive effects of each double-stranded nucleic acid molecule on breast cancer cell movements.

Note that, as a control, siControl was used.

Details of an experiment method are described below.

[Cells]

As the above breast cancer cells, MCF-7 cells, which are human breast cancer cell line, were used.

[Cell Culture]

MCF-7 cells were cultured at 37° C. in an incubator containing 5% carbon dioxide gas in air using, as a cell culture medium, DMEM (product of NACALAI TESQUE CO., LTD.) containing 10% fetal bovine serum (FBS, product of Sigma Co.), 100 μg/mL streptomycin, and 100 U/mL penicillin (product of Invitrogen Co.).

[Transfection]

MCF-7 cells were seeded in a 96-well plate so as to have a concentration of $3\times10^3$ cells/well. On the following day, the cells were transfected with the double-stranded nucleic acid molecule using OPTI-MEM (product of Invitrogen Co.) and RNAi MAX (product of Invitrogen Co.) which is a transfection reagent. An amount of the double-stranded nucleic acid molecule introduced was adjusted to 10 nM in the medium.

[Cell Movement Test]

The cell movement test was performed in the following manner. Specifically, 2 days or 3 days after the transfection, the cells were seeded in a culture chamber (Cell Culture Insert with 8.0-μm pore size PET filter (product of BD bioscience Co.)) at a concentration of 50,000 cells/well, followed by further incubation for 3 days. Thereafter, the culture chamber was subjected to methanol fixation and then stained by Giemsa stain solution. The cells having passed through the filter of the culture chamber were counted under a microscope in at least 5 or more fields of view.

Figure 6A:
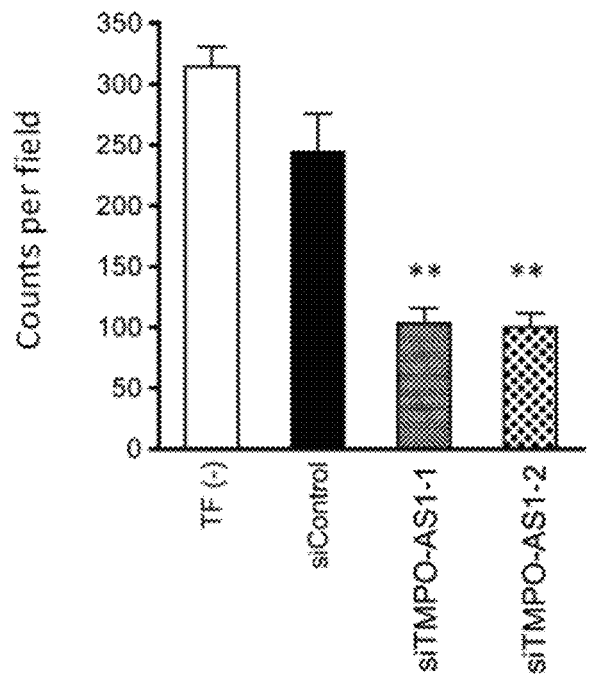
FIG. 6A is a graph indicating results of a cell movement test in Test Example 6-1.

Results are presented in FIG. 6A. In FIG. 6A, "TF(−)" indicates the result without the treatment, "siControl" indicates the result when "siControl" was transfected, and "siTMPO-AS1-1, 2" indicate the results when "siTMPO-AS1-1, 2" were transfected respectively. "**" means "P<0.01".

From the results of FIG. 6A, it has become evident that the MCF-7 cells treated with siTMPO-AS1-1 or 2 were fewer than the MCF-7 cells treated with siControl serving as a control in terms of the number of the moved cells, indicating that the double-stranded nucleic acid molecules of the present invention suppressed the movements of cancer cells.

Test Example 6-2: Study for Suppressive Effects of Double-Stranded Nucleic Acid Molecules on Cell Movements In Vitro In the same manner as in Test Example 6-1 except that siTMPO-AS1-1 or 2 was changed to siCOL18A1-ASx-1 or 5, suppressive effects of each double-stranded nucleic acid molecule on cell movements were studied.

Figure 6B:
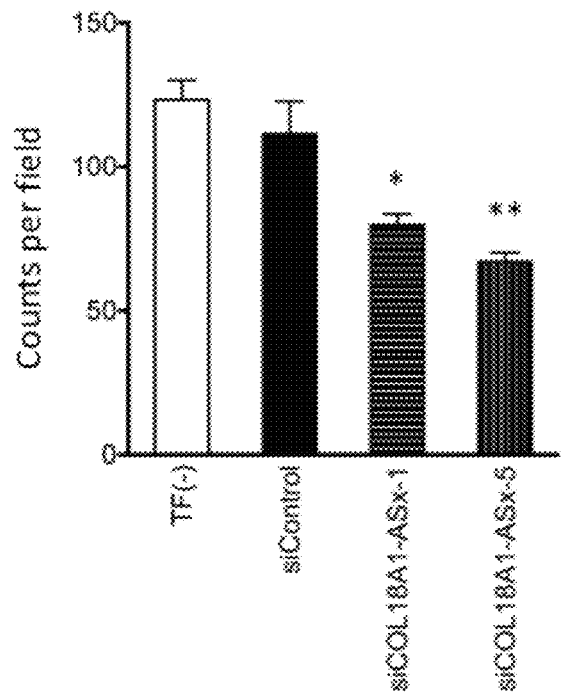
FIG. 6B is a graph indicating results of a cell movement test in Test Example 6-2.

Results are presented in FIG. 6B. In FIG. 6B, "TF(−)" indicates the result without the treatment, "siControl" indicates the result when "siControl" was transfected, and "siCOL18A1-ASx-1, 5" indicate the results when "siCOL18A1-ASx-1, 5" were transfected respectively. "*" means "P<0.05". "**" means "P<0.01".

From the results of FIG. 6B, it has become evident that the MCF-7 cells treated with siCOL18A1-ASx-1 or 5 were fewer than the MCF-7 cells treated with siControl serving as the control in terms of the number of the moved cells, indicating that the double-stranded nucleic acid molecules of the present invention suppress the movements of cancer cells.

Test Example 7: Study for Suppressive Effects of Double-Stranded Nucleic Acid Molecules on Tumor Growth In Vitro Regarding siTMPO-AS1-2, siCOL18A1-ASx-1, and siCOL18A1-ASx-5 in the double-stranded nucleic acid molecules prepared in Production Example 1, their suppressive effects on the growth of tumor were studied in mice into which tumor cells had been subcutaneously transplanted.

Note that, as a control, siControl was used.

Details of an experiment method are described below.

[Cells]

As the above tumor cells, OHTR cells were used which are tamoxifen-resistant cells and a breast cancer therapy-resistant model. Note that, the OHTR cells were created in the same manner as in Test Example 3-3.

[Mice]

As the above mice, 8-week-old female nude mice purchased from CLEA Japan, Inc. (BALB/cAJcl-nu/nu) were used.

[Subcutaneous Transplantation of Tumor Cells]

The OHTR cells were adjusted in 75 µL of DMEM (Dulbecco's Modified Eagle Medium) so as to be 20,000,000 cells per one nude mouse, and further mixed with 75 µL of Matrigel (product of BD bioscience Co.). The resultant mixture was subcutaneously injected into the mouse.

[Administration (Injection) of Double-Stranded Nucleic Acid Molecules)]

From the time when the tumor volume exceeded 300 mm$^3$ after the transplantation of the tumor cells into the mouse, each of the double-stranded nucleic acid molecules was injected twice a week.

The injection of the double-stranded nucleic acid molecule into the tumor was performed using RNAi MAX (product of Invitrogen Co.). Specifically, 5 µg of the double-stranded nucleic acid molecule was suspended in 50 µL of Opti-MEM (product of GIBCO Co.) and 15 µL of RNAi MAX was suspended in 50 µL of Opti-MEM. The resultant suspensions were mixed together and then locally injected into the tumor of the mouse.

[Measurement of Tumor Growth and Evaluation]

The size of the tumor of the mouse was measured twice a week.

The tumor volume was calculated from the formula: [{major radius (r1) (mm)×minor radius (r2) (mm)×minor radius (r3) (mm)}/2] by measuring the tumor for the major radius (r1) and the minor radii (r2, r3) at two places.

Figure 7A:
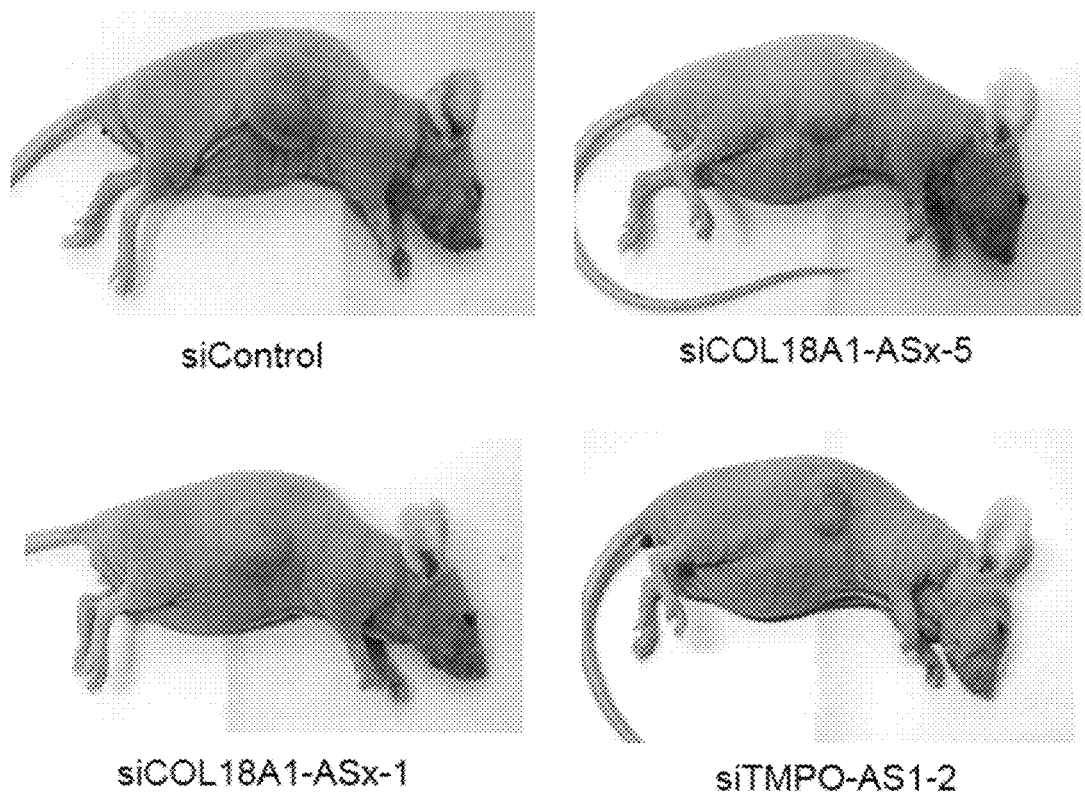
FIG. 7A illustrates states of representative tumors photographed in Test Example 7.
Figure 7B:
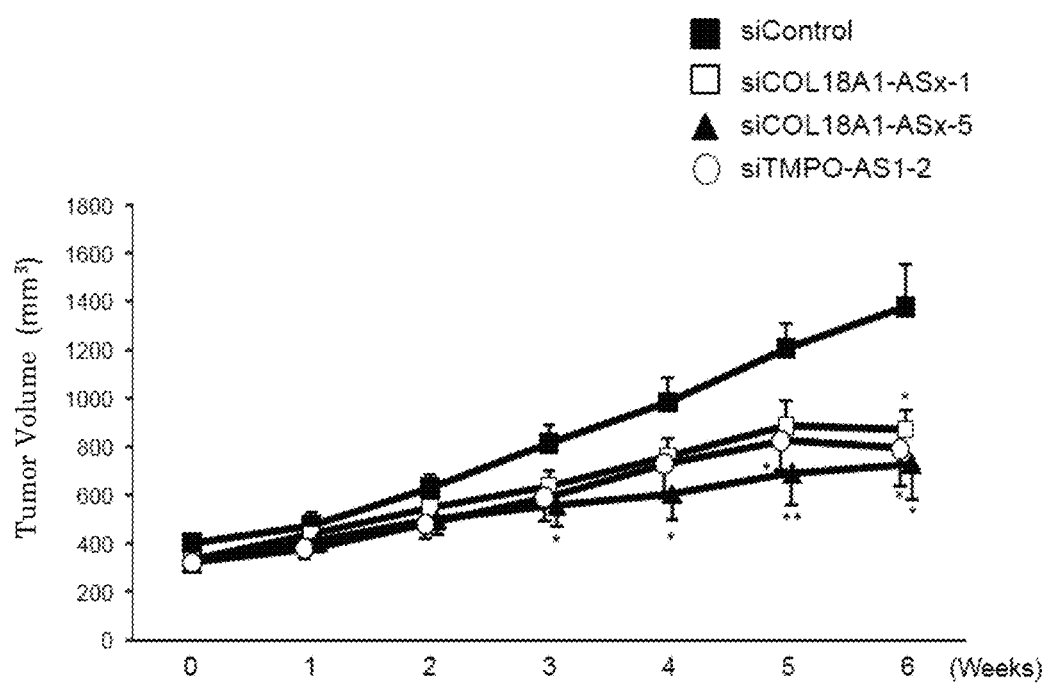
FIG. 7B is a graph indicating changes in tumor volumes in Test Example 7.

Results are presented in FIGS. 7A and 7B.

FIG. 7A illustrates states of representative tumors photographed 6 weeks after the start of the administration of the double-stranded nucleic acid molecule (the left-upper: siControl was administered, the left-lower: siCOL18A1-ASx-1 was administered, the right-upper: siCOL18A1-ASx-5, and the right-lower: siTMPO-AS1-2 was administered).

FIG. 7B is a graph indicating changes in the tumor volumes. In FIG. 7B, "black square" indicates the result of the mice (n=7) to which "siControl" had been administered, "white circle" indicates the results of the mice (n=6) to which "siTMPO-AS1-2" had been administered, "white square" indicates the results of the mice (n=8) to which "siCOL18A1-ASx-1" had been administered, and "black triangle" indicates the result of the mice (n=7) to which "siCOL18A1-ASx-5" had been administered. Also, in this figure, "*" means p<0.05 and "**" means p<0.01.

From the results of FIGS. 7A and 7B, it has become evident that administration of siTMPO-AS1-2, siCOL18A1-ASx-1, or siCOL18A1-ASx-5 significantly suppresses the growth of the tumor derived from the OHTR cells in the mice.

From Test Example 1 to Test Example 7 described above, it has become evident that TMPO-AS1 and COL18A1-ASx identified as new non-coding RNA using breast cancer cells MCF-7 are expressed also in breast cancer cells other than MCF-7 cells and cells derived from cancers other than breast cancer. Furthermore, their expressions are clearly indicated by analysis using clinical samples of breast cancer. Therefore, it is suggested that TMPO-AS1 and COL18A1-ASx are involved with various cancers including breast cancer even in a clinical stage.

In addition, double-stranded nucleic acid molecules having high knockdown effects against TMPO-AS1 and COL18A1-ASx were obtained.

It has been confirmed that the double-stranded nucleic acid molecules suppress the cell proliferation in MCF-7 cells, OHTR cells, which are a breast cancer therapy-resistant model, and Ishikawa cells derived from endometrial cancer. The difference in the effects between the cells by the double-stranded nucleic acid molecules even having the same sequence is assumed to be due to the difference in the transfection efficiency and the gene expression level.

Remarkable tumor growth suppressive effects were observed in siTMPO-AS1-2 and siCOL18A1-ASx-5 which were excellent in the expression suppressive efficiency of non-coding RNA and the cell proliferation suppressive effects. Therefore, other double-stranded nucleic acid molecules observed to have effects at the cell level are also considered useful for cancer therapy.

In addition, it was indicated that the double-stranded nucleic acid molecules of the present invention suppressed the movements of breast cancer cells.

Furthermore, it was confirmed that the double-stranded nucleic acid molecules suppressed the growth of tumor in mice to which therapy-resistant breast cancer cells had been transplanted.

Therefore, it is indicated that the non-coding RNA has an action of promoting tumor growth in various kinds of cancers such as breast cancer including hormone therapy-resistant breast cancer and thus can be target molecules for breast cancer therapy and diagnosis. In addition, suppressants of the expressions of the non-coding RNA, especially siRNA, have proliferation suppressive effects in various kinds of cancer cells such as breast cancer cells including hormone therapy-resistant breast cancer cells and can be applied to clinical use for therapy of these cancers.

Also, it is considered that the double-stranded nucleic acid molecules targeting the non-coding RNA can be new target molecules for therapy that have different action mechanisms from the existing breast cancer therapeutic drugs against estrogen actions and HER2.

Also, it is considered that it is possible to reveal the proliferation mechanism of cancer from the actions of the non-coding RNA and apply the obtained findings to reveal of pathological condition.

Aspects of the present invention are, for example, as follows.

<1> A double-stranded nucleic acid molecule for suppressing expression of non-coding RNA, the double-stranded nucleic acid molecule including:

(a) a sense strand containing a nucleotide sequence corresponding to a target sequence set forth in any one of SEQ ID NOs: 5 to 11 and 26 to 31; and (b) an antisense strand containing a nucleotide sequence which is complementary to the sense strand in the (a) to form a double strand with the sense strand, wherein the non-coding RNA contains a base sequence set forth in any one of SEQ ID NOs: 1 to 4, a part of the base sequence, or both of the base sequence and the part.

<2> The double-stranded nucleic acid molecule according to <1>, wherein the sense strand is a sense strand containing a nucleotide sequence corresponding to the target sequence set forth in any one of SEQ ID NOs: 5, 6, 9, 10, 27, 28, 29, 30, and 31.

<3> The double-stranded nucleic acid molecule according to <1> or <2>, wherein the sense strand is a sense strand containing a nucleotide sequence corresponding to the target sequence set forth in any one of SEQ ID NOs: 6 and 28.

<4> The double-stranded nucleic acid molecule according to any one of <1> to <3>, wherein the double-stranded nucleic acid molecule is double-stranded RNA or double-stranded RNA-DNA chimera.

<5> The double-stranded nucleic acid molecule according to any one of <1> to <4>, wherein the double-stranded nucleic acid molecule is siRNA or chimeric siRNA.

<6> The double-stranded nucleic acid molecule according to any one of <1> to <5>, wherein the double-stranded nucleic acid molecule is siRNA.

<7> DNA including
a nucleotide sequence encoding the double-stranded nucleic acid molecule according to any one of <1> to <6>.

<8> A vector including
the DNA according to <7>.

<9> A cancer cell proliferation suppressant including
at least one of the double-stranded nucleic acid molecule according to any one of <1> to <6>, the DNA according to <7>, and the vector according to <8>.

<10> The cancer cell proliferation suppressant according to <9>, wherein the cancer cells are breast cancer cells.

<11> The cancer cell proliferation suppressant according to <10>, wherein the breast cancer cells are hormone therapy-resistant breast cancer cells.

<12> A method for suppressing proliferation of cancer cells, the method including
allowing the cancer cell proliferation suppressant according to any one of <9> to <11> to act on the cancer cells.

<13> The method for suppressing proliferation of cancer cells according to <12>, wherein the cancer cells are breast cancer cells.

<14> The method for suppressing proliferation of cancer cells according to <13>, wherein the breast cancer cells are hormone therapy-resistant breast cancer cells.

<15> A cancer cell movement suppressant including
at least one of the double-stranded nucleic acid molecule according to any one of <1> to <6>, the DNA according to <7>, and the vector according to <8>.

<16> The cancer cell movement suppressant according to <15>, wherein the cancer cells are breast cancer cells.

<17> The cancer cell movement suppressant according to <16>, wherein the breast cancer cells are hormone therapy-resistant breast cancer cells.

<18> A method for suppressing movements of cancer cells, the method including
allowing the cancer cell movement suppressant according to any one of <15> to <17> to act on the cancer cells.

<19> The method for suppressing movements of cancer cells according to <18>, wherein the cancer cells are breast cancer cells.

<20> The method for suppressing movements of cancer cells according to <19>, wherein the breast cancer cells are hormone therapy-resistant breast cancer cells.

<21> A drug for preventing or treating cancer, the drug including
at least one of the cancer cell proliferation suppressant according to any one of <9> to <11> and the cancer cell movement suppressant according to any one of <15> to <17>.

<22> The drug according to <21>, wherein the cancer is breast cancer.

<23> The drug according to <22>, wherein the breast cancer is hormone therapy-resistant breast cancer.

<24> A method for preventing or treating cancer, the method including administering the drug according to any one of <21> to <23> to an individual.

<25> The method for preventing or treating cancer according to <24>, wherein the cancer is breast cancer.

<27> The method for preventing or treating cancer according to <25>, wherein the breast cancer is hormone therapy-resistant breast cancer.

The invention claimed is:

1. A double-stranded nucleic acid molecule for suppressing expression of non-coding RNA, the double-stranded nucleic acid molecule consisting of:
   (a) a sense strand containing a nucleotide sequence corresponding to a target sequence set forth in any one of SEQ ID NOs: 26 to 31; and
   (b) an antisense strand containing a nucleotide sequence which is complementary to the sense strand in the (a) to form a double strand with the sense strand,
   wherein the non-coding RNA contains a base sequence set forth in any one of SEQ ID NOs: 2 to 4, a part of the base sequence, or both of the base sequence and the part, and
   wherein the double-stranded nucleic acid molecule is a combination of the sense strand and the antisense strand in any one of (i) to (vi) below:
   (i) a combination of the sense strand containing the nucleotide sequence corresponding to the target sequence set forth in SEQ ID NO: 26 and consisting of a base sequence set forth in SEQ ID NO: 32, and the antisense strand consisting of a base sequence set forth in SEQ ID NO: 33,
   (ii) a combination of the sense strand containing the nucleotide sequence corresponding to the target sequence set forth in SEQ ID NO: 27 and consisting of a base sequence set forth in SEQ ID NO: 34, and the antisense strand consisting of a base sequence set forth in SEQ ID NO: 35,
   (iii) a combination of the sense strand containing the nucleotide sequence corresponding to the target sequence set forth in SEQ ID NO: 28 and consisting of a base sequence set forth in SEQ ID NO: 36, and the antisense strand consisting of a base sequence set forth in SEQ ID NO: 37,
   (iv) a combination of the sense strand containing the nucleotide sequence corresponding to the target sequence set forth in SEQ ID NO: 29 and consisting of a base sequence set forth in SEQ ID NO: 38, and the antisense strand consisting of a base sequence set forth in SEQ ID NO: 39,
   (v) a combination of the sense strand containing the nucleotide sequence corresponding to the target sequence set forth in SEQ ID NO: 30 and consisting of a base sequence set forth in SEQ ID NO: 40, and the antisense strand consisting of a base sequence set forth in SEQ ID NO: 41, and
   (vi) a combination of the sense strand containing the nucleotide sequence corresponding to the target sequence set forth in SEQ ID NO: 31 and consisting of a base sequence set forth in SEQ ID NO: 42, and the antisense strand consisting of a base sequence set forth in SEQ ID NO: 43.

2. The double-stranded nucleic acid molecule according to claim 1, wherein the sense strand is a sense strand containing a nucleotide sequence corresponding to the target sequence set forth in any one of SEQ ID NOs: 27, 28, 29, 30, and 31.

3. The double-stranded nucleic acid molecule according to claim 1, wherein the sense strand is a sense strand containing a nucleotide sequence corresponding to the target sequence set forth in SEQ ID NO: 28.

4. The double-stranded nucleic acid molecule according to claim 1, wherein the double-stranded nucleic acid molecule is double-stranded RNA or double-stranded RNA-DNA chimera.

5. The double-stranded nucleic acid molecule according to claim 1, wherein the double-stranded nucleic acid molecule is siRNA or chimeric siRNA.

6. DNA comprising
   a nucleotide sequence encoding a double-stranded nucleic acid molecule for suppressing expression of non-coding RNA, the double-stranded nucleic acid molecule consisting of:
   (a) a sense strand containing a nucleotide sequence corresponding to a target sequence set forth in any one of SEQ ID NOs: 26 to 31; and
   (b) an antisense strand containing a nucleotide sequence which is complementary to the sense strand in the (a) to form a double strand with the sense strand, wherein the non-coding RNA contains a base sequence set forth in any one of SEQ ID NOs: 2 to 4, a part of the base sequence, or both of the base sequence and the part, wherein the double-stranded nucleic acid molecule is a combination of the sense strand and the antisense strand in any one of (i) to (vi) below:

(i) a combination of the sense strand containing the nucleotide sequence corresponding to the target sequence set forth in SEQ ID NO: 26 and consisting of a base sequence set forth in SEQ ID NO: 32, and the antisense strand consisting of a base sequence set forth in SEQ ID NO: 33, (ii) a combination of the sense strand containing the nucleotide sequence corresponding to the target sequence set forth in SEQ ID NO: 27 and consisting of a base sequence set forth in SEQ ID NO: 34, and the antisense strand consisting of a base sequence set forth in SEQ ID NO: 35, (iii) a combination of the sense strand containing the nucleotide sequence corresponding to the target sequence set forth in SEQ ID NO: 28 and consisting of a base sequence set forth in SEQ ID NO: 36, and the antisense strand consisting of a base sequence set forth in SEQ ID NO: 37, (iv) a combination of the sense strand containing the nucleotide sequence corresponding to the target sequence set forth in SEQ ID NO: 29 and consisting of a base sequence set forth in SEQ ID NO: 38, and the antisense strand consisting of a base sequence set forth in SEQ ID NO: 39, (v) a combination of the sense strand containing the nucleotide sequence corresponding to the target sequence set forth in SEQ ID NO: 30 and consisting of a base sequence set forth in SEQ ID NO: 40, and the antisense strand consisting of a base sequence set forth in SEQ ID NO: 41, and (vi) a combination of the sense strand containing the nucleotide sequence corresponding to the target sequence set forth in SEQ ID NO: 31 and consisting of a base sequence set forth in SEQ ID NO: 42, and the antisense strand consisting of a base sequence set forth in SEQ ID NO: 43.

7. A vector comprising a DNA containing a nucleotide sequence encoding a double-stranded nucleic acid molecule for suppressing expression of non-coding RNA, the double-stranded nucleic acid molecule consisting of:

(a) a sense strand containing a nucleotide sequence corresponding to a target sequence set forth in any one of SEQ ID NOs: 26 to 31; and (b) an antisense strand containing a nucleotide sequence which is complementary to the sense strand in the (a) to form a double strand with the sense strand, wherein the non-coding RNA contains a base sequence set forth in any one of SEQ ID NOs: 2 to 4, a part of the base sequence, or both of the base sequence and the part and wherein the double-stranded nucleic acid molecule is a combination of the sense strand and the antisense strand in any one of (i) to (vi) below:

(i) a combination of the sense strand containing the nucleotide sequence corresponding to the target sequence set forth in SEQ ID NO: 26 and consisting of a base sequence set forth in SEQ ID NO: 32, and the antisense strand consisting of a base sequence set forth in SEQ ID NO: 33, (ii) a combination of the sense strand containing the nucleotide sequence corresponding to the target sequence set forth in SEQ ID NO: 27 and consisting of a base sequence set forth in SEQ ID NO: 34, and the antisense strand consisting of a base sequence set forth in SEQ ID NO: 35, (iii) a combination of the sense strand containing the nucleotide sequence corresponding to the target sequence set forth in SEQ ID NO: 28 and consisting of a base sequence set forth in SEQ ID NO: 36, and the antisense strand consisting of a base sequence set forth in SEQ ID NO: 37, (iv) a combination of the sense strand containing the nucleotide sequence corresponding to the target sequence set forth in SEQ ID NO: 29 and consisting of a base sequence set forth in SEQ ID NO: 38, and the antisense strand consisting of a base sequence set forth in SEQ ID NO: 39, (v) a combination of the sense strand containing the nucleotide sequence corresponding to the target sequence set forth in SEQ ID NO: 30 and consisting of a base sequence set forth in SEQ ID NO: 40, and the antisense strand consisting of a base sequence set forth in SEQ ID NO: 41, and (vi) a combination of the sense strand containing the nucleotide sequence corresponding to the target sequence set forth in SEQ ID NO: 31 and consisting of a base sequence set forth in SEQ ID NO: 42, and the antisense strand consisting of a base sequence set forth in SEQ ID NO: 43.

8. A cancer cell proliferation suppressant comprising at least one of a double-stranded nucleic acid molecule, DNA, and a vector, wherein the double-stranded nucleic acid molecule is a double-stranded nucleic acid molecule for suppressing expression of non-coding RNA, the double-stranded nucleic acid molecule consisting of:

(a) a sense strand containing a nucleotide sequence corresponding to a target sequence set forth in any one of SEQ ID NOs: 26 to 31; and (b) an antisense strand containing a nucleotide sequence which is complementary to the sense strand in the (a) to form a double strand with the sense strand, the non-coding RNA containing a base sequence set forth in any one of SEQ ID NOs: 2 to 4, a part of the base sequence, or both of the base sequence and the part, and wherein the double-stranded nucleic acid molecule is a combination of the sense strand and the antisense strand in any one of (i) to (vi) below:

(i) a combination of the sense strand containing the nucleotide sequence corresponding to the target sequence set forth in SEQ ID NO: 26 and consisting of a base sequence set forth in SEQ ID NO: 32, and the antisense strand consisting of a base sequence set forth in SEQ ID NO: 33, (ii) a combination of the sense strand containing the nucleotide sequence corresponding to the target sequence set forth in SEQ ID NO: 27 and consisting of a base sequence set forth in SEQ ID NO: 34, and the antisense strand consisting of a base sequence set forth in SEQ ID NO: 35, (iii) a combination of the sense strand containing the nucleotide sequence corresponding to the target sequence set forth in SEQ ID NO: 28 and consisting of a base sequence set forth in SEQ ID NO: 36, and the antisense strand consisting of a base sequence set forth in SEQ ID NO: 37, (iv) a combination of the sense strand containing the nucleotide sequence corresponding to the target sequence set forth in SEQ ID NO: 29 and consisting of a base sequence set forth in SEQ ID NO: 38, and the antisense strand consisting of a base sequence set forth in SEQ ID NO: 39, (v) a combination of the sense strand containing the nucleotide sequence corresponding to the target sequence set forth in SEQ ID NO: 30 and consisting of a base sequence set forth in SEQ ID NO: 40, and the antisense strand consisting of a base sequence set forth in SEQ ID NO: 41, and (vi) a combination of the sense strand containing the nucleotide sequence corresponding to the target sequence set forth in SEQ ID NO: 31 and consisting of a base sequence set forth in SEQ ID NO: 42, and the antisense strand consisting of a base sequence set forth in SEQ ID NO: 43;

wherein the DNA is DNA containing a nucleotide sequence encoding a double-stranded nucleic acid molecule for suppressing expression of non-coding RNA, the double-stranded nucleic acid molecule consisting of:

(a) a sense strand containing a nucleotide sequence corresponding to a target sequence set forth in any one of SEQ ID NOs: 26 to 31; and (b) an antisense strand containing a nucleotide sequence which is complementary to the sense strand in the (a) to form a double strand with the sense strand, the non-coding RNA containing a base sequence set forth in any one of SEQ ID NOs: 2 to 4, a part of the base sequence, or both of the base sequence and the part, and wherein the double-stranded nucleic acid molecule is a combination of the sense strand and the antisense strand in any one of (i) to (vi) below:

(i) a combination of the sense strand containing the nucleotide sequence corresponding to the target sequence set forth in SEQ ID NO: 26 and consisting of a base sequence set forth in SEQ ID NO: 32, and the antisense strand consisting of a base sequence set forth in SEQ ID NO: 33, (ii) a combination of the sense strand containing the nucleotide sequence corresponding to the target sequence set forth in SEQ ID NO: 27 and consisting of a base sequence set forth in SEQ ID NO: 34, and the antisense strand consisting of a base sequence set forth in SEQ ID NO: 35, (iii) a combination of the sense strand containing the nucleotide sequence corresponding to the target sequence set forth in SEQ ID NO: 28 and consisting of a base sequence set forth in SEQ ID NO: 36, and the antisense strand consisting of a base sequence set forth in SEQ ID NO: 37, (iv) a combination of the sense strand containing the nucleotide sequence corresponding to the target sequence set forth in SEQ ID NO: 29 and consisting of a base sequence set forth in SEQ ID NO: 38, and the antisense strand consisting of a base sequence set forth in SEQ ID NO: 39, (v) a combination of the sense strand containing the nucleotide sequence corresponding to the target sequence set forth in SEQ ID NO: 30 and consisting of a base sequence set forth in SEQ ID NO: 40, and the antisense strand consisting of a base sequence set forth in SEQ ID NO: 41, and (vi) a combination of the sense strand containing the nucleotide sequence corresponding to the target sequence set forth in SEQ ID NO: 31 and consisting of a base sequence set forth in SEQ ID NO: 42, and the antisense strand consisting of a base sequence set forth in SEQ ID NO: 43;

wherein the vector is a vector containing DNA containing a nucleotide sequence encoding a double-stranded nucleic acid molecule for suppressing expression of non-coding RNA, the double-stranded nucleic acid molecule consisting of:

(a) a sense strand containing a nucleotide sequence corresponding to a target sequence set forth in any one of SEQ ID NOs: 26 to 31; and (b) an antisense strand containing a nucleotide sequence which is complementary to the sense strand in the (a) to form a double strand with the sense strand, the non-coding RNA containing a base sequence set forth in any one of SEQ ID NOs: 2 to 4, a part of the base sequence, or both of the base sequence and the part and wherein the double-stranded nucleic acid molecule is a combination of the sense strand and the antisense strand in any one of (i) to (vi) below:

(i) a combination of the sense strand containing the nucleotide sequence corresponding to the target sequence set forth in SEQ ID NO: 26 and consisting of a base sequence set forth in SEQ ID NO: 32, and the antisense strand consisting of a base sequence set forth in SEQ ID NO: 33, (ii) a combination of the sense strand containing the nucleotide sequence corresponding to the target sequence set forth in SEQ ID NO: 27 and consisting of a base sequence set forth in SEQ ID NO: 34, and the antisense strand consisting of a base sequence set forth in SEQ ID NO: 35, (iii) a combination of the sense strand containing the nucleotide sequence corresponding to the target sequence set forth in SEQ ID NO: 28 and consisting of a base sequence set forth in SEQ ID NO: 36, and the antisense strand consisting of a base sequence set forth in SEQ ID NO: 37, (iv) a combination of the sense strand containing the nucleotide sequence corresponding to the target sequence set forth in SEQ ID NO: 29 and consisting of a base sequence set forth in SEQ ID NO: 38, and the antisense strand consisting of a base sequence set forth in SEQ ID NO: 39, (v) a combination of the sense strand containing the nucleotide sequence corresponding to the target sequence set forth in SEQ ID NO: 30 and consisting of a base sequence set forth in SEQ ID NO: 40, and the antisense strand consisting of a base sequence set forth in SEQ ID NO: 41, and (vi) a combination of the sense strand containing the nucleotide sequence corresponding to the target sequence set forth in SEQ ID NO: 31 and consisting of a base sequence set forth in SEQ ID NO: 42, and the antisense strand consisting of a base sequence set forth in SEQ ID NO: 43.

9. A cancer cell movement suppressant comprising
at least one of a double-stranded nucleic acid molecule, DNA, and a vector,
wherein the double-stranded nucleic acid molecule is a double-stranded nucleic acid molecule for suppressing expression of non-coding RNA, the double-stranded nucleic acid molecule consisting of:
  (a) a sense strand containing a nucleotide sequence corresponding to a target sequence set forth in any one of SEQ ID NOs: 26 to 31; and
  (b) an antisense strand containing a nucleotide sequence which is complementary to the sense strand in the (a) to form a double strand with the sense strand,
  the non-coding RNA containing a base sequence set forth in any one of SEQ ID NOs: 2 to 4, a part of the base sequence, or both of the base sequence and the part, and
  wherein the double-stranded nucleic acid molecule is a combination of the sense strand and the antisense strand in any one of (i) to (vi) below:
  (i) a combination of the sense strand containing the nucleotide sequence corresponding to the target sequence set forth in SEQ ID NO: 26 and consisting of a base sequence set forth in SEQ ID NO: 32, and the antisense strand consisting of a base sequence set forth in SEQ ID NO: 33,
  (ii) a combination of the sense strand containing the nucleotide sequence corresponding to the target sequence set forth in SEQ ID NO: 27 and consisting of a base sequence set forth in SEQ ID NO: 34, and the antisense strand consisting of a base sequence set forth in SEQ ID NO: 35,
  (iii) a combination of the sense strand containing the nucleotide sequence corresponding to the target sequence set forth in SEQ ID NO: 28 and consisting of a base sequence set forth in SEQ ID NO: 36, and the antisense strand consisting of a base sequence set forth in SEQ ID NO: 37,
  (iv) a combination of the sense strand containing the nucleotide sequence corresponding to the target sequence set forth in SEQ ID NO: 29 and consisting of a base sequence set forth in SEQ ID NO: 38, and the antisense strand consisting of a base sequence set forth in SEQ ID NO: 39,
  (v) a combination of the sense strand containing the nucleotide sequence corresponding to the target sequence set forth in SEQ ID NO: 30 and consisting of a base sequence set forth in SEQ ID NO: 40, and the antisense strand consisting of a base sequence set forth in SEQ ID NO: 41, and
  (vi) a combination of the sense strand containing the nucleotide sequence corresponding to the target sequence set forth in SEQ ID NO: 31 and consisting of a base sequence set forth in SEQ ID NO: 42, and the antisense strand consisting of a base sequence set forth in SEQ ID NO: 43;
wherein the DNA is DNA containing a nucleotide sequence encoding a double-stranded nucleic acid molecule for suppressing expression of non-coding RNA, the double-stranded nucleic acid molecule consisting of:
  (a) a sense strand containing a nucleotide sequence corresponding to a target sequence set forth in any one of SEQ ID NOs: 26 to 31; and
  (b) an antisense strand containing a nucleotide sequence which is complementary to the sense strand in the (a) to form a double strand with the sense strand,
  the non-coding RNA containing a base sequence set forth in any one of SEQ ID NOs: 2 to 4, a part of the base sequence, or both of the base sequence and the part, and
  wherein the double-stranded nucleic acid molecule is a combination of the sense strand and the antisense strand in any one of (i) to (vi) below:
  (i) a combination of the sense strand containing the nucleotide sequence corresponding to the target sequence set forth in SEQ ID NO: 26 and consisting of a base sequence set forth in SEQ ID NO: 32, and the antisense strand consisting of a base sequence set forth in SEQ ID NO: 33,
  (ii) a combination of the sense strand containing the nucleotide sequence corresponding to the target sequence set forth in SEQ ID NO: 27 and consisting of a base sequence set forth in SEQ ID NO: 34, and the antisense strand consisting of a base sequence set forth in SEQ ID NO: 35,
  (iii) a combination of the sense strand containing the nucleotide sequence corresponding to the target sequence set forth in SEQ ID NO: 28 and consisting of a base sequence set forth in SEQ ID NO: 36, and the antisense strand consisting of a base sequence set forth in SEQ ID NO: 37,
  (iv) a combination of the sense strand containing the nucleotide sequence corresponding to the target sequence set forth in SEQ ID NO: 29 and consisting of a base sequence set forth in SEQ ID NO: 38, and the antisense strand consisting of a base sequence set forth in SEQ ID NO: 39,
  (v) a combination of the sense strand containing the nucleotide sequence corresponding to the target sequence set forth in SEQ ID NO: 30 and consisting of a base sequence set forth in SEQ ID NO: 40, and the antisense strand consisting of a base sequence set forth in SEQ ID NO: 41, and
  (vi) a combination of the sense strand containing the nucleotide sequence corresponding to the target sequence set forth in SEQ ID NO: 31 and consisting of a base sequence set forth in SEQ ID NO: 42, and the antisense strand consisting of a base sequence set forth in SEQ ID NO: 43;
wherein the vector is a vector containing DNA containing a nucleotide sequence encoding a double-stranded nucleic acid molecule for suppressing expression of non-coding RNA, the double-stranded nucleic acid molecule consisting of:
  (a) a sense strand containing a nucleotide sequence corresponding to a target sequence set forth in any one of SEQ ID NOs: 26 to 31; and
  (b) an antisense strand containing a nucleotide sequence which is complementary to the sense strand in the (a) to form a double strand with the sense strand,
  the non-coding RNA containing a base sequence set forth in any one of SEQ ID NOs: 2 to 4, a part of the base sequence, or both of the base sequence and the part, and
  wherein the double-stranded nucleic acid molecule is a combination of the sense strand and the antisense strand in any one of (i) to (vi) below:

(i) a combination of the sense strand containing the nucleotide sequence corresponding to the target sequence set forth in SEQ ID NO: 26 and consisting of a base sequence set forth in SEQ ID NO: 32, and the antisense strand consisting of a base sequence set forth in SEQ ID NO: 33,
(ii) a combination of the sense strand containing the nucleotide sequence corresponding to the target sequence set forth in SEQ ID NO: 27 and consisting of a base sequence set forth in SEQ ID NO: 34, and the antisense strand consisting of a base sequence set forth in SEQ ID NO: 35,
(iii) a combination of the sense strand containing the nucleotide sequence corresponding to the target sequence set forth in SEQ ID NO: 28 and consisting of a base sequence set forth in SEQ ID NO: 36, and the antisense strand consisting of a base sequence set forth in SEQ ID NO: 37,
(iv) a combination of the sense strand containing the nucleotide sequence corresponding to the target sequence set forth in SEQ ID NO: 29 and consisting of a base sequence set forth in SEQ ID NO: 38, and the antisense strand consisting of a base sequence set forth in SEQ ID NO: 39,
(v) a combination of the sense strand containing the nucleotide sequence corresponding to the target sequence set forth in SEQ ID NO: 30 and consisting of a base sequence set forth in SEQ ID NO: 40, and the antisense strand consisting of a base sequence set forth in SEQ ID NO: 41, and
(vi) a combination of the sense strand containing the nucleotide sequence corresponding to the target sequence set forth in SEQ ID NO: 31 and consisting of a base sequence set forth in SEQ ID NO: 42, and the antisense strand consisting of a base sequence set forth in SEQ ID NO: 43.

10. A drug for preventing or treating cancer, the drug comprising
at least one of a cancer cell proliferation suppressant and a cancer cell movement suppressant,
wherein the cancer cell proliferation suppressant contains at least one of a double-stranded nucleic acid molecule, DNA, and a vector,
wherein the double-stranded nucleic acid molecule is a double-stranded nucleic acid molecule for suppressing expression of non-coding RNA, the double-stranded nucleic acid molecule consisting of:
(a) a sense strand containing a nucleotide sequence corresponding to a target sequence set forth in any one of SEQ ID NOs: 26 to 31; and
(b) an antisense strand containing a nucleotide sequence which is complementary to the sense strand in the (a) to form a double strand with the sense strand,
the non-coding RNA containing a base sequence set forth in any one of SEQ ID NOs: 2 to 4, a part of the base sequence, or both of the base sequence and the part, and
wherein the double-stranded nucleic acid molecule is a combination of the sense strand and the antisense strand in any one of (i) to (vi) below:
(i) a combination of the sense strand containing the nucleotide sequence corresponding to the target sequence set forth in SEQ ID NO: 26 and consisting of a base sequence set forth in SEQ ID NO: 32, and the antisense strand consisting of a base sequence set forth in SEQ ID NO: 33,
(ii) a combination of the sense strand containing the nucleotide sequence corresponding to the target sequence set forth in SEQ ID NO: 27 and consisting of a base sequence set forth in SEQ ID NO: 34, and the antisense strand consisting of a base sequence set forth in SEQ ID NO: 35,
(iii) a combination of the sense strand containing the nucleotide sequence corresponding to the target sequence set forth in SEQ ID NO: 28 and consisting of a base sequence set forth in SEQ ID NO: 36, and the antisense strand consisting of a base sequence set forth in SEQ ID NO: 37,
(iv) a combination of the sense strand containing the nucleotide sequence corresponding to the target sequence set forth in SEQ ID NO: 29 and consisting of a base sequence set forth in SEQ ID NO: 38, and the antisense strand consisting of a base sequence set forth in SEQ ID NO: 39,
(v) a combination of the sense strand containing the nucleotide sequence corresponding to the target sequence set forth in SEQ ID NO: 30 and consisting of a base sequence set forth in SEQ ID NO: 40, and the antisense strand consisting of a base sequence set forth in SEQ ID NO: 41, and
(vi) a combination of the sense strand containing the nucleotide sequence corresponding to the target sequence set forth in SEQ ID NO: 31 and consisting of a base sequence set forth in SEQ ID NO: 42, and the antisense strand consisting of a base sequence set forth in SEQ ID NO: 43;
wherein the DNA is DNA containing a nucleotide sequence encoding a double-stranded nucleic acid molecule for suppressing expression of non-coding RNA, the double-stranded nucleic acid molecule consisting of:
(a) a sense strand containing a nucleotide sequence corresponding to a target sequence set forth in any one of SEQ ID NOs: 26 to 31; and
(b) an antisense strand containing a nucleotide sequence which is complementary to the sense strand in the (a) to form a double strand with the sense strand,
the non-coding RNA containing a base sequence set forth in any one of SEQ ID NOs: 2 to 4, a part of the base sequence, or both of the base sequence and the part, and
wherein the double-stranded nucleic acid molecule is a combination of the sense strand and the antisense strand in any one of (i) to (vi) below:
(i) a combination of the sense strand containing the nucleotide sequence corresponding to the target sequence set forth in SEQ ID NO: 26 and consisting of a base sequence set forth in SEQ ID NO: 32, and the antisense strand consisting of a base sequence set forth in SEQ ID NO: 33,
(ii) a combination of the sense strand containing the nucleotide sequence corresponding to the target sequence set forth in SEQ ID NO: 27 and consisting of a base sequence set forth in SEQ ID NO: 34, and the antisense strand consisting of a base sequence set forth in SEQ ID NO: 35,
(iii) a combination of the sense strand containing the nucleotide sequence corresponding to the target sequence set forth in SEQ ID NO: 28 and consisting of a base sequence set forth in SEQ ID NO: 36, and the antisense strand consisting of a base sequence set forth in SEQ ID NO: 37, (iv) a combination of the sense strand containing the nucleotide sequence corresponding to the target sequence set forth in SEQ ID NO: 29 and consisting of a base sequence set forth in SEQ ID NO: 38, and the antisense strand consisting of a base sequence set forth in SEQ ID NO: 39, (v) a combination of the sense strand containing the nucleotide sequence corresponding to the target sequence set forth in SEQ ID NO: 30 and consisting of a base sequence set forth in SEQ ID NO: 40, and the antisense strand consisting of a base sequence set forth in SEQ ID NO: 41, and (vi) a combination of the sense strand containing the nucleotide sequence corresponding to the target sequence set forth in SEQ ID NO: 31 and consisting of a base sequence set forth in SEQ ID NO: 42, and the antisense strand consisting of a base sequence set forth in SEQ ID NO: 43;

wherein the vector is a vector containing DNA containing a nucleotide sequence encoding a double-stranded nucleic acid molecule for suppressing expression of non-coding RNA, the double-stranded nucleic acid molecule consisting of:

(a) a sense strand containing a nucleotide sequence corresponding to a target sequence set forth in any one of SEQ ID NOs: 26 to 31; and (b) an antisense strand containing a nucleotide sequence which is complementary to the sense strand in the (a) to form a double strand with the sense strand, the non-coding RNA containing a base sequence set forth in any one of SEQ ID NOs: 2 to 4, a part of the base sequence, or both of the base sequence and the part, and wherein the double-stranded nucleic acid molecule is a combination of the sense strand and the antisense strand in any one of (i) to (vi) below:

(i) a combination of the sense strand containing the nucleotide sequence corresponding to the target sequence set forth in SEQ ID NO: 26 and consisting of a base sequence set forth in SEQ ID NO: 32, and the antisense strand consisting of a base sequence set forth in SEQ ID NO: 33, (ii) a combination of the sense strand containing the nucleotide sequence corresponding to the target sequence set forth in SEQ ID NO: 27 and consisting of a base sequence set forth in SEQ ID NO: 34, and the antisense strand consisting of a base sequence set forth in SEQ ID NO: 35, (iii) a combination of the sense strand containing the nucleotide sequence corresponding to the target sequence set forth in SEQ ID NO: 28 and consisting of a base sequence set forth in SEQ ID NO: 36, and the antisense strand consisting of a base sequence set forth in SEQ ID NO: 37, (iv) a combination of the sense strand containing the nucleotide sequence corresponding to the target sequence set forth in SEQ ID NO: 29 and consisting of a base sequence set forth in SEQ ID NO: 38, and the antisense strand consisting of a base sequence set forth in SEQ ID NO: 39, (v) a combination of the sense strand containing the nucleotide sequence corresponding to the target sequence set forth in SEQ ID NO: 30 and consisting of a base sequence set forth in SEQ ID NO: 40, and the antisense strand consisting of a base sequence set forth in SEQ ID NO: 41, and (vi) a combination of the sense strand containing the nucleotide sequence corresponding to the target sequence set forth in SEQ ID NO: 31 and consisting of a base sequence set forth in SEQ ID NO: 42, and the antisense strand consisting of a base sequence set forth in SEQ ID NO: 43;

wherein the cancer cell movement suppressant contains at least one of a double-stranded nucleic acid molecule, DNA, and a vector, wherein the double-stranded nucleic acid molecule is a double-stranded nucleic acid molecule for suppressing expression of non-coding RNA, the double-stranded nucleic acid molecule consisting of:

(a) a sense strand containing a nucleotide sequence corresponding to a target sequence set forth in any one of SEQ ID NOs: 26 to 31; and (b) an antisense strand containing a nucleotide sequence which is complementary to the sense strand in the (a) to form a double strand with the sense strand, the non-coding RNA containing a base sequence set forth in any one of SEQ ID NOs: 2 to 4, a part of the base sequence, or both of the base sequence and the part, and wherein the double-stranded nucleic acid molecule is a combination of the sense strand and the antisense strand in any one of (i) to (vi) below:

(i) a combination of the sense strand containing the nucleotide sequence corresponding to the target sequence set forth in SEQ ID NO: 26 and consisting of a base sequence set forth in SEQ ID NO: 32, and the antisense strand consisting of a base sequence set forth in SEQ ID NO: 33, (ii) a combination of the sense strand containing the nucleotide sequence corresponding to the target sequence set forth in SEQ ID NO: 27 and consisting of a base sequence set forth in SEQ ID NO: 34, and the antisense strand consisting of a base sequence set forth in SEQ ID NO: 35, (iii) a combination of the sense strand containing the nucleotide sequence corresponding to the target sequence set forth in SEQ ID NO: 28 and consisting of a base sequence set forth in SEQ ID NO: 36, and the antisense strand consisting of a base sequence set forth in SEQ ID NO: 37, (iv) a combination of the sense strand containing the nucleotide sequence corresponding to the target sequence set forth in SEQ ID NO: 29 and consisting of a base sequence set forth in SEQ ID NO: 38, and the antisense strand consisting of a base sequence set forth in SEQ ID NO: 39, (v) a combination of the sense strand containing the nucleotide sequence corresponding to the target sequence set forth in SEQ ID NO: 30 and consisting of a base sequence set forth in SEQ ID NO: 40, and the antisense strand consisting of a base sequence set forth in SEQ ID NO: 41, and (vi) a combination of the sense strand containing the nucleotide sequence corresponding to the target sequence set forth in SEQ ID NO: 31 and consisting of a base sequence set forth in SEQ ID NO: 42, and the antisense strand consisting of a base sequence set forth in SEQ ID NO: 43;

wherein the DNA is DNA containing a nucleotide sequence encoding a double-stranded nucleic acid molecule for suppressing expression of non-coding RNA, the double-stranded nucleic acid molecule consisting of:
(a) a sense strand containing a nucleotide sequence corresponding to a target sequence set forth in any one of SEQ ID NOs: 26 to 31; and
(b) an antisense strand containing a nucleotide sequence which is complementary to the sense strand in the (a) to form a double strand with the sense strand,
the non-coding RNA containing a base sequence set forth in any one of SEQ ID NOs: 2 to 4, a part of the base sequence, or both of the base sequence and the part, and
wherein the double-stranded nucleic acid molecule is a combination of the sense strand and the antisense strand in any one of (i) to (vi) below:
(i) a combination of the sense strand containing the nucleotide sequence corresponding to the target sequence set forth in SEQ ID NO: 26 and consisting of a base sequence set forth in SEQ ID NO: 32, and the antisense strand consisting of a base sequence set forth in SEQ ID NO: 33,
(ii) a combination of the sense strand containing the nucleotide sequence corresponding to the target sequence set forth in SEQ ID NO: 27 and consisting of a base sequence set forth in SEQ ID NO: 34, and the antisense strand consisting of a base sequence set forth in SEQ ID NO: 35,
(iii) a combination of the sense strand containing the nucleotide sequence corresponding to the target sequence set forth in SEQ ID NO: 28 and consisting of a base sequence set forth in SEQ ID NO: 36, and the antisense strand consisting of a base sequence set forth in SEQ ID NO: 37,
(iv) a combination of the sense strand containing the nucleotide sequence corresponding to the target sequence set forth in SEQ ID NO: 29 and consisting of a base sequence set forth in SEQ ID NO: 38, and the antisense strand consisting of a base sequence set forth in SEQ ID NO: 39,
(v) a combination of the sense strand containing the nucleotide sequence corresponding to the target sequence set forth in SEQ ID NO: 30 and consisting of a base sequence set forth in SEQ ID NO: 40, and the antisense strand consisting of a base sequence set forth in SEQ ID NO: 41, and
(vi) a combination of the sense strand containing the nucleotide sequence corresponding to the target sequence set forth in SEQ ID NO: 31 and consisting of a base sequence set forth in SEQ ID NO: 42, and the antisense strand consisting of a base sequence set forth in SEQ ID NO: 43;
wherein the vector is a vector containing DNA containing a nucleotide sequence encoding a double-stranded nucleic acid molecule for suppressing expression of non-coding RNA, the double-stranded nucleic acid molecule consisting of:
(a) a sense strand containing a nucleotide sequence corresponding to a target sequence set forth in any one of SEQ ID NOs: 26 to 31; and
(b) an antisense strand containing a nucleotide sequence which is complementary to the sense strand in the (a) to form a double strand with the sense strand,
the non-coding RNA containing a base sequence set forth in any one of SEQ ID NOs: 2 to 4, a part of the base sequence, or both of the base sequence and the part, and
wherein the double-stranded nucleic acid molecule is a combination of the sense strand and the antisense strand in any one of (i) to (vi) below:
(i) a combination of the sense strand containing the nucleotide sequence corresponding to the target sequence set forth in SEQ ID NO: 26 and consisting of a base sequence set forth in SEQ ID NO: 32, and the antisense strand consisting of a base sequence set forth in SEQ ID NO: 33,
(ii) a combination of the sense strand containing the nucleotide sequence corresponding to the target sequence set forth in SEQ ID NO: 27 and consisting of a base sequence set forth in SEQ ID NO: 34, and the antisense strand consisting of a base sequence set forth in SEQ ID NO: 35,
(iii) a combination of the sense strand containing the nucleotide sequence corresponding to the target sequence set forth in SEQ ID NO: 28 and consisting of a base sequence set forth in SEQ ID NO: 36, and the antisense strand consisting of a base sequence set forth in SEQ ID NO: 37,
(iv) a combination of the sense strand containing the nucleotide sequence corresponding to the target sequence set forth in SEQ ID NO: 29 and consisting of a base sequence set forth in SEQ ID NO: 38, and the antisense strand consisting of a base sequence set forth in SEQ ID NO: 39,
(v) a combination of the sense strand containing the nucleotide sequence corresponding to the target sequence set forth in SEQ ID NO: 30 and consisting of a base sequence set forth in SEQ ID NO: 40, and the antisense strand consisting of a base sequence set forth in SEQ ID NO: 41, and
(vi) a combination of the sense strand containing the nucleotide sequence corresponding to the target sequence set forth in SEQ ID NO: 31 and consisting of a base sequence set forth in SEQ ID NO: 42, and the antisense strand consisting of a base sequence set forth in SEQ ID NO: 43.

* * * * *